US007842683B2

(12) United States Patent
Koppel

(10) Patent No.: US 7,842,683 B2
(45) Date of Patent: Nov. 30, 2010

(54) NEUROTHERAPEUTIC COMPOSITIONS AND METHOD

(75) Inventor: Gary A. Koppel, Indianapolis, IN (US)

(73) Assignee: Revaax Pharmaceuticals, LLC, Indianapolis, IN (US)

( * ) Notice: Subject to any disclaimer, the term of this patent is extended or adjusted under 35 U.S.C. 154(b) by 353 days.

(21) Appl. No.: 12/018,542

(22) Filed: Jan. 23, 2008

(65) Prior Publication Data

US 2008/0200447 A1 Aug. 21, 2008

Related U.S. Application Data

(60) Continuation of application No. 10/658,667, filed on Sep. 9, 2003, now abandoned, which is a division of application No. 09/640,363, filed on Aug. 16, 2000, now Pat. No. 6,627,625.

(60) Provisional application No. 60/149,115, filed on Aug. 16, 1999, provisional application No. 60/172,452, filed on Dec. 17, 1999, provisional application No. 60/176,570, filed on Jan. 18, 2000, provisional application No. 60/194,534, filed on Apr. 4, 2000.

(51) Int. Cl.
*A61K 31/545* (2006.01)
*A61K 31/397* (2006.01)
*A61K 31/5383* (2006.01)

(52) U.S. Cl. ............. 514/200; 514/210.01; 514/210.08

(58) Field of Classification Search ................ 514/200, 514/210.01, 210.08
See application file for complete search history.

(56) References Cited

U.S. PATENT DOCUMENTS

| | | | |
|---|---|---|---|
| 4,138,486 A | 2/1979 | Narisada et al. | |
| 4,234,579 A | 11/1980 | Barth | |
| 4,268,503 A * | 5/1981 | Imanaka et al. | 424/114 |
| 4,302,447 A * | 11/1981 | Horrobin | 424/642 |
| 4,349,672 A | 9/1982 | Montavon et al. | |
| 4,529,722 A | 7/1985 | Matsumura et al. | |
| 4,594,247 A * | 6/1986 | Brier | 424/114 |
| 5,698,221 A | 12/1997 | Patel et al. | |
| 5,763,603 A * | 6/1998 | Trickes | 540/310 |
| 5,795,877 A * | 8/1998 | Jackson et al. | 514/75 |
| 5,824,662 A * | 10/1998 | Slusher et al. | 514/75 |
| 5,827,537 A | 10/1998 | Palepu et al. | |
| 5,863,536 A * | 1/1999 | Jackson et al. | 424/130.1 |
| 5,880,112 A * | 3/1999 | Jackson et al. | 514/121 |
| 5,905,076 A * | 5/1999 | Singh et al. | 514/210.06 |
| 5,912,242 A * | 6/1999 | Pevarello et al. | 514/210.02 |
| 5,968,915 A * | 10/1999 | Jackson et al. | 514/89 |
| 5,977,090 A * | 11/1999 | Slusher et al. | 514/143 |
| 6,004,946 A * | 12/1999 | Slusher et al. | 514/75 |
| 6,015,809 A * | 1/2000 | Zhu et al. | 514/210.03 |
| 6,017,903 A * | 1/2000 | Slusher et al. | 514/75 |
| 6,204,260 B1 * | 3/2001 | Bruns et al. | 514/210.1 |
| 6,426,342 B2 | 7/2002 | Koppel | |
| 6,489,319 B2 | 12/2002 | Koppel et al. | |
| 6,610,681 B1 | 8/2003 | Koppel | |
| 6,627,625 B1 | 9/2003 | Koppel | |
| 7,166,626 B2 | 1/2007 | Koppel | |
| 2001/0011085 A1 | 8/2001 | Alpegiani et al. | |
| 2002/0002159 A1 * | 1/2002 | Koppel | 514/210.09 |
| 2002/0002876 A1 * | 1/2002 | Bezet | 74/594.6 |
| 2002/0028761 A1 | 3/2002 | Koppel et al. | |
| 2002/0049187 A1 * | 4/2002 | Bruns et al. | 514/151 |
| 2004/0014739 A1 | 1/2004 | Koppel | |
| 2007/0093466 A1 | 4/2007 | Koppel | |
| 2007/0249523 A1 | 10/2007 | Koppel et al. | |
| 2008/0176825 A1 | 7/2008 | Koppel et al. | |
| 2008/0200447 A1 | 8/2008 | Koppel | |

FOREIGN PATENT DOCUMENTS

| | | | |
|---|---|---|---|
| GB | 1508977 | * | 4/1978 |
| WO | 95/20980 | | 8/1995 |
| WO | WO9520980 | * | 8/1995 |
| WO | 97/10247 | | 3/1997 |
| WO | WO9710247 | * | 3/1997 |
| WO | 97/35839 | | 10/1997 |
| WO | WO9735839 | * | 10/1997 |
| WO | 97/48400 | | 12/1997 |
| WO | 98/13044 | | 4/1998 |
| WO | 98/13046 | | 4/1998 |
| WO | 98/32766 | | 7/1998 |
| WO | WO9832766 | * | 7/1998 |
| WO | 98/45256 | | 10/1998 |

(Continued)

OTHER PUBLICATIONS

Batueva, I.V., et al., "Effect of Penicillin on the Synaptic Activity of Isolated Spinal Cord Motor Neurons in the Lamprey," Neir ofiziologiia, vol. 24, No. 2, 1992, English Abstract, 2 pages.

(Continued)

*Primary Examiner*—Raymond J Henley, III
(74) *Attorney, Agent, or Firm*—Venable LLP; Michael A. Gollin; Keith G. Haddaway

(57) ABSTRACT

Administration of β-Lactam compounds, including β-lactam antibiotics and β-lactamase inhibitors provides significant neurotropic effects in warm-blooded vertebrates evidence inter alia by anxiolytic and anti-aggressive behavior modification and enhanced cognition. Therapeutic methods for using such compounds and their pharmaceutical formulations are described.

30 Claims, 37 Drawing Sheets

FOREIGN PATENT DOCUMENTS

| | | |
|---|---|---|
| WO | 98/47906 | 10/1998 |
| WO | 98/53812 | 12/1998 |
| WO | 99/33847 | 7/1999 |
| WO | 99/36403 | 7/1999 |
| WO | 00/62067 | 10/2000 |
| WO | 01/12171 | 2/2001 |
| WO | 01/12184 | 2/2001 |
| WO | 02/063954 | 8/2002 |
| WO | 02/064087 | 8/2002 |
| WO | 02/064147 | 8/2002 |
| WO | 02/102378 | 12/2002 |
| WO | 2005/020904 | 3/2005 |

OTHER PUBLICATIONS

Bashir, Z.I., et al., "N-methyl-D-aspartate Receptors and the Enhancement of Somatosensory Evoked Potentials in Penicillin Epileptogenesis in Rats," Physiological Society, 1987, 1 page.

Horn, E., et al., "Time Course of Interictal EEG Patterns Induced by a Penicillin Injection Into the Olfactory Cortex," Pharmacology Biochemistry & Behavior, vol. 40, 1991, pp. 351-357.

Home, A.L., et al., "The Pharmacology of Recombinant $GABA_A$ Receptors Containing Bovine $\alpha_1$, $\beta_1$, $\gamma_{2L}$ Sub-Units Stably Transfected Into Mouse Fibroblast L-Cells," Br. J. Pharmacol. vol. 107, 1992, pp. 732-737.

Kalueff, A.V., et al., "Penicillins and Their Derivatives: Antiulcer/Antistress Properties?," Neuropsychoharmacology, vol. 10, No. 3S, Part 2, 1994, 1 page.

Orwar, O., et al., "Increased Intra- and Extracellular Concentrations of γ-Glutamylglutamate and Related Dipeptides in the Ischemic Rat Striatum: Involvement of γ-Glutamyl Transpeptidase," Journal of Neurochemistry, vol. 63, 1994, pp. 1371-1376.

Serval, V., et al., "Competitive Inhibition of N-Acetylated-α-Linked Acidic Dipeptidase Activity by N-Acetyl-L-Aspartyl-β-Linked L-Glutamate," Journal of Neurochemistry, vol. 55, 1990, pp. 39-46.

Varga, V., et al., "Endogenous γ-L-Glutamyl and β-L-Aspartyl Peptides and Excitatory Aminoacidergic Neurotransmission in the Brain," Neuropeptides, vol. 27, 1994, pp. 19-26.

Nilsson, B. at al., "β-Lactam Analogues of Oxotremorine 3- and 4-Methyl-Substituted 2-Azetidinones,", J. Med. Chem., vol. 33, 1990, pp. 580-584.

Duijn, H.V. et al., "Action of Penicillin on Inhibitory Processes in the Cat's Cortex," Brain Res., vol. 53, 1973, pp. 470-476.

Meyer, H. et al., "Convulsant Actions of Penicillin: Effects on Inhibitory Mechanisms," vol. 53, 1973, 477-482.

Hochner, B. et al., "Penicillin Decreases Chloride Conductance in Crustacean Muscle: A Model for the Epileptic Neuron," Brain Res., vol. 107, 1976, pp. 85-103.

Chemomordik, A.B., Klin. Med. 1980, vol. 2, pp. 102-105.

Pickles, H.G., et al., "Antagonism by Penicillin of Gamma-Aminobutyric Acid Depolarization at Presynaptic Sites in Rat Olfactory Cortex and Cuneate Nucleus In Vitro," Neuropharmacology, vol. 19, 1980, pp. 35-38.

Sanger, D.J., "GABA and the Behavioral Effects of Anxiolytic Drugs," Life Sciences, vol. 36, 1985, pp. 1503-1513.

Chow, P. et al., "Convulsant Doses of Penicillin Shorten the Lifetime of GABA-Induced Channels in Cultured Central Neurones," Br. J. Pharmac., vol. 88, 1986, pp. 541-547.

Kaluev, A.V. et al., "Behavioral Effects of Penicillin in a Test for Anxiety in Rats," Bulletin of Experimental Biology and Medicine, vol. 120, No. 10, 1995, pp. 984-986.

Jackson, P.F. et al., "Design, Synthesis, and Biological Activty of a Potent Inhibitor of the Neuropeptidase N-Acetylated Alpha-Linked Acidic Dipeptidase," J. Med. Chem., vol. 39. No. 2, 1996, pp. 619-622.

Ungerer, A. et al., "Gamma-L-Glutamyl-L-Aspartate Induces Specific Deficits in Long-Term Memory and Inhibits [$^3$H]Glutamate Binding on Hippocampal Membranes," Brain Res., vol. 446, 1988, pp. 205-211.

Reynolds, E.F. "Martindale, The Extra Pharmocopoeia," Royal Pharmaceutical Society, London, col. 2-3, 1996, XP-002161510, p. 211.

Passani, et al., "N-acetylaspartylglutamate, N-acetylaspartate, and N-acetylated alpha-linked acidic dipeptidase in human brain and their alterations in Huntington and Alzheimer diseases," Molecular and Chemical Neuropathology, vol. 31, No. 2, 1997, pp. 97-118.

Macknin, M.L., "Behavioral changes after amoxicillin-clavulanate," letter, Pediatric Infectious Disease Journal, vol. 6, No. 9, 1987, pp. 873-874.

Tsai, G., et al., "Abnormal Excitatory Neurotransmitter Metabolism in Schizophrenic Brains", Archives of General Psychiatry, vol. 52, No. 10, 1995, pp. 829-836.

Pangalos, M. N., et al. "Isolation and expression of novel human glutamate carboxypeptidases with N-acetylated alpha-linked acidic dipeptidase and dipeptidyl peptidase IV activity," Journal of Biological Chemistry, vol. 274, No. 13, 1999, pp. 8470-8483.

Drummond, J. et al., "Synthesis of a Cognition Enhancing Beta-Lactam Fused Gamma-Lactam," Terahedron Ltrs, vol. 28, No. 44, 1987, pp. 5245-5248.

Kabanov, A. et al., "The neuroleptic activity of haloperidol increases after its solubilization in surfactant micelles," FEBS Letters, 07908, vol. 258, No. 2, 1989, pp. 343-345.

Iwamoto et al, English abstract from Japanese Patent JP360193982A from JPO database, 1985.

Zhang, W. et al., "The GCP II (NAALADase) Inhibitor GPI 5693 Prevents the Nerve Conduction Velocity Deficit and Morphological Changes Associated with Diabetes in the Type 1 Diabetic BB/WOR Rat," Society for Neuroscience, 2001, 31$^{st}$ Annual Meeting in San Diego, CA (Nov. 10-15, 2001).

Lockhart et al. "Cognition enhancing or neuroprotective compounds for the treatment of cognitive disorders: Why? When? Which?," Experimental Gerontology, vol. 38, No. 1-2, 2003, pp. 119-128.

Barco et al., "CREB, memory enhancement and the treatment of memory disorders: promises, pitfalls and prospects," Expert Opin. Ther. Targets, vol. 7, No. 1, 2003, pp. 101-114.

Knopman D.S. "Current pharmacotherapies for Alzheimer's disease," Geriatrics. vol. 53, (Supp 1) 1998, pp. S31-S34, abstract only.

Nichols R.L, et al., "Coagulophaty associated with extended-spectrum cephaolsporins in patients with serious infections," Antyimicrobial Agents and Chemotherapy, vol. 31, No. 2, 1987, pp. 281-285.

Montgomery, K.C., "The Relation Between Fear Induced by Novel Stimulation and Exploratory Behavior," J. Comp. Physiol. Psychol., vol. 48, 1955, pp. 254-260.

Kalueff, A.V., Derwent Drug File Abstract Online (STN-DRUFU), 1995, abstract No. 1996-33680.

"The Merck Manual of diagnosis and therapy", 16$^{th}$ edition 1992, p34.

Keyserling et al., "Clinical and Pharmacokinetic Evaluation of Parenteral Moxalactam in Infants and Children", Antimicrobial Agents and Chemotherapy, pp. 898-901, (1982).

Maithisen et al., "Clinical Evaluation of Moxalactam", Antimicrobial Agents and Chemotherapy, 21(5); pp. 780-786, (1982).

Modai et al.; "Moxalactam Penetration into Cerebrospinal Fluid in Patients with Bacterial Meningitis", 21(4); pp. 551-553, (1982).

Marier et al., "Moxalactam in the Therapy of Serious Infections", Antimicrobial Agents and Chemotherapy,, 21(4); pp. 650-654, (1982).

Goodman and Gilman's The Pharmacological Basis of Therapeutics, 8$^{th}$ edition, Pergamon press, 1990, p. 1068, col. 2.

Pfandler et al., "Synthesis and Biological Activity of Novel Penem Sulfoxides and Sulfones," Bioorganic and Medicinal Chemistry Letter, vol. 7, No. 17, pp. 2217-2222, 1997.

Chernomordik, A.B., "Method for the Therapeutic Use of Massive Doses of Penicillin," Klinicheskaia Meditsina, (1980) vol. 58, No. 11, English Summary, 5 pages.

* cited by examiner

EFFECT OF BETA – NAAG ON SEED FINDING

SEQUENCE LISTING

```
<160> NUMBER OF SEQ ID NOS: 6

<210> SEQ ID NO 1
<211> LENGTH: 4
<212> TYPE: PRT
<213> ORGANISM: Homo sapiens

<400> SEQUENCE: 1

Ser Thr Thr Lys
1

<210> SEQ ID NO 2
<211> LENGTH: 4
<212> TYPE: PRT
<213> ORGANISM: Homo sapiens

<400> SEQUENCE: 2

Glu Asn Lys Asp
1
```

```
<210> SEQ ID NO 3
<211> LENGTH: 4
<212> TYPE: PRT
<213> ORGANISM: Homo sapiens

<400> SEQUENCE: 3

Ser Thr Gln Lys
1

<210> SEQ ID NO 4
<211> LENGTH: 4
<212> TYPE: PRT
<213> ORGANISM: Homo sapiens

<400> SEQUENCE: 4

Glu Arg Gly Val
1

<210> SEQ ID NO 5
<211> LENGTH: 4
<212> TYPE: PRT
<213> ORGANISM: Homo sapiens

<400> SEQUENCE: 5

Asn Ser Arg Lys
1

<210> SEQ ID NO 6
<211> LENGTH: 4
<212> TYPE: PRT
<213> ORGANISM: Homo sapiens

<400> SEQUENCE: 6

Glu Arg Ser Ile
1
```

NEUROTHERAPEUTIC COMPOSITIONS AND METHOD

CROSS REFERENCE TO RELATED APPLICATION

This application is a continuation of U.S. patent application Ser. No. 10/658,667, filed Sep. 9, 2003, which is a divisional application of U.S. patent application Ser. No. 09/640,363, filed Aug. 16, 2000, which claims priority to U.S. Provisional Application Ser. Nos. 60/149,115, filed Aug. 16, 1999; 60/172,452, filed Dec. 17, 1999; 60/176,570, filed Jan. 18, 2000; and 60/194,534, filed Apr. 4, 2000.

FIELD OF INVENTION

This invention relates to a novel mechanism of neuropsychiatric intervention. More particularly, this invention is directed to pharmaceutical formulations and methods for treatment of a variety of neurological disease states, including cognitive and behavioral disorders.

BACKGROUND AND SUMMARY OF THE INVENTION

The pharmaceutical industry has directed extensive research and development efforts toward discovery and commercialization of drugs for treatment of neurological disorders. Such disorders typically derive from chemical imbalances in the brain. Overproduction or underproduction of pertinent neurochemical species and/or receptor dysfunction has been identified with many disease states recognized by neurologists, psychiatrists, psychologists and other medical practitioners skilled in the diagnosis and treatment of mental disease. Most of the discovery effort for new neurologically active drugs has been based on the study of agonist/antagonist drug interaction with one or more of the numerous receptors in the brain and/or their respective receptor ligands.

The present invention provides a novel approach to drug intervention in the treatment of a wide variety of neurologic disease states and other disease states or clinical conditions of related etiology. It is based in part on the discovery that β-lactam containing compounds known for their activity as inhibitors of bacterial peptidases or proteases, particularly transpeptidases and/or carboxypeptidases, are also potent inhibitors of certain mammalian neuro-peptidases, including N-acetylated-α-linked acidic peptidases (NAALADases), several of which have been identified/characterized in the literature [Pangalos et al., *J. Biol. Chem.*, 1999, 274, No. 13, 8470-8783]. The present invention is also based in part on the discovery that neurogenic NAALADases can be targeted with NAALADase inhibitors to effect significant behavioral modification and enhanced cognitive performance. Preliminary studies have confirmed that one or more neurogenic proteases, now believed to be NAALADases and related peptidases and transferases, capable of recognizing and transforming certain neuropeptides (e.g., N-acetyl-L-aspartyl-L-glutamate) play a significant if not dominant role at the neurochemical level of brain function and concomitantly have a substantial impact on patient behavior and cognitive performance. It has been previously reported that certain glutamate analogs acting as NAALADase inhibitors can be used to treat prostate disease and glutamate abnormalities associated with certain nervous tissue insult. It has now been determined that NAALADase inhibitors, including particularly certain β-lactam-containing bacterial peptidase and β-lactamase inhibitors capable of blood-brain barrier transport, can function in the brain at very low concentrations as potent neuroactive drug substances to reduce the symptoms of a wide variety of neurological disorders characterized by behavioral aberration or sensory/cognitive dysfunction. Significantly, such bacterial enzyme inhibitors are believed to be effective inhibitors of NAALADase and related neurogenic peptidases, at concentrations below those concentrations known to be required for clinically effective bacterial enzyme inhibition. Thus it is expected that such compounds can also be used effectively for treating prostate disease and the disease states associated with nervous tissue insult previously described as responsive to treatment with other NAALADase inhibitors.

Accordingly, one embodiment of the present invention is directed to a method for treatment of cognitive and behavioral disorders in warm-blooded vertebrates by administering compounds known for their activity as bacterial protease or peptidase inhibitors, which compounds, when present at effective concentrations in the brain, have now been determined to be capable of inhibiting or otherwise modulating the activity of one or more neurogenic NAALADases and related neurogenic enzymes.

In a related embodiment there is provided method for treatment of cognitive and behavioral disorders in a patient in need of such treatment. The method comprises the step of inhibiting neurogenic peptidases, including NAALADase and related neurogenic enzymes. In one embodiment such neuropeptidase inhibition is effected by administering an effective amount of a β-lactam compound recognized for its capacity to bind to and inhibit a bacterial enzyme, for example, a β-lactamase or a bacterial protease involved in bacterial cell wall synthesis. Such bacterial proteases are known in the art as "penicillin binding proteins." In another embodiment of the present invention, the method is effected by administration of art-recognized NAALADase inhibitors, including particularly certain deaminoglutamate analogues and N-substituted glutamate derivatives. Effective inhibition of such neuro-peptidase activity in warm-blooded vertebrates has been found to produce marked enhancement in cognitive performance and behavioral management.

Exemplary of cognitive and behavioral disorders susceptible to treatment in accordance with this invention include aggressive disorder, obsessive compulsive disorder, anxiety, depression, ADHD, and memory impairment. Animal data suggest that the method and formulation of this invention have potential as an antiaggressive agent to control impulsivity and violence in autism, Tourette's syndrome, mental retardation, psychosis, mania, senile dementia and individuals with personality disorders and history of inappropriate aggression. Clinic applications extend to the treatment of children with ADHD and conduct disorder, as an anxiolytic, and as a cognition enhancer for the geriatric population to improve learning and memory and to ameliorate disorientation.

In another embodiment of this invention there is provided a method of treating a patient afflicted with a condition, or disposed to development of a condition, characterized at least in part by abnormal extracellular concentration of glutamate in the brain or other nervous tissue. The method comprises the step of administering to the patient in effective amounts of a compound capable of inhibiting the activity of a penicillin-binding protein of bacterial origin. The composition is administered in an amount effective to prevent or alleviate the symptoms of such condition. Thus, for example, localized high glutamate concentrations in the brain have been reported in stroke victims and victims of other brain trauma. More recently high glutamate concentrations in the brain and peripheral nerve tissue have been reported to be associated with multiple sclerosis.

In still another embodiment of the invention there is provided a method for treating prostate disease selected from prostate cancer and benign prostate hyperplasia in a human patient. The method comprises the step of administering to the patient a composition comprising a compound capable of inhibiting the activity of a penicillin-binding protein of bacterial origin. The compound is administered in an amount effective to retard the progress of the disease or to reduce the symptoms of the disease.

One group of compounds for use in accordance with this invention are β-lactam compounds, i.e., compounds having a β-lactam ring system, including particularly β-lactam antibiotics such as penicillins, cephalosporins and analogues thereof. Further, the peptide Ala-D-γ-Glu-Lys-D-Ala-D-Ala (believed to serve as a substrate for NAALADase) has been found effective as a peptidase inhibitor useful for behavior modification and cognitive enhancement in accordance with the invention. Non-β-lactam NAALADase inhibitors have been reported in the patent and non-patent literature. See, e.g., U.S. Pat. Nos. 5,795,877; 5,804,602; 5,968,915; 5,902,817; 5,962,521, 5,863,536, and 6,017,903, the specifications of which are specifically incorporated herein by reference for their teaching of such NAALADase inhibitors and the use generally of such NAALADase inhibitors for treatment of certain disease states responsive to NAALADase inhibition therapy. Other compounds capable of use in accordance with this invention can be identified using molecular modeling studies. The antibiotic compounds for use in this invention can be administered in combination with one or more of other enzyme inhibitors, for example, effective amounts of a β-lactamase inhibitor (where the active compound is a β-lactam compound) or another NAALADase inhibitor or a P-glycoprotein efflux inhibitor to enhance brain levels of the active compound. The method and formulation embodiments of the invention find use in both human health and veterinary applications, e.g., in canine, feline and equine species.

In one embodiment of the present invention a warm-blooded vertebrate, most typically a human patient, affected by a neurologic disease state characterized by cognitive or behavioral abnormalities is treated with a 1-oxa-1-dethia cephalosporin, more preferably a 7-methoxy-1-oxa-1-dethia cephalosporin, optionally as an active ester derivative in an orally (including buccal or sublingual administration) or a parenterally administered formulation. In one embodiment, the peptidase inhibitor is moxalactam, [7-β-[2-carboxy-2-(4-hydroxyphenyl)acetamido]-7α-methoxy-3-[[(1-methyl-1H-tetrazol-5-yl)thio]methyl]-1-oxa-1-dethia-3-cephem-4-carboxylic acid], described and claimed with related compounds, including their orally absorbed active ester derivatives, in U.S. Pat. No. 4,323,567, the specification of which is expressly incorporated herein by reference. Moxalactam has been found to exhibit significant dose responsive neuroactivity when administered parenterally at least at about 50 µg/kg of body weight.

In another embodiment of the present invention there is provided a pharmaceutical formulation for treatment with consequent reduction of symptoms of behavioral or cognitive disorders in patients in need of such treatment. The formulation comprises a compound characterized by its affinity to bacteria derived penicillin-binding proteins. In one embodiment the compound is capable of binding to and inhibiting the function of a bacterial protease known to exhibit its proteolytic activity on a peptidoglycan substrate comprising the C-terminal peptide sequence acyl-D-alanyl-D-alanine. In another embodiment the compound is capable of binding to β-lactamase, another bacterial protein capable of binding to penicillin, and inhibiting the function of that enzyme. The amount of the inhibitor used in the formulation is that determined to be effective to inhibit the activity of endogenous NAALADase. In one embodiment the amount is effective to inhibit NAALADase in the brain at a level sufficient to modulate cognitive and behavioral characteristics. In that later embodiment the level of activity exhibited by the NAALADase inhibitor in the present method is not only dependent on its affinity to penicillin-binding proteins and to NAALADase, it is also particularly dependent on ability of the inhibitor compound to cross the blood brain barrier to achieve levels in the brain effective to modify patient behavior and/or cognitive performance.

In one embodiment of the invention the pharmaceutical formulation comprises a β-lactam containing compound selected from the group consisting of penicillin, cephalosporins, β-lactam containing analogues thereof, including β-lactamase inhibitors, and a pharmaceutical carrier for such β-lactam containing compound. In cases where the β-lactam compound is, for example, a commercially available antibiotic, the amount of β-lactam compound in said formulation is less than that required to produce, upon administration by the commercially detailed mode of administration, clinically effective antibiotic blood levels of the compound. Yet the reduced dosage levels of said antibiotics can be effective, assuming reasonable blood-brain barrier transport properties, to produce brain and CSF levels of the compound sufficient to inhibit neurogenic protease activity in the brain and modify cognitive and behavioral characteristics. Such formulations can optionally include, in addition, effective amounts of one or more of a β-lactamase inhibitor and a P-glycoprotein efflux pump inhibitor or another compound capable of inhibiting the activity of NAALADase and related neurogenic enzymes. While the formulations of this invention can be prepared specifically for any art-recognized mode of administration capable of achieving threshold minimum protease inhibiting concentrations in the brain, they are typically formulated for parenteral or oral administration, optionally in the form of prolonged release or "drug depot" type formulations well known in the art.

BRIEF DESCRIPTION OF THE DRAWINGS

FIGS. 15 and 16 are graphic illustrations of the effect of intracerebrally administered peptidoglycan-precursor protein on offensive aggression and olfactory discrimination in hamsters.

DETAILED DESCRIPTION OF THE INVENTION

Figure 1A:
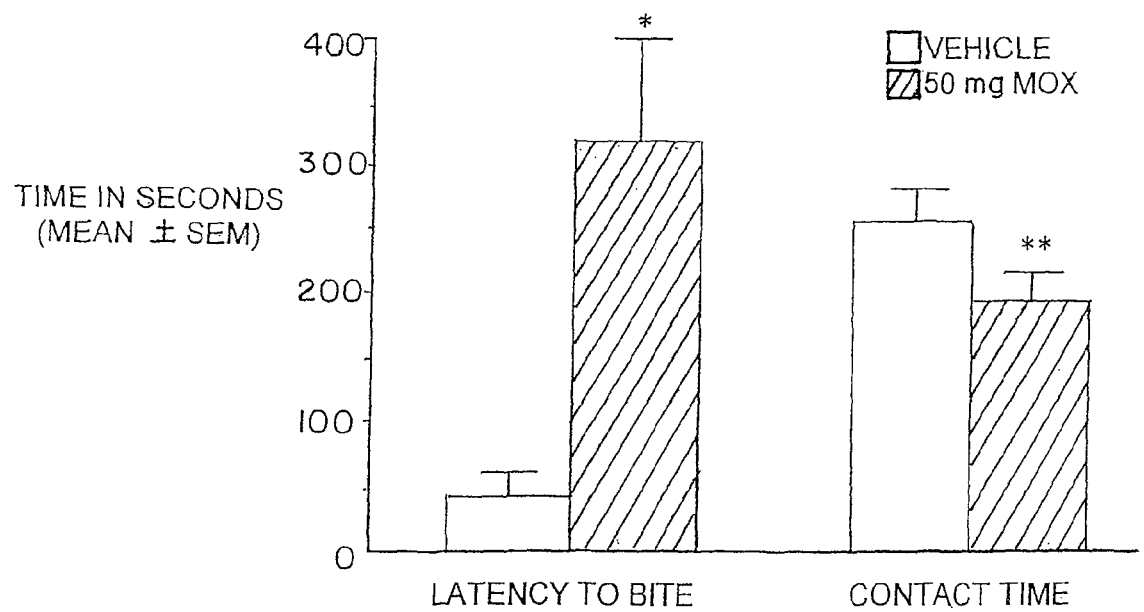
FIGS. 1-42 are graphic representations of data gathered in the conduct of testing of moxalactam, other β-lactam antibiotics, clavulanic acid, and other neuroactive compounds in various animal models accepted in the art for detection of activity against offensive aggression (FIGS. 1-4, 9-14, 24, 29, 31 and 32), general motor activity, olfactory discrimination (FIG. 5), sexual activity (FIG. 6), anxiolytic activity (FIGS. 7, 25, 26, 28, 37 and 40), and spatial memory (FIGS. 8 and 29-36).

The present invention and the various embodiments described and claimed herein derive, in part, from the discoveries that compounds capable of binding to and inhibiting enzyme activity of penicillin-binding proteins of bacterial origin are also potent inhibitors of N-acetylated-α-linked acid dipeptidase (NAALADase) activity and possibly other related enzymes in the brain, and that when administered to provide effective threshold NAALADase inhibitory concentrations of same in the brain, NAALADase inhibitors exhibit clinically significant neuroactivity evidenced in part by behavioral modification and enhanced cognition and function.

In one embodiment the NAALADase inhibitors effective for use in accordance with the present invention are characterized by their capacity to inhibit a bacterial protease exhibiting selective proteolytic activity on a protein or peptide substrate comprising acyl-D-alanyl-D-alanine. Alternatively stated, effective NAALADase inhibitors for use in treatment of behavioral and cognitive disorders in accordance with one embodiment of this invention, can be characterized by their selective affinity (by associative and/or covalent binding) to penicillin-binding proteins; such compounds include particularly β-lactam antibiotics such as penicillins, cephalosporins and analogues thereof. Based on animal tests to date, such bacterial protease inhibitors appear to function at subclinical-antibiotic levels in the brain to inhibit neuropeptidase activity which can function in neurochemical mediation of behavior and cognitive performance. Effective inhibition of neuropeptidase activity with concomitant mediation of behavior and cognitive performance has also been effected by administration of a β-lactamase inhibitor, clavulanic acid, a β-lactam containing compound having no clinically significant antibiotic activity. It is surmised that inhibition of such neuropeptidase (e.g., NAALADase) activity allows modulation of the concentration and/or function of one or more neurotransmitters or neuromodulators with concomitant improvement in neurological function evidenced by enhancement of cognitive performance and attenuation of aberrant behavioral phenotypes. In one example of this invention, moxalactam given i.p. at 50 micrograms/kg inhibits aggression in hamster, enhances spatial learning in rats, and acts as an anxiolytic in rats. Clavulanic acid has shown similar activity when administered i.p. at less than 1 microgram/kg.

Historically, those knowledgeable in the field of beta lactam antibiotics understand that the mode of action as antibacterial agents is by inhibiting cell wall synthesis by acting as a substrate for penicillin-binding protein (PBP); the term PBP has been extended to include binding to all beta lactams including cephalosporins. More recently, investigators have been able to clone and sequence these PBP's as well as crystallize the enzymes and determine active site motifs (see P. Palomeque et al., *J. Biochem.*, 279, 223-230, 1991). Based on this data, the four putative binding sites for PBP have been designated active site I, II, III and IV. The active sites, sequence location and amino acid (AA) sequence are as follows:

```
Active site I:
                                       (SEQ ID NO: 1)
35 AA's downstream from N-terminus: STTK Active site II:
                                       (SEQ ID NO: 1)
57 AA's downstream from STTK motif: SGC, SGN, or SAN Active site III:
111 AA's downstream from SGC motif: KTG Active site IV:
                                       (SEQ ID NO: 2)
41 AA's downstream from SGC motif: ENKD
```

Pursuant to identifying an enzyme system in the brain that moxalactam would inhibit in a similar manner to PBP, it was discovered that a glutamyl carboxypeptidase enzyme known as N-acetyl-α-linked acidic dipeptidase (NAALADase) (See M. N. Pangalos et al., *J. Bio. Chem.*, 264, 8470-8483, 1999) has an almost perfect overlap of the putative active sites of PBP. This enzyme system is responsible for regulating the glutamatergic neurotransmission pathways, the effects of which would be expressed in such behavioral outcomes as aggression, memory/cognition, and anxiety. As a result of the almost perfect overlap of the putative active sites of PBP and the conserved sequences in human and rat NAALADase, it is believed that moxalactam and other β-lactam compounds mediate behavioral effects by inhibiting NAALADase at low concentrations. This is based on the following overlap sequence similarity between PBP and NAALADase I, one of several known NAALADase species, as shown below:

```
Active site I:
                                       (SEQ ID NO: 1)
PBP: 35 AA's downstream from N-terminus: STTK (SEQ ID NO: 3)
NAALADase: 38 AA's downstream from N-terminus:

STQK

Active site II:
                                       (SEQ ID NO: 1)
PBP: 57 AA's downstream from STTK motif: SGC, SGN, or SAN (SEQ ID NO: 3)
NAALADase: 59 AA's downstream from STQK motif: SFG Active site III:
PBP: 111 AA's downstream from SGC motif: KTG NAALADase: 110 AA's downstream from SFG motif: KLG Active site IV:
                                       (SEQ ID NO: 2)
PBP: 41 AA's downstream from SGC motif: ENKD (SEQ ID NO: 4)
NAALADase: 41 AA's downstream from SFG motif: ERGV
```

Since the beta-lactams provide their inhibition of PBP transpeptidation of bacterial cell wall by binding to these four active sites, one can infer that the conserved similarity in active site sequences and location would confer similar binding properties of moxalactam and other β-lactam compounds to NAALADase and possibly other neurogenic enzymes having sequences overlapping with the four active binding site motif. That discovery coupled with observation of the significant behavioral modification effects deriving from administration of very low doses of certain penicillin protein binding compounds has provided insight into a novel approach to the prevention and treatment of disease states characterized by neurological dysfunction.

The unique neurological activity profiles of the two β-lactam compounds that have been studied most extensively to date, moxalactam and clavulanic acid, suggest that those compounds exhibit activity on multiple neurogenic enzyme targets, including NAALADase and structurally related enzymes, particularly those that might share the four active binding site motif common to both PBP and NAALADase. To identify other putative neurogenic targets for the behavioral and cognitive activities discovered for moxalactam and clavulanic acid, the sequence for NAALADase II was used to search the human genome database (NCBI-BLAST). Seven human gene sequences were identified that have significant homology with NAALADase II and that encode for the four active site motif:

1) >dbj/AP001769.2/AP001769 *Homo sapiens* chromosome 11 clone RP11-240F8 map 11q14
Active site I:
(SEQ ID NO: 1)
PBP: 35 AA's downstream from N-terminus: . . . STTK (SEQ ID NO: 3)
NAALADase: 38 AA's downstream from N-terminus: STQK (SEQ ID NO: 5)
>dbj/AP001769: NSRK Active site II:
(SEQ ID NO: 1)
PBP: 57 AA's downstream from STTK motif: . . . SGC, SGN, or SAN (SEQ ID NO: 3)
NAALADase: 59 AA's downstream from STQK motif: SFG >dbj/AP001769: SFG Active site III:
PBP: 111 AA's downstream from SGC motif: . . . KTG NAALADase: 110 AA's downstream from SFG motif: KLG >dbj/AP001769: KLG Active site IV:
(SEQ ID NO: 2)
PBP: 41 AA's downstream from SGC motif: . . . ENKD (SEQ ID NO: 4)
NAALADase: 41 AA's downstream from SFG motif: ERGV (SEQ ID NO: 6)
>dbj/AP001769: ERSI 2) >dbj|AP000827.2|AP000827 *Homo sapiens* chromosome 11 clone RP.
Active site I:
(SEQ ID NO: 1)
PBP: 35 AA's downstream from N-terminus: . . . STTK (SEQ ID NO: 3)
NAALADase: 38 AA's downstream from N-terminus: STQK (SEQ ID NO: 5)
>dbj|AP000827.2: NSRK Active site II:
(SEQ ID NO: 1)
PBP: 57 AA's downstream from STTK motif: SGC, SGN, or SAN (SEQ ID NO: 3)
NAALADase: 59 AA's downstream from STQK motif: SFG >dbj|AP000827.2: SFG Active site III:
PBP: 111 AA's downstream from SGC motif: . . . KTG NAALADase: 110 AA's downstream from SFG motif: KLG >dbj|AP000827.2: KLG Active site IV:
(SEQ ID NO: 2)
PBP: 41 AA's downstream from SGC motif: . . . ENKD (SEQ ID NO: 4)
NAALADase: 41 AA's downstream from SFG motif: ERGV (SEQ ID NO: 6)
>dbj|AP000827.2: ERSI 3) >dbj|AP000648.2|AP000648 *Homo sapiens* chromosome 11 clone CM.
Active site I:
(SEQ ID NO: 1)
PBP: 35 AA's downstream from N-terminus: . . . STTK (SEQ ID NO: 3)
NAALADase: 38 AA's downstream from N-terminus: STQK (SEQ ID NO: 5)
dbj|AP000648.2: NSRK Active site II:
(SEQ ID NO: 1)
PBP: 57 AA's downstream from STTK motif: SGC, SGN, or SAN (SEQ ID NO: 3)
NAALADase: 59 AA's downstream from STQK motif: SFG >dbj|AP000648.2: SFG Active site III:
PBP:111 AA's downstream from SGC motif: . . . KTG NAALADase: 110 AA's downstream from SFG motif: KLG >dbj|AP000648.2: KLG Active site IV:
(SEQ ID NO: 2)
PBP:41 AA's downstream from SGC motif: . . . ENKD (SEQ ID NO: 4)
NAALADase: 41 AA's downstream from SFG motif: ERGV (SEQ ID NO: 6)
>dbj|AP000648.2: ERSI 4) >gb|AC074003.2|AC074003 *Homo sapiens* chromosome 2 clone RP11.
Active site I:
(SEQ ID NO: 1)
PBP: 35 AA's downstream from N-terminus: . . . STTK (SEQ ID NO: 3)
NAALADase: 38 AA's downstream from N-terminus: STQK gb|AC074003.2|AC074003: STQ- -continued Active site II:
PBP: 57 AA's downstream from STTK (SEQ ID NO: 1)

motif: SGC, SGN, or SAN

NAALADase: 59 AA's downstream from STQK (SEQ ID NO: 3)

motif: SFG gb|AC074003.2|AC074003: SFG

Active site III:
PBP: 111 AA's downstream from SGC motif: . . . KTG

NAALADase: 110 AA's downstream from SFG motif: KLG gb|AC074003.2|AC074003: KLG

Active site IV:
PBP: 41 AA's downstream from SGC motif: . . . ENKD (SEQ ID NO: 2)

NAALADase: 41 AA's downstream from SFG motif: ERGV (SEQ ID NO: 4)

gb|AC074003.2|AC074003 ER GV

5) >emb|AL162372.6|AL162372 Homo sapiens chromosome 13 clone RP.
Active site I:
PBP: 35 AA's downstream from N-terminus: . . . (SEQ ID NO: 1)

STTK

NAALADase: 38 AA's downstream from N-terminus: (SEQ ID NO: 3)

STQK emb|AL162372.6: STQ-

Active site II:
PBP: 57 AA's downstream from STTK (SEQ ID NO: 1)

motif: SGC, SGN, or SAN

NAALADase: 59 AA's downstream from STQK (SEQ ID NO: 3)

motif: SFG emb|AL162372.6: SFG

Active site III:
PBP: 111 AA's downstream from SGC motif: . . . KTG

NAALADase: 110 AA's downstream from SFG motif: KLG emb|AL162372.6: KLG

Active site IV:
PBP: 41 AA's downstream from SGG motif: . . . ENKD (SEQ ID NO: 2)

NAALADase: 41 AA's downstream from SFG motif: ERGV (SEQ ID NO: 4)

emb|AL162372.6 ERGV 6) gb|AC024234.5|AC024234 Homo sapiens chromosome 11 clone RP1.

-continued

Active site I:
PBP: 35 AA's downstream from N-terminus: . . . (SEQ ID NO: 1)

STTK

NAALADase: 38 AA's downstream from N-terminus: (SEQ ID NO: 3)

STQK gb|AC024234.5|AC024234: STQ-

Active site II:
PBP: 57 AA's downstream from STTK (SEQ ID NO: 1)

motif: SGC, SGN, or SAN

NAALADase: 59 AA's downstream from STQK (SEQ ID NO: 3)

motif: SFG gb|AC024234.5|AC024234: SFG

Active site III:
PBP: 111 AA's downstream from SGC motif: . . . KTG

NAALADase: 110 AA's downstream from SFG motif: KLG gb|AC024234.5|AC024234: KLG

Active site IV:
PBP: 41 AA's downstream from SGC motif: . . . ENKD (SEQ ID NO: 2)

NAALADase: 41 AA's downstream from SFG motif: ERGV (SEQ ID NO: 4)

gb|AC024234.5|AC024234 ER GV 7) dbj|AP002369.1|AP002369 Homo sapiens chromosome 11 clone RP . . .

Active site I:
PBP: 35 AA's downstream from N-terminus: . . . (SEQ ID NO: 1)

STTK

NAALADase: 38 AA's downstream from N-terminus: (SEQ ID NO: 3)

STQK dbj|AP002369.1: STQ-

Active site II:
PBP: 57 AA's downstream from STTK (SEQ ID NO: 1)

motif: SGC, SGN, or SAN

NAALADase: 59 AA's downstream from STQK (SEQ ID NO: 3)

motif: SFG dbj|AP002369.1: SFG

Active site III:
PBP: 111 AA's downstream from SGC motif: KTG

NAALADase: 110 AA's downstream from SFG motif: KLG dbj|AP002369.1: KLG

```
                         -continued
Active site IV:
                                                   (SEQ ID NO: 2)
PBP:  41 AA's downstream from SGC motif:   . . . ENKD (SEQ ID NO: 4)
NAALADase: 41 AA's downstream from SFG motif: ERGV dbj|AP002369.1 ERGV
```

The encoded protein of each of those gene sequences expressed in the brain are probable targets for behavioral and cognitive activity by β-lactams and other NAALADase inhibitors. Thus in accordance with one aspect of the invention there is provided a method for modifying behavior and/or cognition comprising the step of inhibiting the biological activity of the non-NAALADase protein(s) expressed by one or more of the above-identified gene sequences, by administering an effective amount of a β-lactam compound or other compound capable of NAALADase inhibition.

In one embodiment the NAALADase inhibitors effective for use in the various pharmaceutical formulation and method embodiments of this invention, generally speaking, are compounds which exhibit detectable selective affinity for art recognized penicillin-binding proteins, including particularly β-lactam-containing compounds (hereinafter "β-lactam compounds") such as penicillins and cephalosporins and analogues thereof, certain β-lactamase inhibitors, and peptides comprising the amino acid sequence Ala-D-γ-Glu-Lys-D-Ala-D-Ala. Among such NAALADase inhibiting compounds, those preferred for use in accordance with this invention are compounds that also exhibit good blood brain barrier transport properties evidenced by favorable cerebral spinal fluid (CSF)/brain:serum concentration ratios. Further, it will be appreciated that other art-recognized NAALADase inhibitors can be used alone or in combination with penicillin protein-binding compounds for treatment and prevention of behavioral and/or cognitive disorders.

In the embodiments of the invention directed to pharmaceutical formulations for use in inhibition of neurogenic NAALADase to modify behavior and/or improve cognitive function, the β-lactam compounds or other NAALADase inhibiting compounds including peptides or analogues of such compounds are typically formulated in unit dosage form optionally in combination with, or as covalent conjugates of, other compounds or molecular entities, respectively, known to enhance drug transport across the blood brain barrier. Such drug formulation/conjugation techniques are described and claimed in the following listed U.S. Patents, the specifications of which patents are expressly incorporated herein by reference: U.S. Pat. Nos. 5,624,894; 5,672,683; 5,525,727; 5,413,996; 5,296,483; 5,187,158; 5,177,064; 5,082,853; 5,008,257; 4,933,438; 4,900,837; 4,880,921; 4,824,850; 4,771,059; and 4,540,564.

Enhanced concentrations of drug substances, including NAALADase inhibitors in the brain, can also be achieved by co-administration with P-glycoprotein efflux inhibitors such as those described in U.S. Pat. Nos. 5,889,007; 5,874,434; 5,654,304; 5,620,855; 5,643,909; and 5,591,715, the specifications of which patents are expressly incorporated herein by reference. Alternatively, β-lactam antibiotic compounds useful in accordance with this invention, including penicillins, cephalosporins, penems, 1-oxa-1-dethia cephems, clavams, clavems, azetidinones, carbapenams, carbapenems, and carbacephems, can be administered alone or in combination with art-recognized β-lactamase inhibitors, which themselves may or may not be β-lactam compounds or compounds capable of exhibiting selective affinity for penicillin-binding proteins. Examples of β-lactamase inhibitors which can be used alone or in combination with other neuropeptidase inhibitors useful in accordance with this invention for treatment and/or prevention of cognitive or behavioral disorders are other β-lactam compounds which may or may not exhibit independent clinically significant antibacterial activity, such as clavulanic acid and thienamycin and analogs thereof, sulbactam, tazobactam, sultamicillin, and aztreonam and other monolactams.

The patent and non-patent literature is replete with references describing β-lactam antibiotics, their preparation, their characterization, their formulation and their mode of action. β-Lactam antibiotics are known to exhibit their antibiotic activity by interfering with one or more biological pathways involved in bacteria cell wall synthesis; more particularly, they inhibit carboxypeptidase and/or transpeptidase (or protease) activity involved in cross-linking of the peptidoglycan chains used as building blocks for cell wall synthesis. β-Lactam antibiotics are thus believed to act as inhibitors of carboxypeptidases or transpeptidases by their covalent, and by some reports, noncovalent associative bonding, to one or more of a group of such bacterial enzymes generally termed penicillin binding proteins (PBP's). Such enzymes serve to complete bacteria cell wall synthesis by cross linking peptidoglycan chains.

A similar peptidase-substrate interaction/inhibition is now suggested in accordance with this invention as a significant neurochemical pathway involved in brain function pivotal to cognitive performance and behavioral phenotype. Such a neurochemical mechanism is suggested too by the discovery that delivery of effective amounts of the peptide Ala-D-γ-Glu-Lys-D-alanyl-D-alanine directly into the brain produced the same modified behavioral characteristics as that achieved by comparable concentrations of β-lactam compounds in the brain. The peptide appears to serve as a substitute substrate for (and thus serve to inhibit the activity thereof) one or more neurogenic peptidases (e.g., NAALADases) that normally exhibit their activity on peptidic neurotransmitters or neuromodulators, i.e., NAAD, in the ordinary course of certain neurochemical processes that mediate cognitive performance and behavioral phenotype.

Based on animal tests to date it is believed that the general classes of behavioral disorders can be prevented or treated in accordance with this invention by administration of effective amounts of NAALADase inhibitors include aggressive disorder, obsessive-compulsive disorder, anxiety, depression, and attention deficit hyperactivity disease (ADHD). Thus in one embodiment of the invention a NAALADase inhibitor selected from those capable of binding to penicillin-binding protein, e.g., a β-lactam antibiotic or β-lactamase inhibitor, and/or those exhibiting inhibition of selective proteolytic activity on a bacterial protein or peptide substrate comprising the C-terminal amino acid sequence acyl-D-alanyl-D-alanine, or other NAALADase inhibitor, is administered as an anti-aggressive agent to control impulsivity and violence in a patient afflicted with autism, Tourette's Syndrome, mental retardation, psychosis, mania, senile dementia or that in a patient with personality disorder and history of inappropriate aggression. In another embodiment a deaminoglutamate analog or an N-substituted glutamate derivative is administered in an amount effective to control impulsivity and violence in patients effected with such disease states.

Other neurological disease states which can be treated in accordance with the present invention include depression, including major depression (single episode, recurrent, melancholic), atypical, dysthmia, subsyndromal, agitated, retarded, co-morbid with cancer, diabetes, or post-myocardial infarction, involutional, bipolar disorder, psychotic depression, endogenous and reactive, obsessive-compulsive disorder, or bulimia. In addition, NAALADase inhibitors can be used to treat patients suffering from pain (given alone or in combination with morphine, codeine, or dextropropoxyphene), obsessive-compulsive personality disorder, post-traumatic stress disorder, hypertension, atherosclerosis, anxiety, anorexia nervosa, panic, social phobia, stuttering, sleep disorders, chronic fatigue, cognition deficit associated with Alzheimer's disease, alcohol abuse, appetite disorders, weight loss, agoraphobia, improving memory, amnesia, smoking cessation, nicotine withdrawal syndrome symptoms, disturbances of mood and/or appetite associated with pre-menstrual syndrome, depressed mood and/or carbohydrate craving associated with pre-menstrual syndrome, disturbances of mood, disturbances of appetite or disturbances which contribute to recidivism associated with nicotine withdrawal, circadian rhythm disorder, borderline personality disorder, hypochondriasis, pre-menstrual syndrome (PMS), late luteal phase dysphoric disorder, pre-menstrual dysphoric disorder, trichotillomania, symptoms following discontinuation of other antidepressants, aggressive/intermittent explosive disorder, compulsive gambling, compulsive spending, compulsive sex, psychoactive substance use disorder, sexual disorder, schizophrenia, premature ejaculation, or psychiatric symptoms selected from stress, worry, anger, rejection sensitivity, and lack of mental or physical energy.

Other examples of pathologic, psychologic conditions which may be treated in accordance with this invention include, but are not limited to: Moderate Mental Retardation (318.00), Severe Mental Retardation (318.10), Profound Mental Retardation (318.20), Unspecified Mental Retardation (319.00), Autistic Disorder (299.00), Pervasive Development Disorder NOS (299.80), Attention-Deficit Hyperactivity Disorder (314.01), Conduct Disorder, Group Type (312.20), Conduct Disorder, Solitary Aggressive Type (312.00), Conduct Disorder, Undifferentiated Type (312.90), Tourette's Disorder (307.23), Chronic Motor or Vocal Tic Disorder (307.22), Transient Tic Disorder (307.21), Tic Disorder NOS (307.20), Primary Degenerative Dementia of the Alzheimer Type, Senile Onset, Uncomplicated (290.00), Primary Degenerative Dementia of The Alzheimer Type, Senile Onset, with Delirium (290.30), Primary Degenerative Dementia of the Alzheimer Type, Senile Onset, with Delusions (390.20), Primary Degenerative Dementia of the Alzheimer Type, Senile Onset, with Depression (290.21), Primary Degenerative Dementia of the Alzheimer Type, Presenile Onset, Uncomplicated (290.10), Primary Degenerative Dementia of the Alzheimer Type, Presenile Onset, with Delirium (290.11), Primary Degenerative Dementia of the Alzheimer Type, Presenile Onset, with Delusions (290.12), Primary Degenerative Dementia of the Alzheimer Type, Presenile Onset, with Depression (290.13), Multi-infarct dementia, Uncomplicated (290.40), Multi-infarct dementia, with Delirium (290.41), Multi-infarct Dementia, with Delusions (290.42), Multi-infarct Dementia, with Depression (290.4 3), Senile Dementia NOS (290.10), Presenile Dementia NOS (290.10), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delusional Disorder (292.11), *Cannabis* Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Hood Disorder (292.84), Phencyclidine (PCP) or Similarly Acting Arylcyclohexylamine Organic Mental Disorder NOS (292.90), Other or unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive Substance Hallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.81), Organic Mood Disorder (293.83), Organic Anxiety Disorder (294.80), Organic Personality Disorder (310.10), Organic Mental Disorder (29.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39).

Additional examples of pathologic psychological conditions which may be treated using the β-lactam containing protease inhibitors as described in this invention include Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorganized, Unspecified (295.10), Schizophrenia, Paranoid, Subchronic 295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, Chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, unspecified (295.60), Delusional (Paranoid) Disorder (297.10), Brief Reactive Psychosis (298.80), Schizophreniform Disorder (295.40), Schizoaffective Disorder (295.70), induced Psychotic Disorder (297.30), Psychotic Disorder NOS (Atypical Psychosis) (298.90), Bipolar Disorder, Mixed, Severe, without Psychotic Features (296.63), Bipolar Disorder, Manic, Severe, without Psychotic Features (296.43), Bipolar Disorder, Depressed, Severe, without Psychotic Features (296.53), Bipolar Disorder, Mixed, with Psychotic Features (296.64) Bipolar Disorder, Manic, with Psychotic Features (296.44), Bipolar Disorder, Depressed, with Psychotic Features (296.54), Bipolar Disorder NOS (296.70), Major Depression, Single Episode, with Psychotic Features (296.24), Major Depression, Recurrent with Psychotic Features (296.34) Personality Disorders, Paranoid (301.00), Personality Disorders, Schizoid (301.20), Personality Disorders, Schizotypal (301.22), Personality Disorders, Antisocial (301.70), Personality Disorders, Borderline (301.83).

Anxiety disorders which may be treated in accordance with this invention include, but are not limited to, Anxiety Disorders (235), Panic Disorder (235), Panic Disorder with Agoraphobia (300.21), Panic Disorder without Agoraphobia (300.01), Agoraphobia without History of Panic Disorders (300.22), Social Phobia (300.23), Simple Phobia (300.29), Organic Anxiety Disorder (294.80), Psychoactive Substance Anxiety Disorder (292.89), Separation Anxiety Disorder (309.21), Avoidant Disorder of Childhood or Adolescence (313.21), and Overanxious Disorder (313.00).

Effective amounts of NAALADase inhibitors, particularly the β-lactam compounds described herein, can be used for the treatment of the following pathologic psychological conditions: Moderate Mental Retardation; Severe Mental Retardation; Profound Mental Retardation; Autistic Disorder; Attention-Deficit Hyperactivity Disorder; Pervasive Development Disorder NOS; Conduct Disorder, Group Type; Conduct Disorder, Solitary Aggressive Type; Tourette's Disorder; Primary Degenerative Dementia of the Alzheimer Type, Senile Onset, with Delirium; Primary Degenerative Dementia of the Alzheimer Type, Senile Onset, with Delusions; Primary Degenerative Dementia of the Alzheimer Type, Presenile Onset; Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, or Recurrent with Psychotic Features; Personality Disorders, Paranoid; Personality Disorders, Schizoid; Personality Disorders, Schizotypal; Personality Disorders, Antisocial; Personality Disorders, Borderline, Anxiety Disorders, Panic Disorder, Panic Disorder with Agoraphobia, Panic Disorder without Agoraphobia, Agoraphobia without History of Panic Disorders, Social Phobia, Simple Phobia, Obsessive Compulsive Disorder, Post-Traumatic Stress Disorder, Generalized Anxiety Disorder, Anxiety Disorder NOS, Organic Anxiety Disorder, Psychoactive Substance Anxiety Disorder, Separation Anxiety Disorder, Avoidant Disorder of Childhood or Adolescence, and Overanxious Disorder.

One or more neurogenic NAALADase inhibitors, including particularly neurotropic β-lactam antibiotics or β-lactamase inhibitors can be used alone, in combination or in combination with P-glycoprotein inhibitors to treat the following psychotic conditions: Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Personality Disorders, Paranoid; Personality Disorders, Schizoid; Personality Disorders, Schizotypal; Personality Disorders, Antisocial; Personality Disorders, Borderline.

Examples of psychotic conditions which are most preferably treated in accordance with the method of this invention include Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Personality Disorders, Schizoid; and Personality Disorders, Schizotypal.

In one preferred aspect of this invention there is provided a treatment for anxiety. Examples of anxiety disorders which are treated using the present method and pharmaceutical formulations of this invention, include Anxiety Disorders, Panic Disorder, Panic Disorder with Agoraphobia, Panic Disorder without Agoraphobia, Agoraphobia without History of Panic Disorders, Social Phobia, Simple Phobia, Obsessive Compulsive Disorder, Post-Traumatic Stress Disorder, Generalized Anxiety Disorder, Anxiety Disorder NOS, Organic Anxiety Disorder, Psychoactive Substance Anxiety Disorder, Separation Anxiety Disorder, Avoidant Disorder of Childhood or Adolescence, and Overanxious Disorder.

Examples of the anxiety disorders which are most preferredly treated include Panic Disorder; Social Phobia; Simple Phobia; Organic Anxiety Disorder; Obsessive Compulsive Disorder; Post-traumatic Stress Disorder; Generalized Anxiety Disorder; and Anxiety Disorder NOS.

The NAALADase inhibitors used as the neurochemically functional agent in the methods and formulations of the present invention are, in one embodiment of the invention, characterized particularly by their binding to penicillin-binding proteins [as determined using methods described, for example, by B. G. Sprat, Properties of the penicillin-binding proteins of *Escherichia coli* K12, Eur. J. Biochem., 72:341-352 (1977) and N. H. Georgopapadakou, S. A. Smith, C. M. Cimarusti, and R. B. Sykes, Binding of monolactams to penicillin-binding proteins of *Escherichia coli* and *Staphylococcus aureus*: Relation to antibacterial activity, Antimocrob. Agents Chemother., 23:98-104 (1983)] and, in the case of antibiotics, by their inhibition of selective carboxypeptidase and/or transpeptidase activity on peptide substrates comprising the amino acid sequence Ala-D-γ-Glu-Lys-D-alanyl-D-alanine. Such compounds include particularly, β-lactam compounds. Preferred β-lactam compounds for use in accordance with this invention are penicillins, cephalosporins, and monocyclic and bicyclic analogs and/or derivatives thereof. Commercially available antibiotics for use in the methods and manufacture of pharmaceutical formulations of this invention include penams, cephems, 1-oxa-1-dethia cephems, clavams, clavems, azetidinones, carbapenams, carbapenems and carbacephems.

The following compounds are illustrative of β-lactam compounds for use in accordance with this invention.

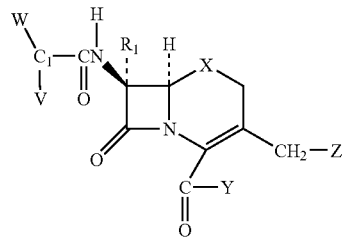

Ia wherein

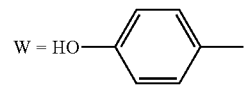

$V=-CO_2M$, $SO_3M$, $SO_2M$, $PO_3M_2$, $PO_2M$, wherein M=H or a pharmaceutically acceptable salt or ester forming group, $C_1$ chirality can be R or S, each epimer having unique biological activity;

$X=O$;

$R_1$=lower alkoxyl, preferably methoxy;

$Y=OM$, M=H, a pharmaceutically acceptable salt, or active ester forming group such as 1-indanyl, pivaloyloxymethyl, acetoxymethyl; and $Z=$

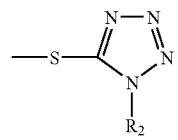 wherein $R_2$ = lower alkyl, preferably methyl, or branched lower alkyl.

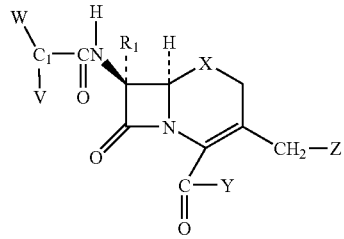

Ib wherein

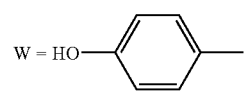

$V=-CO_2M$, $SO_3M$, $SO_2M$, $PO_3M_2$, $PO_2M$, wherein M=H or a pharmaceutically acceptable salt or ester forming group, $C_1$ chirality can be R or S, each epimer having unique biological activity;

X=O;

$R_1$=H;

Y=OM, M=H, a pharmaceutically acceptable salt, or active ester forming group such as 1-indanyl, pivaloyloxymethyl, acetoxymethyl; and

Z=

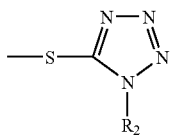

wherein $R_2$=lower alkyl, preferably methyl, or branched lower alkyl.

Ic

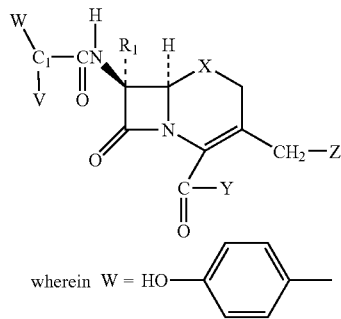

wherein W = HO—⟨phenyl⟩—

V=—$CO_2M$, $SO_3M$, $SO_2M$, $PO_3M_2$, $PO_2M$, wherein M=H or a pharmaceutically acceptable salt or ester forming group, $C_1$ chirality can be R or S, each epimer having unique biological activity;

X=S, S=O, $SO_2$;

$R_1$=lower alkoxy, preferably methoxy;

Y=OM, M=H, a pharmaceutically acceptable salt, or active ester forming group such as 1-indanyl, pivaloyloxymethyl, acetoxymethyl; and

Z=

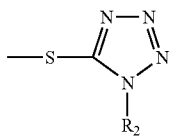

wherein $R_2$=lower alkyl, preferably methyl, or branched lower alkyl.

Id

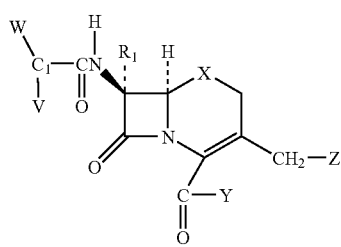

wherein

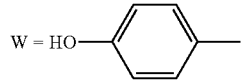

W = HO—⟨phenyl⟩—

V=—$CO_2M$, $SO_3M$, $SO_2M$, $PO_3M_2$, $PO_2M$, wherein M=H or a pharmaceutically acceptable salt or ester forming group, $C_1$ chirality can be R or S, each epimer having unique biological activity;

X=S, S=O, $SO_2$;

$R_1$=H;

Y=OM, M=H, a pharmaceutically acceptable salt, or active ester forming group such as 1-indanyl, pivaloyloxymethyl, acetoxymethyl; and

Z=

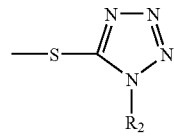

wherein $R_2$=lower alkyl, preferably methyl, or branched lower alkyl.

Ie

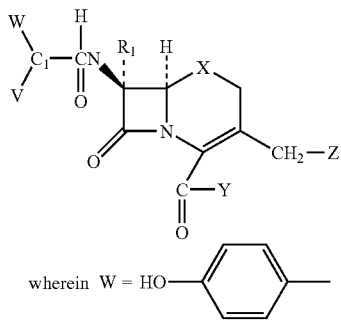

wherein W = HO—⟨phenyl⟩—

V=—$CO_2M$, $SO_3M$, $SO_2M$, $PO_3M_2$, $PO_2M$, wherein M=H or a pharmaceutically acceptable salt or ester forming group, $C_1$ chirality can be R or S, each epimer having unique biological activity;

X=C;

$R_1$=lower alkoxyl, preferably methoxy;

Y=OM, M=H, a pharmaceutically acceptable salt, or active ester forming group such as 1-indanyl, pivaloyloxymethyl, acetoxymethyl; and

Z=

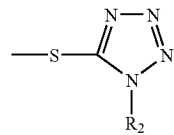

wherein R₂=lower alkyl, preferably methyl, or branched lower alkyl.

If

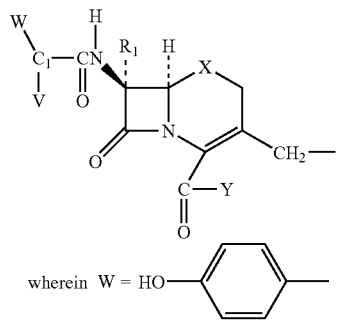

V=—CO$_2$M, SO$_3$M, SO$_2$M, PO$_3$M$_2$, PO$_2$M, wherein M=H or a pharmaceutically acceptable salt or ester forming group, C$_1$ chirality can be R or S, each epimer having unique biological activity;

X=C;

R$_1$=H;

Y=OM, M=H, a pharmaceutically acceptable salt, or active ester forming group such as 1-indanyl, pivaloyloxymethyl, acetoxymethyl; and

Z=

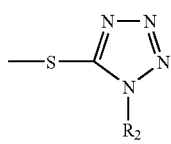

wherein R$_2$=lower alkyl, preferably methyl, or branched lower alkyl.

Ig

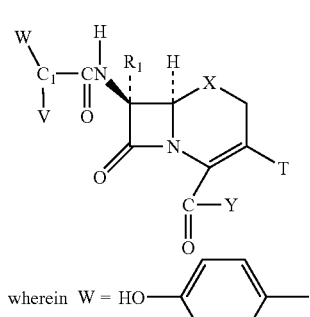

V=—CO$_2$M, SO$_3$M, SO$_2$M, PO$_3$M$_2$, PO$_2$M, wherein M=H or a pharmaceutically acceptable salt or ester forming group, C$_1$ chirality can be R or S, each epimer having unique biological activity;

X=C;

R$_1$=H;

Y=OM, M=H, a pharmaceutically acceptable salt, or active ester forming group such as 1-indanyl, pivaloyloxymethyl, acetoxymethyl, etc.; and T=Cl, F, Br, I, CH$_3$, C$_2$-C$_4$ alkyl, aryl, including heteroaryl, S-alkyl, S-aryl, including S-heteroaryl, SO$_3$R(R=H, alkyl, aryl), SO$_2$R(R=H, alkyl, aryl), N-alkyl$_2$, N-aryl$_2$, CO$_2$R (R=H, alkyl), P-alkyl$_2$, P-aryl$_2$, PO$_3$R$_2$(R=H, alkyl, aryl).

Ih

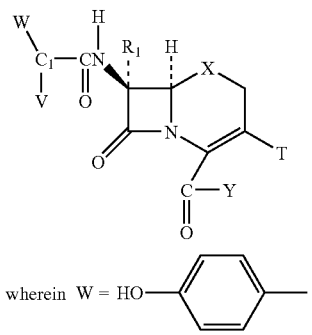

V=—CO$_2$M, SO$_3$M, SO$_2$M, PO$_3$M$_2$, PO$_2$M, wherein M=H or a pharmaceutically acceptable salt or ester forming group, C$_1$ chirality can be R or S, each epimer having unique biological activity;

X=C;

R$_1$=lower alkoxyl, preferably methoxy;

Y=OM, M=H, a pharmaceutically acceptable salt, or active ester forming group such as 1-indanyl, pivaloyloxymethyl, acetoxymethyl, etc.; and T=Cl, F, Br, I, CH$_3$, C$_2$-C$_4$ alkyl, aryl, including heteroaryl, S-alkyl, S-aryl, including S-heteroaryl, SO$_3$R(R=H, alkyl, aryl), SO$_2$R(R=H, alkyl, aryl), N-alkyl$_2$, N-aryl$_2$, CO$_2$R (R=H, alkyl), P-alkyl$_2$, P-aryl$_2$, PO$_3$R$_2$(R=H, alkyl, aryl).

IIa

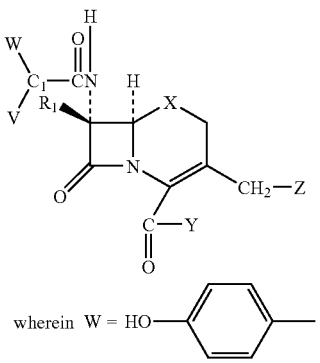

V=—CO$_2$M, SO$_3$M, SO$_2$M, PO$_3$M$_2$, PO$_2$M, wherein M=H or a pharmaceutically acceptable salt or ester forming group, C$_1$ chirality can be R or S, each epimer having unique biological activity;

X=O;

$R_1$=lower alkoxy, preferably methoxy;

Y=OM, M=H, a pharmaceutically acceptable salt, or active ester forming group such as 1-indanyl, pivaloyloxymethyl, acetoxymethyl; and

Z=

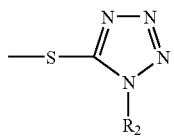

wherein $R_2$=lower alkyl, preferably methyl, or branched general alkyl.

I

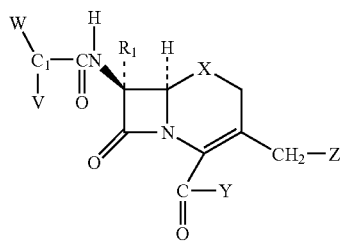

II

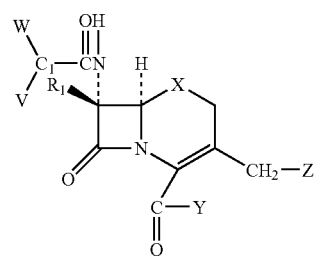

III

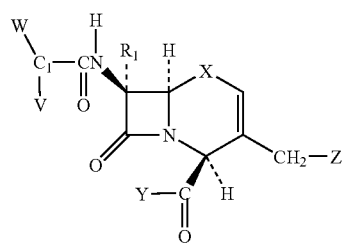

IV

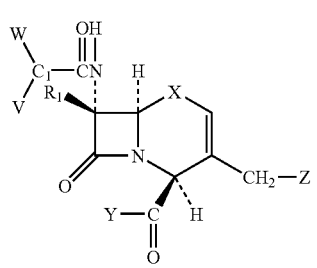

III'

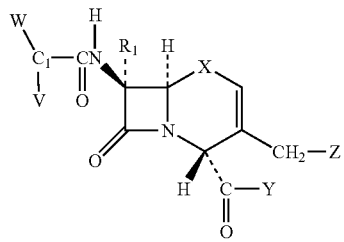

IV'

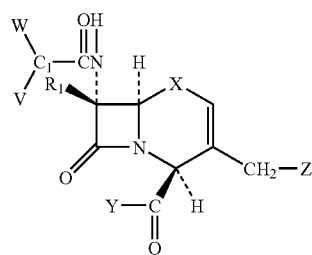

accordance with this invention are those compounds of formulas III, N, III', and IV', respectively wherein the groups W, V, X, $R_1$, Y, M, and Z are as defined for compounds Ia-If, respectively.

IX

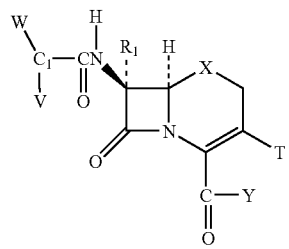

X

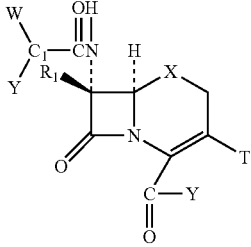

XI

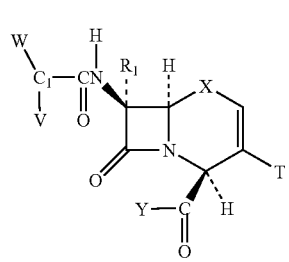

Other preferred compounds, IXa-IXf, Xa-Xf, XIa-XIf, XIIa-XIIf, XI'a-XI'f, and XII'a-XII'f, for use in accordance with this invention are those compounds of formulas IX, X, XI, XII, XI', and XII', respectively wherein the groups W, V, X, $R_1$, Y, and M are as defined for compounds Ia-If, respectively, and the group T is defined as for compounds Ig and Ih, respectively.

Another group of preferred compounds XIIIa-XIIIf, XIVa-XIVf, XVa-XVf, XVIa-XVIf, XV'a-XV'f, and XVI'a-XVI'f for use in accordance with this invention are those compounds of formulas XIII, XIV, XV, XVI, XV', and XVI', respectively wherein the groups W, V, X, $R_1$, Y, and M are as defined for compounds Ia-If, respectively, and group T is defined as for compounds Ig and Ih, respectively.

-continued

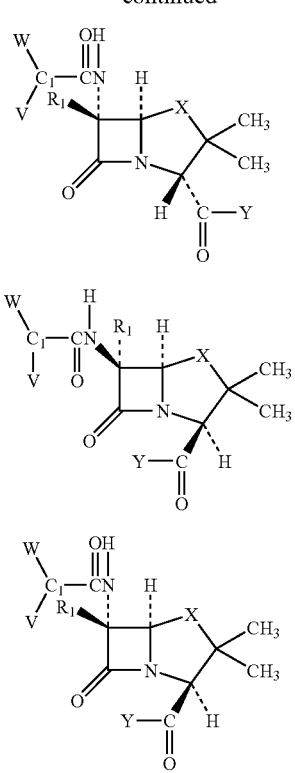

XVIII

XIX

XX

One other group of preferred compounds for use in accordance with this invention are compounds XVIIa-XVIIf, XVIIIa-XVIIIf, XIXa-XIXf, and XXa-XXf, respectively wherein the groups W, V, X, $R_1$, M, and Y are as defined for compounds Ia-If, respectively.

In one preferred embodiment of the present invention the protease inhibitor is a compound of the formula:

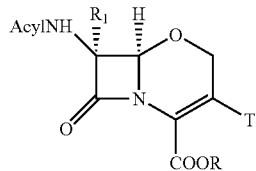

wherein R is hydrogen, a salt forming group or an active ester forming group; R' is hydrogen or $C_1$-$C_4$ alkoxy; T is $C_1$-$C_4$ alkyl, halo (including chloro, fluoro, bromo, and iodo), hydroxy, $O(C_1$-$C_4)$alkyl, or —$CH_2B$ wherein B is the residue of a nucleophile B:H, and Acyl is the residue of an organic acid Acyl-OH.

Examples of such commercially available compounds (1-alkoxy-1-dethia cephems) are moxalactam and flomoxef. Moxalactam is described and claimed in U.S. Pat. No. 4,323,567, the specification of which is expressly incorporated herein by reference. Moxalactam is particularly preferred due to its good blood-brain barrier transport thus providing a relatively high concentration ratio of that compound in the brain relative to blood/serum levels.

In another embodiment invention moxalactam or another commercially available β-lactam antibiotic (or derivative or analogue thereof) detailed for parenteral administration to achieve clinically effective antibiotic tissue concentrations, is converted to the corresponding mono- or bis-active esters to improve oral absorption of said compounds to a level sufficient to inhibit neurogenic protease activity in the brain and concomitantly effect behavior and cognitive performance, albeit at a serum concentration insufficient for clinical antibiotic efficacy.

Alternatively an N-substituted glutamate derivation or a 2-deamino 2-substituted glutamate analog, is converted to a corresponding active ester derivative. Examples of suitable in vivo hydrolysable (active) ester groups include, for example, acyloxyalkyl groups such as acetoxymethyl, pivaloyloxymethyl, β-acetoxyethyl, β-pivaloyloxyethyl, 1-(cyclohexylcarbonyloxy) prop-1-yl, and (1-aminoethyl) carbonyloxymethyl; alkoxycarbonyloxyalkyl groups, such as ethoxycarbonyloxymethyl and alpha-ethoxycarbonyloxyethyl; dialkylaminoalkyl groups, such as ethoxycarbonyloxymethyl and β-ethoxycarbonyloxyethyl; dialkylaminoalkyl especially di-lower alkylamino alkyl groups such as dimethylaminomethyl, dimethylaminoethyl, diethylaminomethyl or diethylaminoethyl:2-(alkoxycarbonyl)-2-alkenyl groups such as 2-(isobutoxycarbonyl) pent-2-enyl and 2-(ethoxycarbonyl)but-2-enyl; lactone groups such as phthalidyl and dimethoxyphthalidyl; and esters linked to a second β-lactam antibiotic or to a β-lactamase inhibitor. One example of such chemical modification of a commercially available parenteral β-lactam antibiotic is moxalactam (Ia, Y=OH, $R_1$=OCH$_3$, and V=COM wherein, M=OH) is the preparation one of its active ester analogue Ia wherein Y=OM, M=H or an active ester, e.g., 1-indanyl and V=CO$_2$M wherein M is H or an active ester and wherein at least one of V and Y include an active ester moiety.

Suitable pharmaceutically acceptable salts of the carboxy group of the above identified β-lactam antibiotics or glutamate derivatives or analogs include metal salts, e.g. aluminum, alkali metal salts such as sodium or potassium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl)amine or tris-(2-hydroxyethyl)amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-β-phenethylamine, dehydroabietylamine, N,N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt. Salts within compounds of formula (I), may be prepared by salt exchange in conventional manner.

In another embodiment of the present invention a penicillin or penicillin analog of the formula

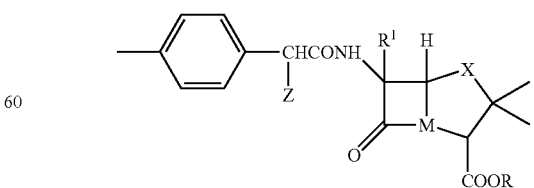

is employed as a NAALADase inhibitor wherein said formula X=O, S, SO, $SO_2$ or C; R is H or a pharmaceutical acceptable salt-forming or ester-forming group; $R^1$ is H or lower alkoxy, G is hydrogen or hydroxy, and Z is amino, acylamino, $CO_2M$, $SO_3M$, $PO_3M_2$ or $PO_2M$ wherein M is hydrogen or a pharmaceutically acceptable salt-forming or ester-forming group, preferably an active ester-forming group.

Non-antibiotic or weakly antibiotic penam and cephem or cephem sulfoxides and sulfones and structurally related β-lactamase inhibitors such as tazobactam, clavulanic acid and sulbactam, are particularly useful in applications where development of antibiotic resistance is of concern.

There exists a wide variety of commercially available β-lactam antibiotics that can be used, or modified or formulated for use to optimize their efficacy, in accordance with this invention. Examples of such compounds are:

cefamandole nafate (Mandol)

cefazolin sodium (Zolicef, Ancef, Kefzol)

cemetaxole sodium (Zeegazone)

cefonocid sodium (Monocid)

cefoperazone sodium (Cefobid)

ceforanide (Precef)

cefotaxime sodium (Claforan)

cefotetan sodium (Cefotan, Apatef)

cefoxitin sodium (Mefoxin)

ceftazidime (Ceptaz, Fortaz, Tazicef, Tazidime)

ceftizoxime sodium (Kefurox, Zinacef)

ceftriaxone (Rocephin)

ceeftriaxone sodium (Rocephin)

cefuroxime-injectable (Kefurox, Zinacef)

cephradine-injectable (Velosef-injectable)

cephalothin sodium (Keflin, Seffin)

cephaapirin sodium (Cefadyl)

moxalactam (Moxam)

amoxicillin (Amoxil, Polymox)

amoxicillin and clavulanate (Augmentin)

ampicillin (Omnipen, Principen)

ampicillin and sulbactam (Unasyn)

azlocillin (Azlin)

bacammpicillin (Spectrobid)

carbenicillin (Geocillin, Geopen)

cefaclor (Ceclor)

cefdadroxil (Duricef, Ultracef)

cefamandole (Mandol)

cefazolin sodium (Ancef, Kefzol)

cefixine (Suprax)

cefinetazole sodium (Zefazone)

cefonicid (Monocid)

cefoperazone (Cefobid)

ceforanide (Precef)

cefotaxime (Claaforan)

cefotetan (Cefotan)

cefoxitin (Mefoxin)

cefprozil-injectable cefprozil-oral (Cefzil)

ceftazidime (Ceptaz, Fortax)

ceftizoxime (Cefizox)

ceftriaxone (Rocephin)

cefuroxime (Ceftin, Zinacef)

cephalexin (Keflex, Keftab)

cephalothin (Keflin)

cephapirin (Cefadyl)

cephradine (Anspor, Velosef)

cloxacillin (Cloxapen, Tegopen)

cyclacillin dicloxacillin (Dycill, Pathocil)

loracarbef-injectable loracarbef-oral methicillin (Staphcillin)

mezlocillin (Mezlin)

moxalactam (Moxam)

nafcillin (Nafcil, Unipen)

oxacillin (Bactocill, Prostaphlin)

penicillamine (Cuprimine, Depen)

penicillin G (Wycillin, Pentids, Bicillin LA)

penicillin V (Veetids, V-Cillin K)

piperacillin (Pipracil)

ticarcillin (Ticar) ticarcillin and clavulanate (Timentin)

Other commercially available β-lactam antibiotics include imipenem (primaxin) which is typically given in combination with cilastatin (which prevents any degradation by renal enzymes). Other β-lactam antibiotics include meropenem (Meronem/Zeneca) and aztreonam (Azacetam). Other penems include biapenem, panipenem, carumonam, and ritipenam. Art-recognized β-lactamase inhibitors which also exhibit cross-inhibition of NAALADase, and which may or may not exhibit independent antibiotic activity are particularly useful in accordance with this invention.

Those β-lactam antibiotic compounds detailed for parental administration can be modified, as indicated above, as their active ester duratives to improve oral absorption with the goal of attaining brain levels of the compound sufficient to inhibit neurogenic protease, but not necessarily sufficient to provide clinically effective antibiotic blood levels. Other antibiotics that may rely for their antibiotic efficacy on inhibition of protease mediated cell wall synthesis, for example gamma-lactones and/or quinoline antibiotics may also find us in accordance with this invention.

Other compounds capable of neurogenic peptidase inhibition via the mechanism proposed for the activity of β-lactam compounds can be identified using art recognized molecular discovery techniques, for example, that described in U.S. Pat. No. 5,552,543, the specification of which is expressly incorporated by reference. That patent described algorithms for detecting correlation between antibacterial activity and the "lock and key" interactions which take place between penicillin-binding proteins and β-lactam antibiotics. Such molecular modeling techniques can be correlated with other drug modeling techniques (for example that described in published PCT International Application No. WO 99/10522, the text of which is expressly incorporated herein by reference) for identifying compounds with good blood-brain barrier transport efficacies to identify optimally effective compounds for use in accordance with the embodiments of this invention. Thus, for treatments in accordance with this invention targeting neurogenic NAALADase, it is not only important that compounds useful in this invention are active as inhibitors of the targeted neurological protease (NAALADase), but it is also important that such compounds can be delivered with some threshold degree of efficiency through the blood-brain barrier to provide effective protease inhibiting concentration of the drug in the brain. Such blood-brain barrier transport properties can derive inherently from compound structure, or such compounds can be formulated and/or conjugated with other chemical entities effective to enhance blood-brain barrier transport. There has been a significant research and development effort directed to the preparation and formulation of compounds to enhance their blood-brain barrier transport, and such technologies can be applied to enhance brain concentration of the protease inhibitors and adjuvants therefor useful in accordance with this invention.

Animal tests indicate a threshold effective dose of moxalactam (administered parenterally) to be about 50 μg/kg of body weight. Based on animal test data and on the known distribution of parenterally administered moxalactam between the brain and other body tissues, that the effective minimum neurogenic protease inhibiting, concentration of moxalactam in the brain is about 30 nM. Clavulanic acid has been shown to be an effective inhibitor of neurogenic NAALADase when administered i.p. at less than 1 microgram per kilogram of body weight. The range of effective dosage levels of the NAALADase inhibitors when used in the treatment of behavioral and/or cognitive disorders in accordance with this invention will depend significantly on patient body weight, the affinity of the inhibitor for the target neurogenic protease, the blood-brain barrier transport characteristics of the active compound, the mode of administration and the optional use of available drug formulations/conjugation technologies available for enhancement of blood-brain barrier transport. For parenterally administered moxalactam the minimum effective dose in hamsters and other test species is about 50 micrograms per kg of body weight, more or less. The use of moxalactam in an oral dosage form, preferably modified or derivatized in the form of an active ester, is estimated to range from about 2.5 to about 50 mg per dose, much less than the dose of moxalactam necessary to provide therapeutically effective antibiotic concentration. The effective oral dose of clavulanate is expected to be about 0.1 to about 10 mgs per dose. Clavulanate is orally absorbed and it exhibits good blood brain barrier transport.

The effective doses of other protease inhibitors will vary, again depending on their inherent affinity for the target protease, the selected route of administration, patient weight, and blood-brain barrier transport efficiency. The effective dosages of NAALADase inhibitors used in accordance with the present invention can be readily determined empirically using animal models coupled with use of art recognized analytical techniques. Typically, the dosage levels for β-lactam antibiotic compounds used in the methods and formulations of this invention is less than that necessary to achieve clinically effective antibacterial levels. Parenteral dosages of β-lactam antibiotic compounds can range from about 1 to about 80 mg per dose. Oral dosages can range from about 2.5 to about 150 mg per dose. Higher or lower dosage amounts may be appropriate and used in accordance with this invention when patient circumstances dictate such in the judgement of the attending physician. Thus, for example, where patient/clinical conditions are such that the inherent antibiotic activity of the β-lactam compounds are not considered to be a complicating contraindication, higher doses of the antibiotic up to or exceeding the dosage levels capable of providing threshold clinically effective antibiotic blood levels can be used to treat patients in need of therapy effected by NAALADase inhibition in accordance with this invention.

Further in accordance with this invention, other art-recognized NAALADase inhibitors capable of crossing the blood brain barrier in effective amounts can be used for treatment of behavioral and cognitive disorders. For example, they can be used to improve cognitive performance in patients afflicted with dementia or to reduce aggession. Examples of known NAALADase inhibitors include general metallopeptidase inhibitors such as O-phenanthroline, metal chelators such as ethylenediaminetetracetic acid (EDTA) and ethyleneglycolbis(betaminoethylether)-N,N-tetracetic acid (EGTA) and peptide analogs such as quesqualic acid, aspartate glutamate (Asp-Glu), Glu-Glu, Gly-Glu, γ-Glu-Glu and beta-N-acetyl-L-aspartate-L-glutamate. Other NAALADase inhibitors are the more recently described compounds of the formula

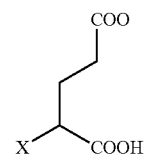

wherein X is RP(O)(OH)CH$_2$— [See U.S. Pat. No. 5,968,915 incorporated herein by reference]; RP(O)(OH)NH— [See U.S. Pat. No. 5,863,536 incorporated herein by reference]; RP(O)(OH)O—[See U.S. Pat. No. 5,795,877 incorporated herein by reference]; RN(OH)C(O)Y— or RC(O)NH(OH)Y wherein Y is CR$_1$R$_2$, NR$_3$ or O [See U.S. Pat. No. 5,962,521 incorporated herein by reference]; or X is RS(O)Y, RSO$_2$Y, or RS(O)(NH)Y wherein Y is CR$_1$R$_2$, NR$_3$ or O [See U.S. Pat. No. 5,902,817 incorporated herein by reference].

Each of the above-mentioned U.S. patents suggest uses of the described NAALADase inhibitors in treatment of disease states associated with glutamate abnormality including epilepsy, stroke, Alzheimer's disease, Parkinson's disease, Amyotrophic Lateral Sclerosis (ALS), Huntington's disease, schizophrenia, chronic pain, ischemia and neuronal insult. The discovery underlying the present invention enables use of inhibitors of penicillin binding protein (bacterial carboxypeptidase or transpeptidase) particularly β-lactam antibiotics and β-lactamase inhibitors for developing therapeutic protocols for such disease states based on the previously unappreciated activity of such compounds as NAALADase inhibitors. More recently high concentrations of glutamate in nervous tissues have been associated with multiple sclerosis, and it is contemplated that inhibition of NAALADase in such tissues and consequently inhibition of its production of glutamate can provide therapeutic benefit to patients afflicted with the disease by either reducing the severity of the symptoms or by reducing the occurrence of their onset.

The present invention further provides certain pharmaceutical formulations for treatment of behavioral or cognitive disorders and other disease states associated with production of abnormal glutamate concentrations in nervous tissues and other tissues harboring NAALADase activity. Generally the formulation comprises a neurologically active ingredient including a compound capable of inhibiting a bacterial enzyme and capable of inhibiting a neurogenic peptidase (e.g., NAALADase) that is known, by empirical evidence, to selectively act on a peptide comprising the amino acid sequence Ala-D-γ-Glu-Lys-D-alanyl-D-alanine, and a pharmaceutically acceptable carrier therefor. In one embodiment the pharmaceutical formulation in a unit dosage form comprises an amount of a β-lactam compound capable of inhibiting NAALADase activity in a patient experiencing or disposed to develop a medical condition that could be prevented or treated to reduce its symptoms by NAALADase inhibition. The amount of the peptidase (NAALADase) inhibitor and the nature of the carrier is dependent, of course, on the intended route of administration. The amount of inhibitor is that amount effective to provide upon delivery by the predetermined route of administration, a concentration of the inhibitor in the tissue where NAALADase inhibition is desired, e.g., in the brain effective to treat and reduce symptoms of the targeted behavioral or cognitive disorders or other disorders than can be treated by inhibition of NAALADase activity. In embodiments utilizing β-lactam antibiotic compounds the amount of the peptidase inhibitor in the present formulations is typically less than that capable of providing clinically effective bacterial protease inhibition, i.e., less than that capable of providing antibiotically effective levels when administered to a patient in the dosage form provided. The peptidase inhibitors for use in accordance with this invention can be combined with one or more pharmaceutically acceptable carriers, and may be administered, for example, orally in such forms as tablets, capsules, caplets, dispersible powders, granules, lozenges, mucosal patches, sachets, and the like. The NAALADase inhibitor can be combined with a pharmaceutically acceptable carrier, for example starch, lactose or trehalose, alone or in combination with one or more tableting excipients and pressed into tablets or lozenges. Optionally, such tablets, caplets or capsules can be enterically coated to minimize hydrolysis/degradation in the stomach. Oral dosage formulations contain about 1 to about 99% by weight active ingredient and about 1 to about 99% of a pharmaceutically acceptable carrier and/or formulating excipients. Optionally, when β-lactam antibiotics are used as the NAALADase inhibitors the dosage forms can be formulated by combining it with a P-glycoprotein inhibitor to provide enhanced drug half-life and brain concentrations of the active ingredient. Alternatively, the protease inhibitor can simply be co-administered with a P-glycoprotein or β-lactamase inhibitor; or the dosage form can comprise a β-lactamase inhibitor (itself also a NAALADase inhibitor) alone or in combination with a P-glycoprotein and a carrier.

In another embodiment of the invention pharmaceutical preparations may contain, for example, from about 2.5% to about 90% of the active ingredient in combination with the carrier, more usually between about 5% and about 60% by weight active ingredient. The pharmaceutical formulations in accordance with one embodiment of this invention are formulated for per os administration, i.e., oral ingestion administration or buccal or sublingual administration (in the form of sachets, lozenges, and/or oral mucosal patches). In another embodiment the dosage form is formulated for per os administration is in a prolonged release dosage form formulated to release the active ingredient over a predetermined period of time.

Topical, dosage forms, including transdermal patches, intranasal, and suppository dosage unit formulations containing the active protease inhibitor and conventional non-toxic pharmaceutically acceptable carriers, adjuvants and vehicles adapted for such routes of administration are also within the scope of this invention.

The pharmaceutical formulations in accordance with this invention alternatively can be delivered via parenteral routes of administration, including subcutaneous administration, intraperitoneal administration, intramuscular administration and intravenous administration. Such parenteral dosage forms are typically in the form of aqueous solutions or dispersions utilizing a pharmaceutically acceptable carrier such as isotonic saline, 5% glucose, or other well known pharmaceutically acceptable liquid carrier composition.

The pharmaceutical forms suitable for injectable use include sterile aqueous solutions or dispersions and sterile powders or lyophilizates for the extemporaneous preparation of sterile injectable solutions or dispersions. In all cases, the dosage form must be sterile and it must be stable under the conditions of manufacture and storage, and must be preserved against the contaminating action of microorganisms. The carrier for injectable formulations can be a solvent or dispersion medium containing, for example, water, ethanol, or a polyol (or example glycerol, propylene glycol and liquid polyethyleneglycol), mixtures thereof, and vegetable oil.

Parenteral dosage forms of the peptidase inhibitors useful for treatment of behavioral and cognitive disorders and other disease states responsive to neurogenic peptidase inhibition can also be formulated as injectable prolonged release formulations in which the protease inhibitor is combined with one or more natural or synthetic biodegradable or biodespersible polymers such as carbohydrates, including starches, gums and etherified or esterified cellulosic derivatives, polyethers, polyesters (particularly polylactide, polygylcolide or poly-lactide-glycolides), polyvinyl alcohols, gelatins, or alginates. Such dosage formulations can be prepared, for example, in the form of microsphere suspensions, gels (of hydrophilic or hydrophobic constitution), or shaped-polymer matrix implants that are well-known in the art for their function as "depot-type" drug delivery systems that provide prolonged release of the biologically active components. Such compositions can be prepared using art-recognized formulation techniques and designed for any of a wide variety of drug release profiles.

The administration of pharmaceutical compositions for use in the present invention can be intermittent or at a gradual, or continuous, constant or controlled rate to a patient in need of treatment. In addition, the time of day and the number of times of day that the pharmaceutical formulation is administered can vary depending on the patient condition and environment. The level of efficacy and optimal dosage and dosage form for any given protease inhibitor for use within the scope of this invention is patient-dependent and adjustable within reasonable ranges in the judgment of the attending physician. The formulation is typically administered over a period of time sufficient to treat or prevent the patient disease state, e.g., to modify the behavioral or cognitive performance of the patient undergoing treatment. The protease inhibitor formulations may be continued to be administered using the same or attenuated dosage protocol for prophylaxis of the targeted disease state.

With knowledge of the existence and function of a neurogenic protease or proteases, such compound or compounds can be readily separated from brain homogenates, cerebral spinal fluid (CSF) or brain tissue extracts and purified for use in structure elucidation and in drug discovery applications. Thus, using art-recognized techniques including specifically affinity chromatography and/or high pressure liquid chromatography, one or more neurogenic proteases having a defined neurochemical function determinative of behavioral phenotype and cognitive performance can be isolated and characterized. Thus for example a β-lactam antibiotic can be covalently bound, optionally through a cleavable linker to a solid substrate, for example, magnetic beads or functionalized silica to form a solid phase capable of selective affinity/interaction with the target protease(s). The β-lactam compound bearing solid substrate is then contacted with CSF, brain homogenate or brain extract at one or more pH levels for a period of time sufficient to allow reaction (or associative binding) of the neurogenic protease with the immobilized β-lactam compound. Alternatively, a protein or peptide substrate comprising the amino acid sequence acyl-D-alanyl-D-alanine can be immobilized on the solid substrate and used as an affinity probe for the target neurogenic protease.

The covalently or associatively bond protease can then be separated from the extract and thereafter released from the solid substrate by a technique dependent on the nature of the protease-immobilized probe interaction. If the protease forms a covalent bond with the immobilized β-lactam compound, the resulting complex can be released from the solid phase substrate, for example by cleaving the cleavable linker to provide a neurogenic protease, more particularly a derivative thereof, substantially free of non-protease components. Alternatively, and preferably, the probe utilized for the protease affinity column exhibits selected associative (non-covalent) affinity for the protease so that the protease can be subsequently released from the solid phase by changing the stringency (ionic strength or pH of the liquid phase) to release the protease from the solid substrate in a form substantially free of non-protease components.

Another procedure for enabling and identifying neuroprotease target of the methods and pharmaceutical formulations of this invention involves use of a penicillin or cephalosporin labeled with a radionucleide ($H^3$). A solution of such is injected into the brain of a test animal (and after a predetermined period of time the animal is euthanized and the brain is immediately extracted/homogenized. The brain extract/homogenate is then subjected to one or more separation processes such as centrifugation, dialysis, and chromatography (e.g., gel fibration chromatography). The separated chemical species are analyzed for presence of the label, and labeled species are isolated, optionally subjected to additional purification procedures, and subjected to physical chemical analysis for structure elucidation.

Using art-recognized protein amino acid analytical techniques/sequencing, the structure of the neurogenic proteases can be readily elucidated thereby enabling preparation of nucleic acid probes encoding for at least a portion of the protease. The probes can then be used to retrieve DNA encoding for the protease from available gene libraries. The targeted gene constructs are analyzed and cloned using art-recognized cloning techniques to provide engineered microorganisms, eukaryote or prokaryote, that can be used to express unlimited amounts of the pure protease, which then can be used in diagnostic or drug screening applications.

In one related embodiment of the invention the protease is conjugated in the form of a hapten for inoculating murine or other species for the production of monoclonal antibodies recognizing one or more epitopes of the neurogenic protease. Antibody production can be carried out utilizing art-recognized hybridoma forming techniques well known to those of ordinary skill in the art. Such procedures are summarized, particularly with respect to formation of monoclonal antibodies exhibiting specific to collagen proteins in U.S. Pat. No. 4,628,077, the specification of which pertinent to the teachings of monoclonal antibody production are expressly incorporated herein by reference. The antibodies can themselves be conjugated by covalent linkage or by affinity linkage (such as via a biotin avidin complex) with a detectable label, for example, a radionucleide, an enzyme, or a fluorescent or electroluminescent species. Such labeled antibodies can be used in diagnostic kits and methods to analyze, for example, cerebral spinal fluid samples, to determine a patient's behavioral or cognitive status as a function of neuroprotease concentrations. Such diagnostic tests can also be utilized to assess patient response to drug therapy and to monitor patient status, again as a function of neurogenic protease concentration. The method can be carried out using art-recognized competitive or sandwich-type specific binding assays well known to those of ordinary skill in the art.

Thus, in accordance with still another embodiment of the invention, there is provided a method for assessing the neurochemical status of a patient comprising the step of contacting a sample of cerebral spinal fluid with a labeled antibody capable of specific binding to an epitope of the neurogenic protease or proteases responsible for modulation of neurochemical pathways determinative of the patient's cognitive performance level and/or behavioral phenotype, and finally comparing the levels detected with those from patient populations of predetermined cognitive or behavioral phenotypes.

In still another embodiment of the invention, there is provided a peptidic neuromodulator or neurotransmitter in substantially pure form. The neuropeptide is characterized by its mediation of patient behavior and cognitive skills, and further by its function as a substrate for neurogenic protease, itself capable of being inhibited by either the D-isomer of moxalactam or a peptide comprising the sequence acyl-D-alanyl-D-alanine. The neurogenic protease exhibiting selective activity on the peptidic neuromodulator or neurotranslator can exhibit proteolytic activity, comprising transprotease or carboxyprotease activity (or stated alternatively transpeptidase or carboxypeptidase activity). The neuropeptide can be isolated from cerebral spinal fluid or brain homogenate using a method similar to that described above for the isolation and purification of the neurogenic protease. However, instead of using a solid substrate with covalently bound β-lactam antibiotic as the affinity probe for the target molecule, penicillin-binding protein (or a form, optionally chemically modified, of the isolated neurogenic protease itself) is immobilized on the surface of the solid substrate. The penicillin-binding protein (PBP) exhibits selective affinity for the peptidic neuromodulator/neurotransmitter, and the peptidic target molecules are preferentially bound to the solid substrate when the PBP-bearing solid phase is contacted with brain homogenate or cerebral spinal fluid under one or more alternative conditions of ionic strength and/or pH. The solid phase bearing the PBP can be used in the form of a chromatographic column, i.e., in an affinity chromatography application, or the solid substrate can simply be dispersed in a homogenate or extract of brain or cerebral spinal fluid to selectively bind the peptidic neuromodulator/neurotransmitter which can thereafter be released from the penicillin-binding protein, isolated and further purified, if necessary, by high pressure liquid chromatography to produce said peptidic neuromodulator/neurotransmitter in substantially pure form free from other proteinaceous compositions. The peptidic neurotransmitter can be used itself as a neurologically active drug substance or it can be used as a drug lead for developing related neuroactive drug substances. Further, the structure of the purified neurotransmitter can be readily ascertained by art-recognized amino acid sequence analysis which will enable the skilled practitioner to prepare a nucleic acid probe (as possibly a synthetic gene), for isolating DNA sequences encoding the peptidic neurotransmitter/neuromodulator. Finally, similar to the use of the gene for the neurogenic protease described above, the isolated gene construct can be cloned and used in the production of clinical quantities of the peptidic neurotransmitter/neuromodulator for drug intervention, for antibody production or in drug discovery protocols.

In one further aspect of the invention it is contemplated that a patient suffering from a cognitive or behavioral disorder can be vaccinated using a vaccine prepared, for example, as a neurogenic protease conjugate capable of evoking an antibody response on inoculation of the patient sufficient to attenuate neurogenic protease function and concomitantly modify the patient's behavioral and/or cognitive phenotype to ameliorate other patient conditions associated with abnormal glutamate concentration/activity, including but not limited to those discussed hereinabove. In one embodiment the conjugate comprises a haptan-conjugate of one or more peptides comprising a 4 to 20 amino acid sequence of NAALADase comprising one or more of the active site motifs of NAALADase or PBP, as described above.

The above-described embodiments of the present invention derive in part from the mechanism of action deduced from data gathered in animal behavioral cognitive and skill models described below. Other embodiments of the invention will be apparent from analysis of the data obtained in the following non-limiting experimental examples, which are but illustrative of the behavior modification and cognitive performance and improvement attainable by use of the method and formulations of the present invention.

EXPERIMENTAL EXAMPLES

Marketed in 1981-1982 moxalactam (Mox) was employed widely in the world as a third-generation cephalosporin-like antibiotic. Clinical efficacy and safety were evaluated in over 2200 patents with bacterial infections (Jackson et al. 1986). Of the 260 patents treated with Mox for gram-negative meningitis, 241 (93%) showed satisfactory response to antibiotic therapy. Patents were treated with 4 g of Mox every 8 hrs for 2-3 weeks. Peak plasma concentrations occur within an one hr after IM injection with an elimination half-life of 2.3 hrs. There is no accumulation with multiple injections occurring at 8-12 hr intervals. Moxalactam can penetrate the blood brain barrier. Cerebrospinal fluid (CSF) levels of Mox range from 25-39 µg/ml following a 2.0 g IV dose of drug. The CSF concentration as a percentage of serum concentration is estimated to be 20%. The D isomer has antibacterial activity and has a greater unbound fraction to plasma protein that the L isomer.

Behavioral Studies with Moxalactam

Methods

Animal Care

Male Syrian golden hamsters (*Mesocricetus auratus*) (140-150 g) obtained from Harlan Sprague-Dawley Laboratories (Indianapolis, Ind.) were housed individually in Plexiglas cages (24 cm×24 cm×20 cm), maintained on a reverse light:dark cycle (14L:10D; lights on at 19:00 hr) and provided food and water ad libitum. Animals were acclimated to the reverse light:dark cycle for at least two weeks before testing. All behavioral tests were conducted during the dark phase of the circadian cycle. All animals were acquired and cared for in accordance with the guidelines published in the Guide for the Care and Use of Laboratory Animals (National Institutes of Health Publications No. 85-23, Revised 1985).

Offensive Aggression

Agonistic behavior can be classified as either offensive or defensive aggression (Blanchard and Blanchard, 1977; Adams, 19798; Albert and Walsh, 1984). Offensive aggression is characterized by the aggressor initiating an attack on an opponent, while defensive aggression lacks active approach. Both types of aggression have their own unique neurobehavioral systems. The stimuli that elicit offensive and defense attack are different, as are the sequences of behaviors that accompany each agonistic response. While much of the empirical data supporting the notion of unique offensive and defensive neural networks have been collected from animal models, there are interesting and compelling similarities in human aggression that suggest a similar neural organization (Blanchard, 1984). Offensive aggression is easily studied using male golden hamsters tested in a resident/intruder paradigm, an established model of offensive aggression (Ferris and Potegal 1988). Placing an unfamiliar male hamster into the home cage of another male hamster elicits a well-defined sequence of agonistic behaviors from the resident that includes offensive aggression.

Behavioral Measures and Analysis

Hamsters are nocturnal and as such all behavioral tests were performed during the first four hrs of the dark phase under dim red illumination. The resident was scored for offensive aggression, e.g., latency to bite the intruder, the total number of bites, total contact time with the intruder and flank marking over a 10 min test period (Ferris and Potegal, 1988). Flank marking is a form of olfactory communication in which a hamsters arches its back and rubs pheromone producing flank glands against objects in the environment (Johnson, 1986). Flank marking frequency is greatly enhanced during aggressive encounters and is particularly robust in dominant animals initiating and winning fights (Ferris et al., 1987).

Parametric data, i.e., latencies and contact time, were analyzed with a one-way ANOVA followed by Newman-Keuls post hoc tests. Non parametric data, i.e., number of bites and flank marks, were analyzed with Kruskal-Wallis tests followed by Mann-Whitney U tests to determine differences between groups. Two sample comparisons were analyzed with paired and unpaired t-Tests for parametric data and Wilcoxon and Mann-Whitney Tests for paired and unpaired non-parametric data, respectively.

Results

I. High Dose Moxalactam

In a pilot study, Mox (50 mg/kg in a volume of ca. 150 µl) was given intraperitoneally (IP) to six male hamsters pre-screened for aggressive behavior toward smaller intruders. Treatments with Mox and saline vehicle were counter balanced so each animal received both treatments separated by at least 48 hr. Animals were tested 90 min after treatment a period estimated to reflect peak plasma levels of Mox (Jackson et al. 1986). Moxalactam was dissolved in 0.9% NaCl and stored on ice. It was prepared fresh for each study.

Figure 1B:
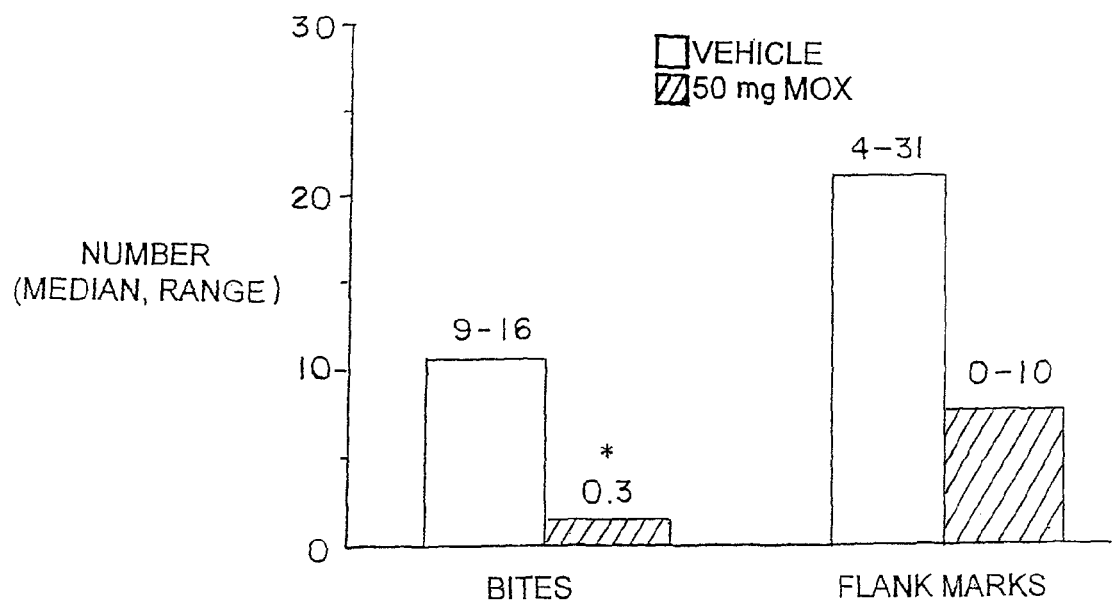

Resident animals treated with saline vehicle bite intruders in less than one min (FIG. 1). Following Mox treatment the mean latency to bite was increased to over six min (p<0.05). In addition, the number of bites over the 10 min observation period were significantly reduced (p<0.05). However, the contact time, i.e., the time the resident spent smelling and exploring the intruder was also significantly reduced (p<0.01). The decrease in flank marking did not reach significance but there was a trend (p<0.07).

SUMMARY

The general decrease in all behavioral measures associated with offensive aggression raises the possibility that the 50 mg/kg dose of Mox has non specific depressive effects on motor activity and arousal. To examine this possibility, it was necessary to run dose response studies to find the lowest dose of Mox that effectively inhibits offensive aggression without altering other behaviors.

II. Moxalactam Dose Response

Figure 2A:
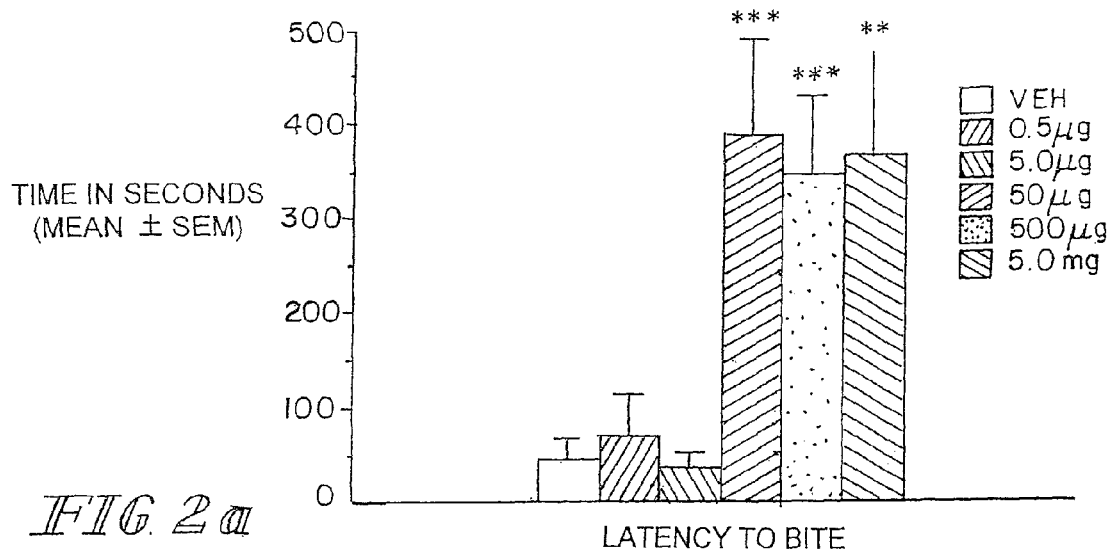
Figure 2B:
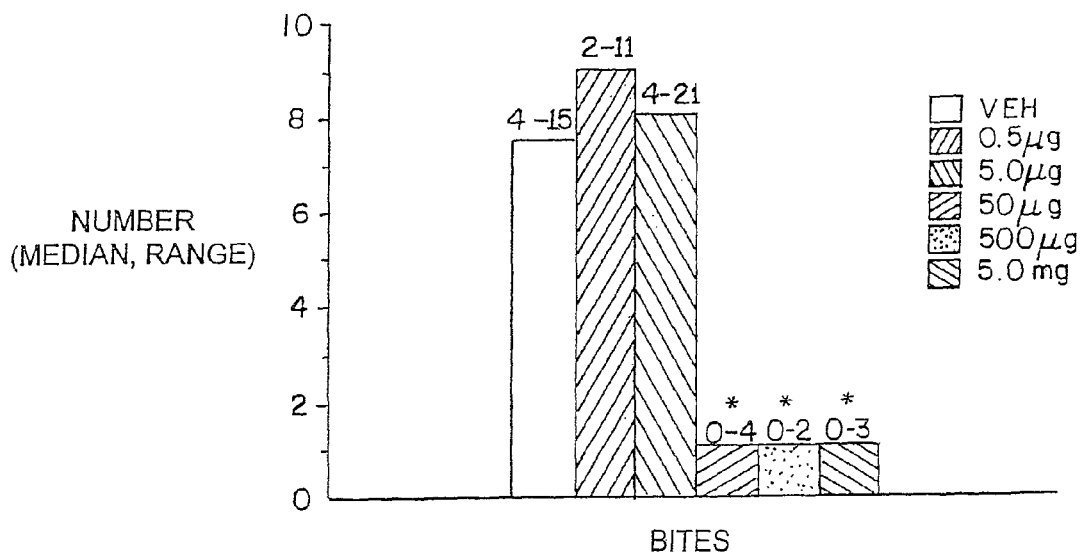
Figure 3A:
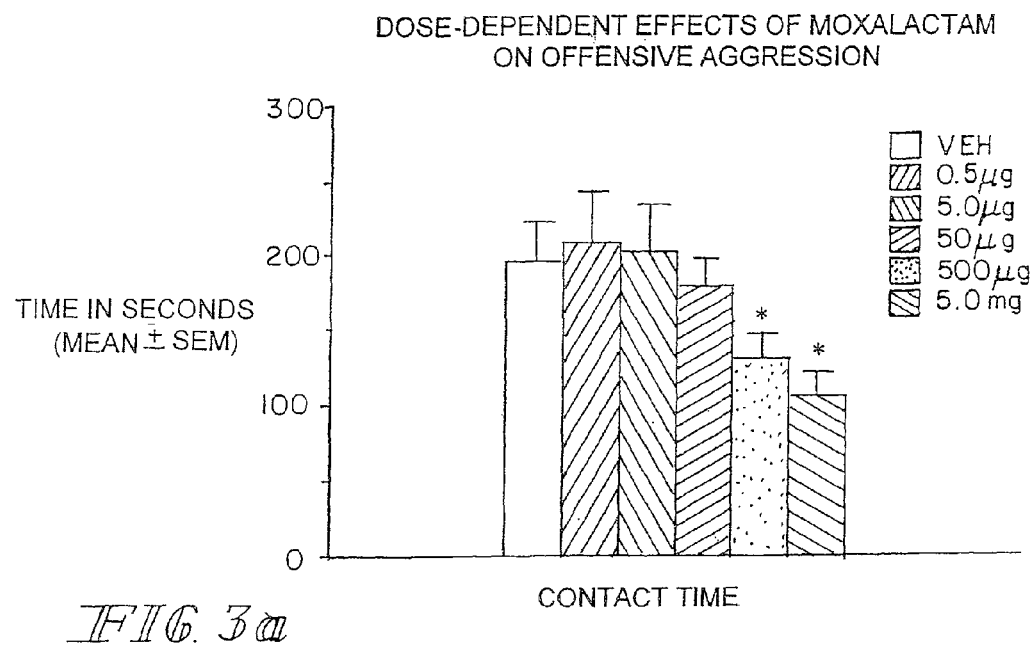
Figure 3B:
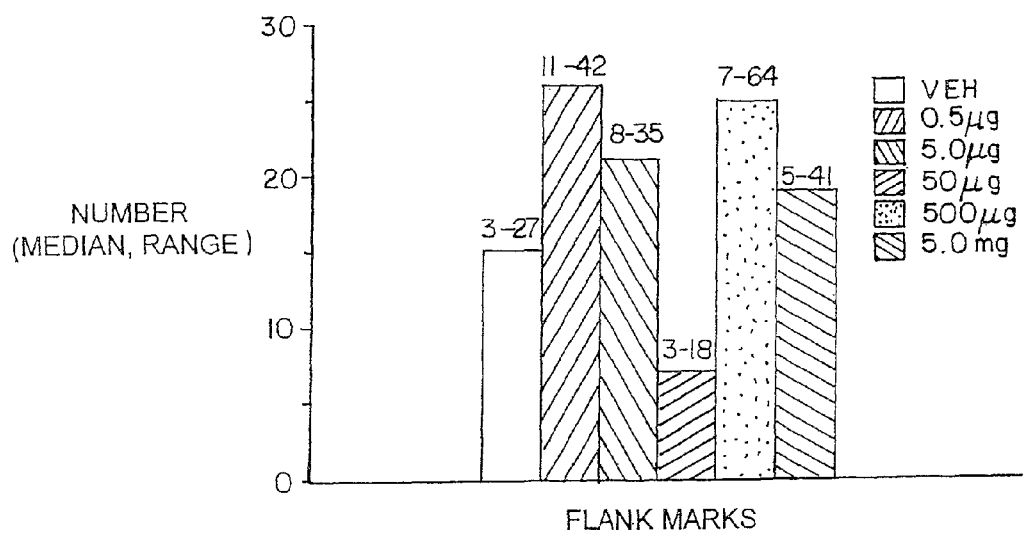

To find the lowest dose of Mox that could significantly reduce offensive aggression, a range of concentrations (vehicle, 0.5, 5.0, 50, 500, and 5000 µg/kg) were tested in six animals (FIGS. 2 & 3) The treatments were counter balanced with each animal receiving each treatment separated by at least 48 hrs. The latency to bite was significantly different between treatments (F (5,30)=5.66; p<0.001). Moxalactam treatment with doses of 5.0 µg and less had no effect on any behavioral measures of offensive aggression. However, the dose of 50 µg/kg significantly delayed bite latency by over seven min (p<0.001) as compared to vehicle control. Doses of 500 µg and 5.0 mg also significantly increased bite latency. As was expected, the same doses that increased bite latency also decreased the number of bites (H=24.12; p<0.001). Animals treated with 50 µg Mox showed a significant reduction in bites (p<0.05). Indeed, three of six animals never bite at all in the 10 min observation period. The contact time was significantly different between treatments (F (5,30)=2.5; p<0.05). Doses of 500 µg and 5 mg significantly reduced contact time as compared to vehicle control (p<0.05 and p<0.01, respectively). Flank marking was not significantly different between groups (H=9.256; p<0.09).

Summary

These data identify the dose of 50 µg/kg of Mox as very effective in inhibiting offensive aggression without significantly reducing contact time and flank marking. Higher doses of Mox, while effective in reducing measures of aggression also reduced contact time. Hence, the 50 µg dose would appear to be best for future behavioral tests. Having identified the most effective dose of Mox a more thorough study using a greater number of animals and a greater spectrum of behavioral tests was necessary.

III. Behavioral Tests With 50 µg Moxalactam

Offensive Aggression

Figure 4A:
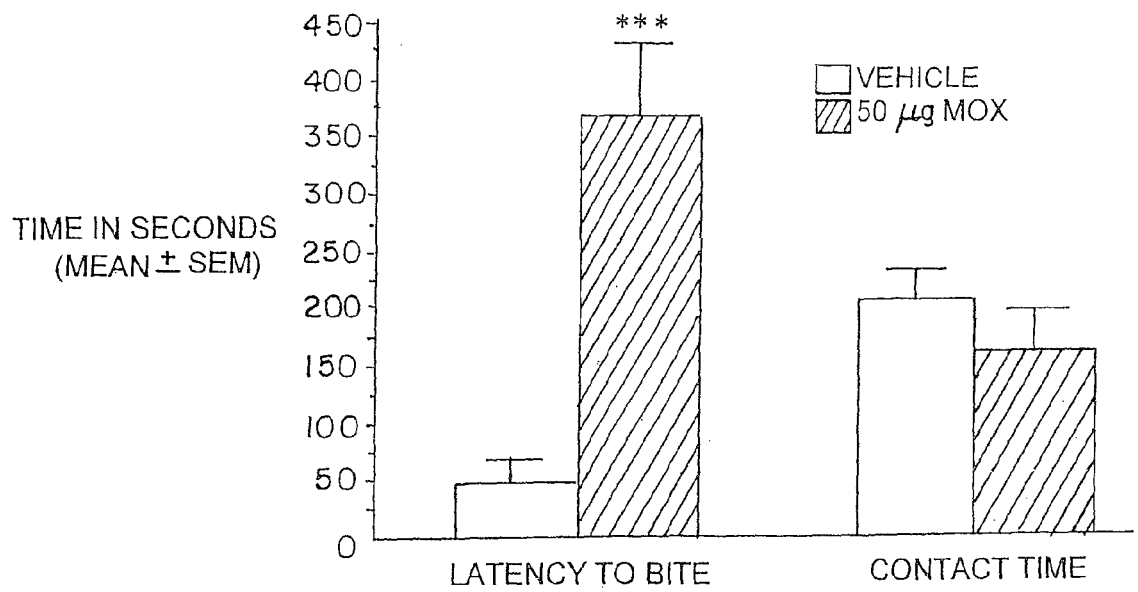
Figure 4B:
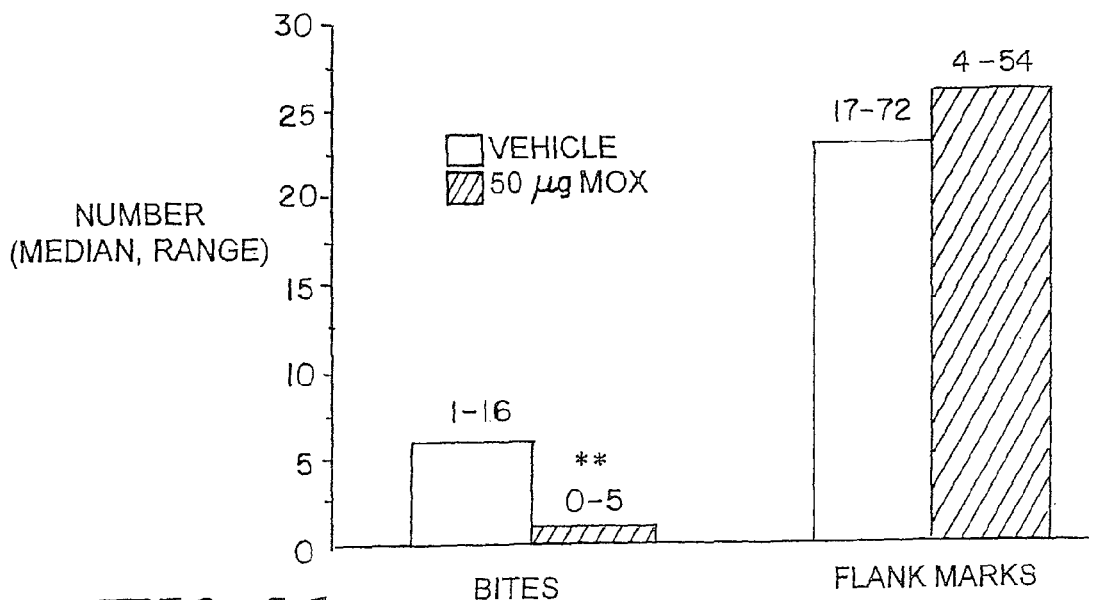

Thirteen hamsters were tested for offensive aggression following treatment with saline vehicle or 50 µg/kg Mox (FIG. 4). Both treatments were given IP in a volume of ca. 150 µl. Animals were tested 90 min after injection. Each animal received both treatments. The order of injections was counter balanced with no less than 48 hrs between treatments. Moxalactam significantly increased bite latency (p<0.001) and reduced the number of bites (p<0.01). There was no significant change in contact time or flank marking.

Summary

This larger study of low dose Mox corroborates the dose-response study confirming that Mox can effectively reduce offensive aggression without altering social behavior as measured by the time spent with the intruder.

Motor Activity in an Open Field

Figure 5A:
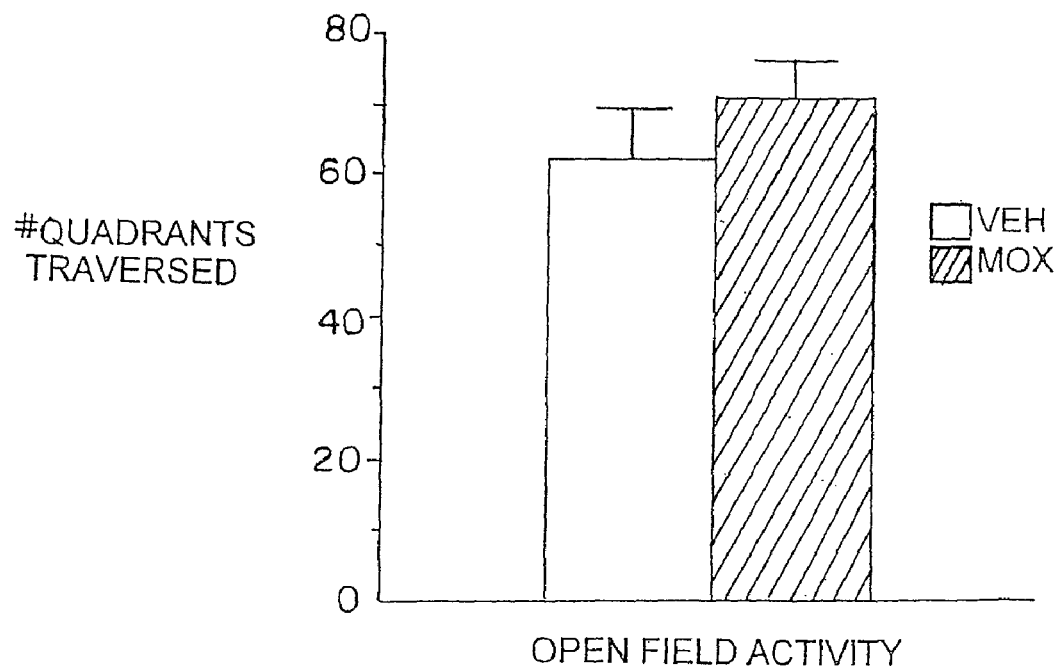
Figure 5B:
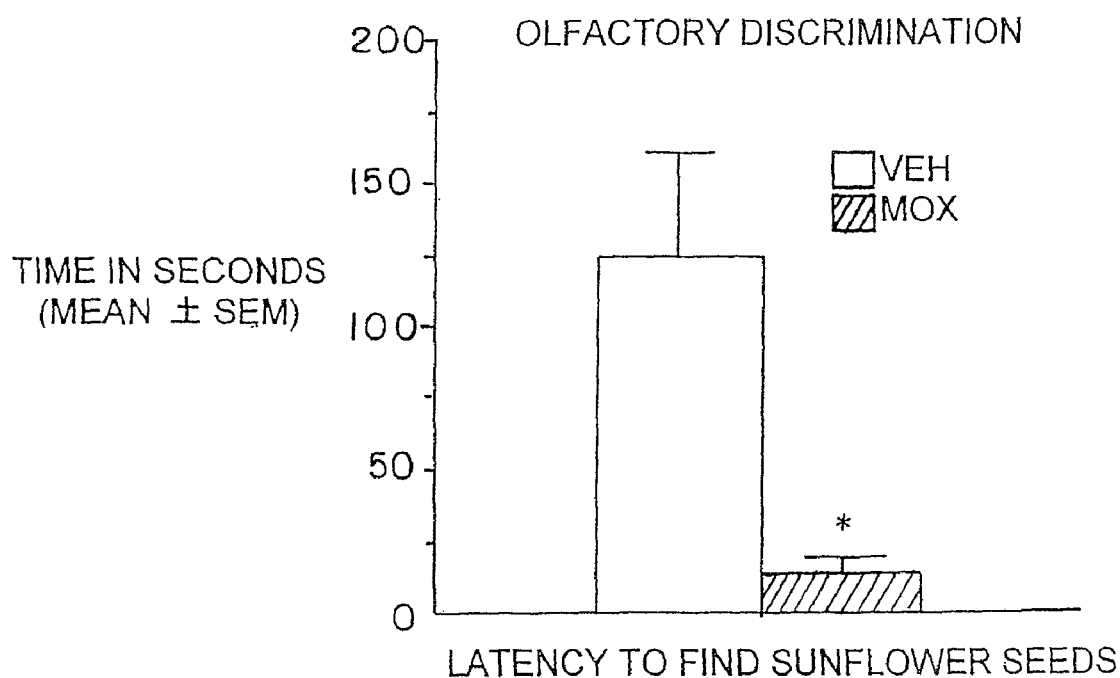

Six animals were tested for general motor activity in an "open field" following treatment with saline vehicle or 50 µg/kg Mox (FIG. 5). The study was counter balanced with each animal receiving each treatment. Ninety minutes after injection a single animal was placed into a large clean Plexiglas cage (48×32×40 cm) devoid of any bedding. This open field was delineated into equal quadrants by tape on the underside of the cage. Animals were scored for motor activity by counting the number of quadrants traversed in 1 min. There was no significant difference between treatments on open field activity.

Olfactory Discrimination

Sixteen animals were treated with vehicle or 50 µg/kg Mox and tested for olfactory discrimination by measuring their latency to find hidden sunflower seeds (FIG. 5). The injections were counterbalanced with each animal receiving each treatment. Prior to testing animals were fasted for 24 hrs. Ninety minutes after injection animals were briefly taken from their home cage while six sunflower seeds were buried under the bedding in one corner. Animals were placed back into their home cage and scored for the latency to find the seeds in a ten min observation period. The latency to find the seed was significantly (p<0.001) reduced in animals treated with Mox as compared to vehicle controls. Surprisingly, all seeds were rapidly consumed in less than five min following treatment with Mox but not saline. In fact, not one of the sixteen animals consumed all of the seeds following saline as compared to all animals treated with Mox.

Sexual Activity

Figure 6A:
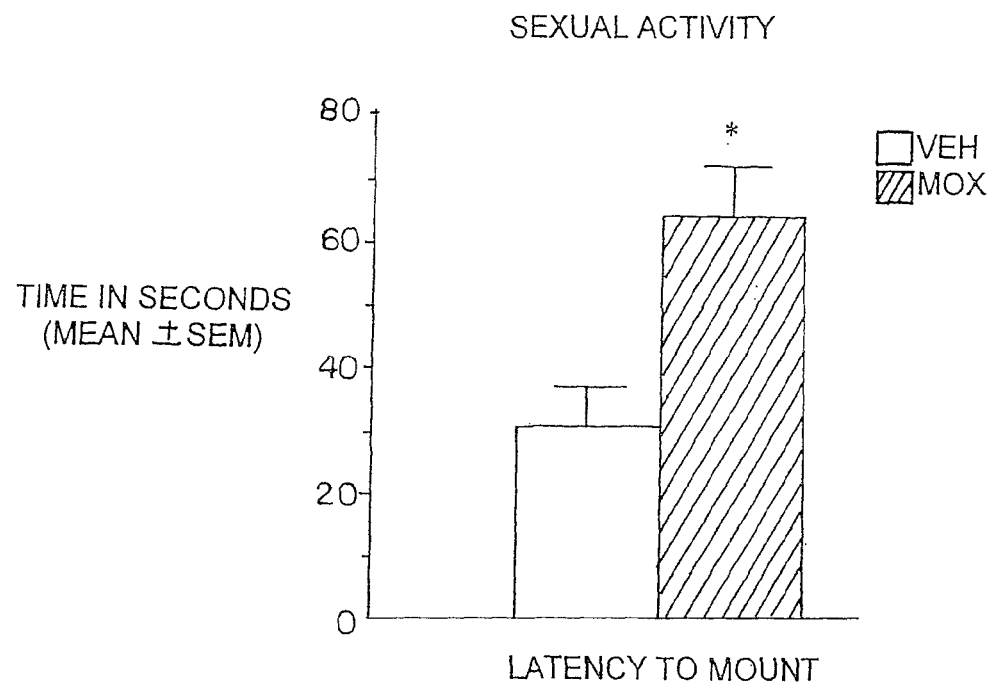
Figure 6B:
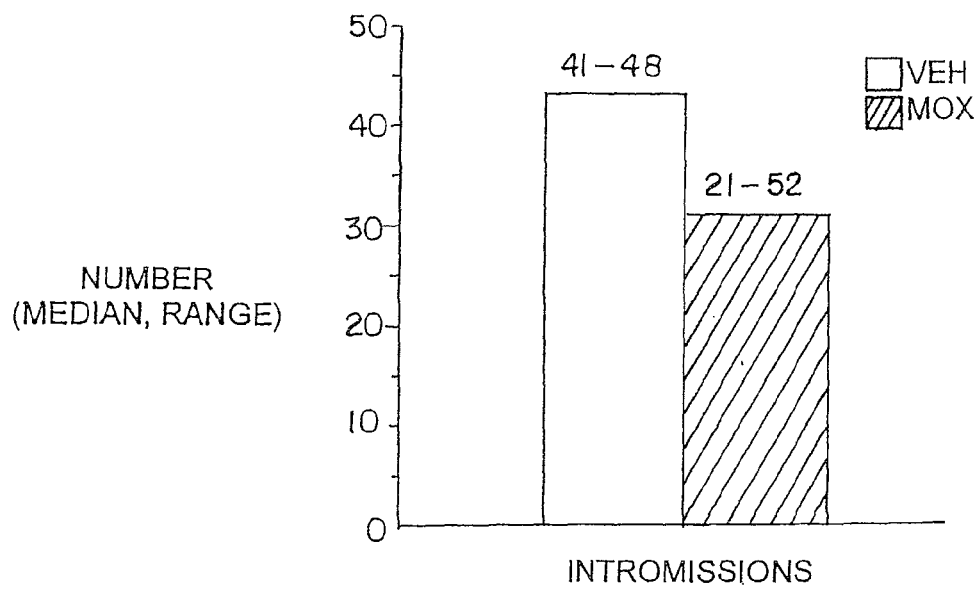

Six animals were tested over a five min observation period for sexual activity following treatment with saline vehicle or 50 µg/kg Mox (FIG. 6). The study was counter balanced with each animal receiving each treatment. Ninety min after injection, animals were scored for latency to mount and number of intromissions, i.e., bouts of copulation, toward a receptive female placed into their home cage. Female golden hamsters were ovariectomized under general anesthesia. Following recovery animals were treated with a single SC injection of 50 mg estradiol benzoate for three consecutive days to induce sexual receptivity. On the day of testing the estrogen primed females were introduced into the home cage of the experimental males. The first investigation by the males routinely caused robust lordosis in the female. Lordosis, is a stereotyped posture characterized by intense, sustained vertebral dorsiflexion.

Following vehicle treatment, animals mounted and thrust a receptive female in ca. 30 sec. The time to mount was significantly increased (p<0.05) following treatment with Mox. While both treatments showed high bout of copulation, animals treated with Mox showed a trend toward a decreased intromission rate (p<0.07).

Summary

Moxalactam appears to have a very good serenic profile. Serenics are drugs used to treat impulsivity and violence (Olivier and Mos, 1991). Serenics should suppress offensive aggression without interfering with social, appetitive and cognitive behaviors. Social interest in an intruder, i.e. contact time is not altered by Mox. Flank marking and activity in an open field is also unaltered with drug treatment evidence that general arousal and motor activity is normal. Fasted animals treated with Mox are better able to find hidden sunflower seeds evidence that drug treatment does not interfere with olfaction or motivation to find food; in fact, it may enhance it. Interestingly, Mox treatment reduced the latency to mount a receptive female and lessened, although not significantly, the bouts of copulation in a five min observation period. It should be noted that Mox treated animals were still very sexually active, except the behavior appeared less intense. This anti-aggressive effect of Mox combined with a mollification of sexual activity might have therapeutic value in treating violent sex offenders.

Development of eltoprazine, one of the first serenics, was abandoned, in part, because it was found to increase fear and anxiety in animals (Olivier et al 1994). To control for this possibility, it was necessary to test Mox in a model used to screen drugs for their affect on anxiety IV. Testing Moxalactam for Anxiolytic Activity Elevated Plus-Maze The elevated plus-maze was developed for the detection of anxiolytic and anxiogenic drug effects in the rat (Pellow et al., 1985). The method has been validated behaviorally, physiologically, and pharmacologically. The plus-maze consists of two open arms and two enclosed arms. Rats will naturally make fewer entries into the open arms than into the closed arms and will spend significantly less time in open arms. Confinement to the open arms is associated with significantly more anxiety-related behavior and higher stress hormone levels than confinement to the closed arms. Clinically effective anxiolytics e.g., chlordiazepoxide or diazepam, significantly increase the percentage of time spent in the open arms and the number of entries into the open arms. Conversely, anxiogenic compounds like yohimbin or amphetamines reduce open arm entries and time spent in the open arms.

Method

Male Wistar rats weighing 250-300 g were group housed in a normal 12:12 light-dark cycle light on at 0800 hr and provide food and water ad libitum. The plus-maze consisted of two open arms, 50×10 cm, and two enclosed arms 50×10×40 cm with an open roof, arranged such that the two open arms were opposite to each other. The maze was elevated to a height of 50 cm.

Figure 7A:
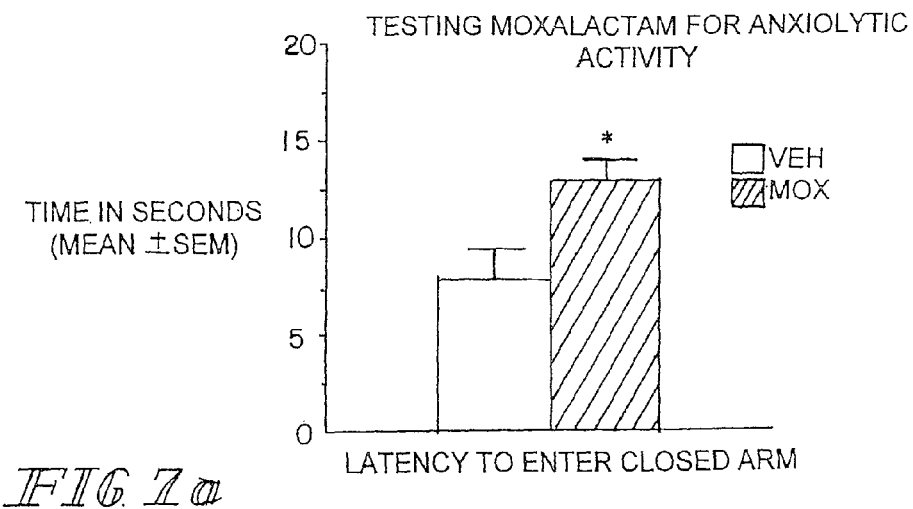
Figure 7B:
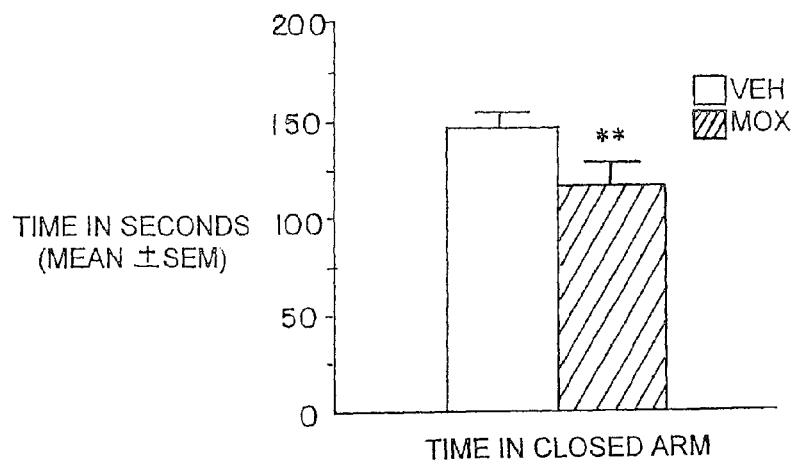
Figure 7C:
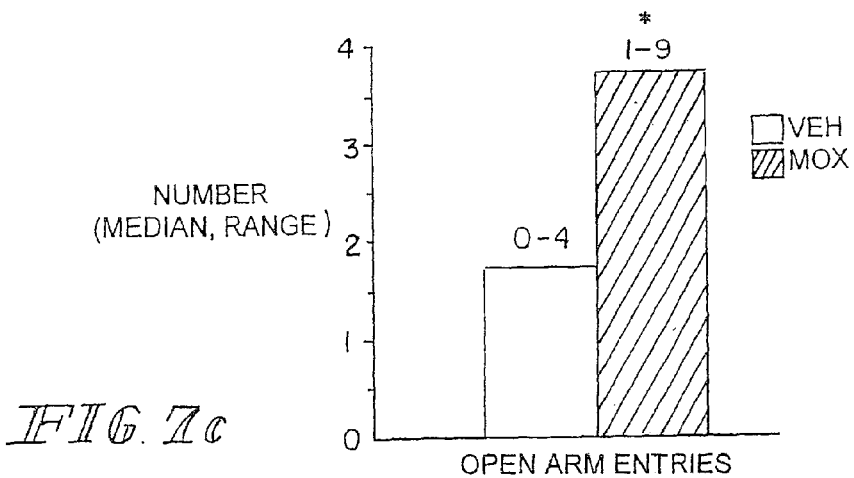

Eight animals were tested in the plus-maze 90 min following IP injection with 50 µg/kg Mox and saline vehicle. The order of treatments was counter balanced with at least 48 hrs between injections. At the start of the experiment the animal was place in the center of the plus maze facing the closed arm. Over a five min observation period, animals were scored for the latency to enter the closed arm, time spent in the closed arm and the number of open arm entries following the first occupation of the closed arm (FIG. 7). Treatment with Mox significantly increased the latency to enter the closed arm ($p<0.05$) as compared to vehicle. The time spent in the closed arm was significantly reduced ($p<0.01$), while the number of open arm entries was significantly elevated ($p<0.05$).

Summary

These data show Mox given at a dose of 50 µg/kg has anxiolytic activity. This finding enhances the serenic profile of Mox and delineates it from previous serenics like eltoprazine that suppressed offensive aggression, in part, by increasing fear and anxiety. These data also show that Mox may have therapeutic value as an anxiolytic However, the anxiolytic activity of Mox raises other concerns about behavioral specificity. Many anxiolytics, particularly the benzodiazepines are sedatives and can depress general motor activity and may also acts as amnesics and interfere with learning and memory. Since Mox was show to have no effect of flank marking or activity in an open field it is unlikely to act as a general sedative. However, it was necessary to test Mox for any untoward effects on learning and memory.

V. Testing Moxalactam for Anxiolytic Activity

Moxalactam v. Chlordiazepoxide

Methods

Because Mox and CDP have different bioavailability profiles, e.g. brain penetrance, their CNS activity could not be compared by giving systemic injections of equimolar concentrations of each drug. Instead it was necessary to give both drugs directly into the cerebroventricular system to by pass the blood brain barrier. Animals were anesthetized with sodium pentobarbital (50 mg/kg), implanted with microinjection guide cannulae aimed at the lateral ventricle and allowed to recover for two days before testing. To groups of six animals each were tested with Mox or CDP. Each animals received a injection of drug and 0.9% NaCl vehicle on two separate days. The order of injections was counterbalanced and separated by two days. Both Mox and CDP were prepared in 0.9% NaCl at a concentration of 1 mM. All injections were given in a volume of 2 ul over 10 secs in fully conscious, restrained animals. Sixty min later animals were tested in the plus-maze for a 3 min observation period and scored for behaviors as noted previously.

Results

Figure 17A:
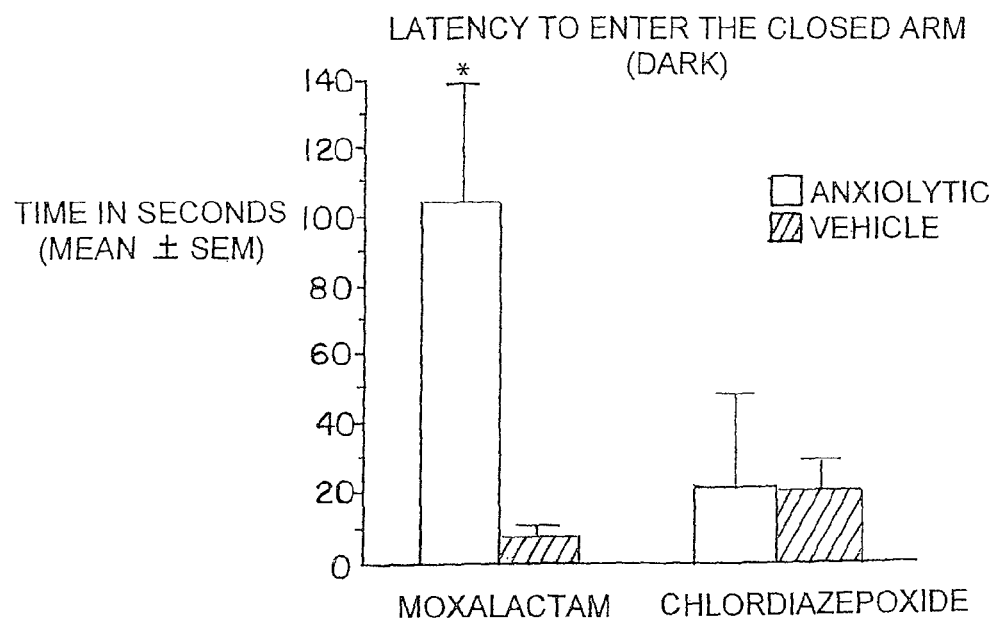
Figure 17B:
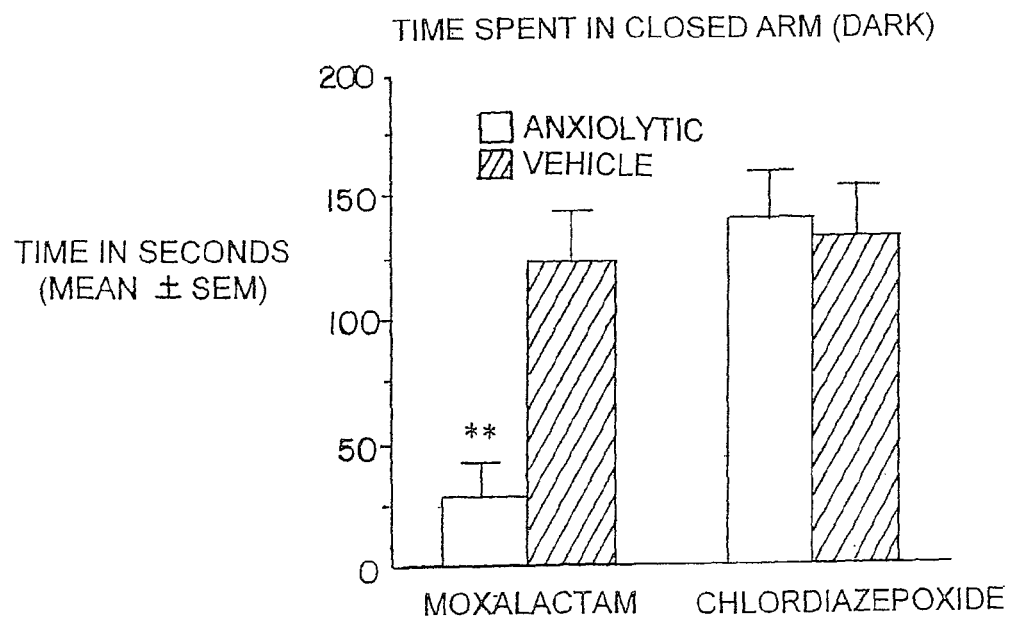

Mox treatment significantly ($p<0.05$) delayed the time it took to enter the closed arm as compared to vehicle treatment (FIG. 17). Treatment with Mox caused animals to spend most of their time in the light arms of the plus-maze. Time spent in the dark was significantly ($p<0.01$) lower following Mox treatment as compared to vehicle. Treatment of CDP at the 1 mM concentration had no effect on either the latency to enter the closed arm or time spent in the closed arm as compared to vehicle treatment.

Controlling for Non-Specific Depression of Motor Activity

Figure 18:
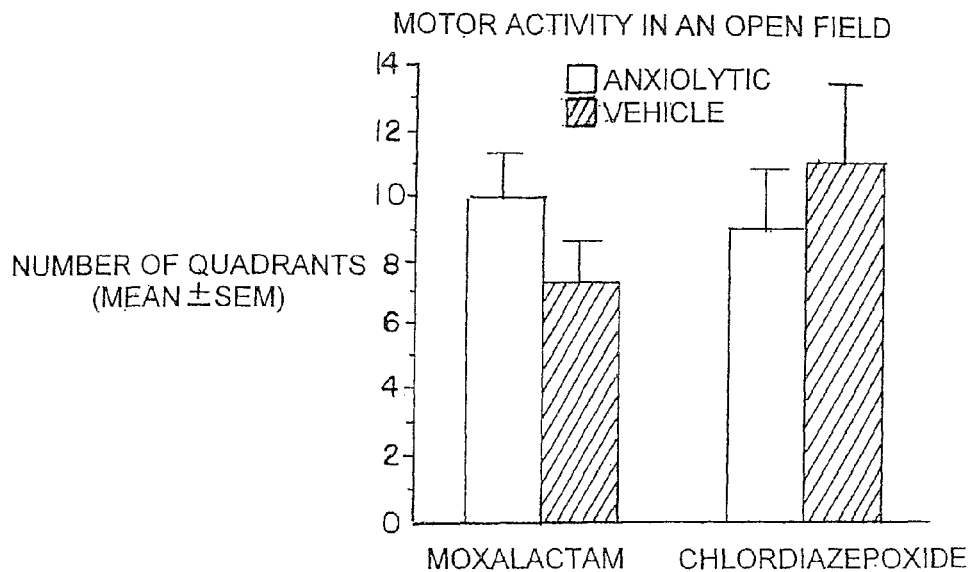

When CDP is given systemically to rodents in doses of 5-15 mg/kg it is a sedative and depresses motor activity. However, this depression of motor activity disappears following repeated administration of CDP over several days. Only after the animals become insensitive to the motor effects of CDP are they tested in the plus maze for anxiolytic activity. To control for any non-specific effects of Mox and CDP on motor activity following their direct injection into the brain, animals were tested in the open field 30 min prior to testing in the plus (FIG. 18). There was no significant effect for either anxiolytic on general motor activity.

Summary

The finding that Mox is an anxiolytic enhances its serenic profile and delineates it from previous serenics like eltoprazine that suppressed offensive aggression, in part, by increasing fear and anxiety. On an equimolar basis, Mox showed anxiolytic activity given directly into the brain as compared to CDP which had none. These data show that Mox may have therapeutic value as an anxiolytic in addition to a serenic.

However, the anxiolytic activity of Mox raises other concerns about behavioral specificity. Many anxiolytics, particularly the benzodiazepines are sedatives and can depress general motor activity and may also acts as amnesics and interfere with learning and memory. Since Mox was show to have no effect of flank marking or activity in an open field it is unlikely to act as a general sedative. However, it was necessary to test Mox for any untoward effects on learning and memory.

VI. Testing Moxalactam for Spatial Memory

Radial Arm Maze

The radial arm maze is one of the most commonly used methods for testing spatial learning and memory in rodents. Developed by Olton and co-workers (1976), it provides the simultaneous choice of several alternative paths for the test subject. Animals must learn which locations provide food (place learning) using visuospatial cues.

Methods

Experimental Trials: The experimental trials consist of three phases (described below). The arms of the maze are numbered clock-wise from one to seven with arm number one being the arm furthest to the right side of the maze. All trials are ca. 12 min long. When not being tested, all hamsters have unlimited access to water. In addition to the sunflower seeds in the maze, hamsters are given one Agway Prolab 3000 food pellet daily. Trials within all the phases are conducted on successive days.

Phase One: Phase One consists of five 15 min trials. Prior to the beginning of each of the five trials in Phase One, four sunflower seeds are placed at the ends of arms one, two, and three. Arms four, five, six, and seven remain empty.

Phase Two: Phase Two of the experimental trials are identical to Phase One except that the seeds are placed in arms two, four, and seven. Arms one, three, five and six remain empty. Phase Two consists of four 15 min trials.

Phase Three: Phase Three of the experimental trials consists of three 15 min trials, with arm two, four, and seven baited with sunflower seeds. Phase Three differ form Phase Two in that the maze is rotated clockwise in the room 110°.

Coding of Behaviors: An arm entry was scored if all four paws of a hamster crossed an arm threshold. A full arm entry into an arm is scored if a hamster's snout touches the top of the block at the end of an arm or if their snout passes the block. These scores were made for baited and unbaited arms. In addition, the number of seeds pouched by the hamsters was scored.

Results

Figure 8A:
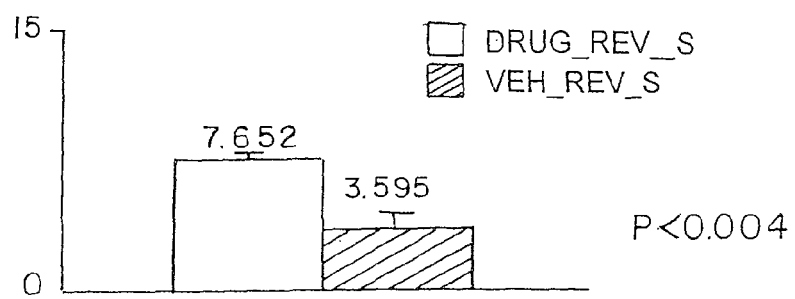
Figure 8B:
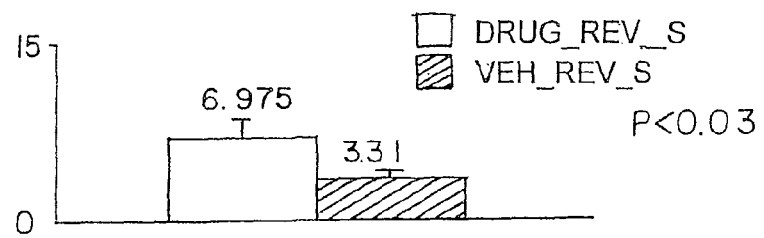
Figure 8C:
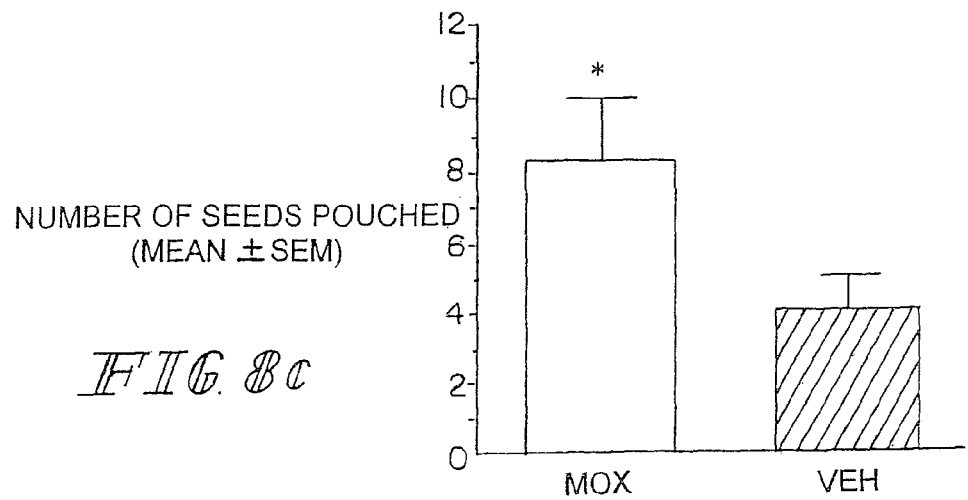

Six male hamsters were tested in the radial arm maze following treatment with 0.9% NaCl or 50 µg/kg Mox (FIG. 8). Each animal received each treatment and the order of treatments was counter balanced. The most critical measure in the radial arm maze is the number of seeds discovered after reversing the orientation of the maze on the final day of testing. Moxalactam treatment significantly increased seed finding (p<0.01) as compared to vehicle treatment.

Summary

These data support the notion that the anxiolytic profile of moxalactam is not accompanied by any disruption in learning and memory as is the case with benzodiazepine anxiolytics. On the contrary, moxalactam enhances spatial memory would may act as a psychotropic agent to improve cognitive performance. This finding suggests that moxalactam may be an effective therapeutic agent for the treatment of ADHD and conduct disorder in children and senility in geriatric patients.

Spatial Navigation in Water Maze

The Morris water maze like the radial arm maze was developed to test spatial memory (Morris, 1984). The pool is divided into quadrants usually designated North, South, East and West. The water in the pool is made opaque with milk powder. Hidden just beneath the surface in one of the quadrants is a platform that serves as a escape route for rodents placed into the pool. An animal is placed some where in the pool from a variety of different start points and is timed for latency to find the platform, percent time spent in each quadrant, distance traveled and swimming speed. The animals has no visual or spatial cues in the pool and must rely on extra-maze cues, i.e., objects set up outside the pool that can be seen by the swimming animal. Through a series of trials a rat develops "place learning" or knowledge about the position of the platform based upon the extra-maze cues. The platform can be moved to a different quadrant each day combining spatial memory with working memory. This paradigm involves extinction of the prior memory and resolution of a new spatial problem.

Methods

The water maze consisted of a black plastic circular pool ca. 150 cm in diameter and 54 cm in height filled to a level of 35 cm with water made opaque with powdered milk. The pool was divided into four quadrants with a platform 10 cm in diameter submerged 2 cm below the surface in the northwest quadrant. The water was maintained at a temperature of 25° C. Around the pool were several visual cues. Above the pool was a video camera for tracking the movement of the experimental animal. The data collection was completely automated using the software developed by HVS Image (Hampton, UK). Before testing, rats were familiarized with the pool and platform placed in the northwest quadrant. Each day for 4 consecutive days, animals were placed into pool at random sites and given two min to find the platform. Animals were treated one hr before testing with 50 µg/kg Mox (n=11) or vehicle (n=10). Following these familiarization trials, animals were tested for spatial navigation. The first day of testing began with the platform in the expected northwest quadrant. All behavior was videotaped for a two min observation period. After testing the animal were dried off and placed back into their home cage. On each subsequent day the platform was moved to a new quadrant and the rat started at different positions. The rat was always placed into the pool facing the side wall. The start positions relative to the platform were different for each of the four trials; however, the platform was always in the same relative position in each quadrant. Twenty cm in from the side of the pool and in the left corner from the center facing out.

Results

Figure 19A:
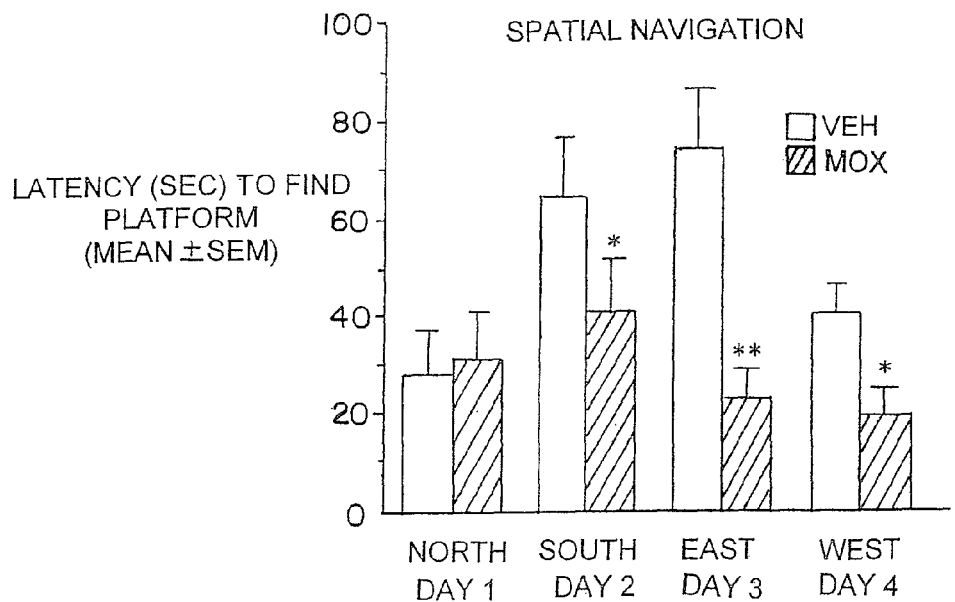
Figure 19B:
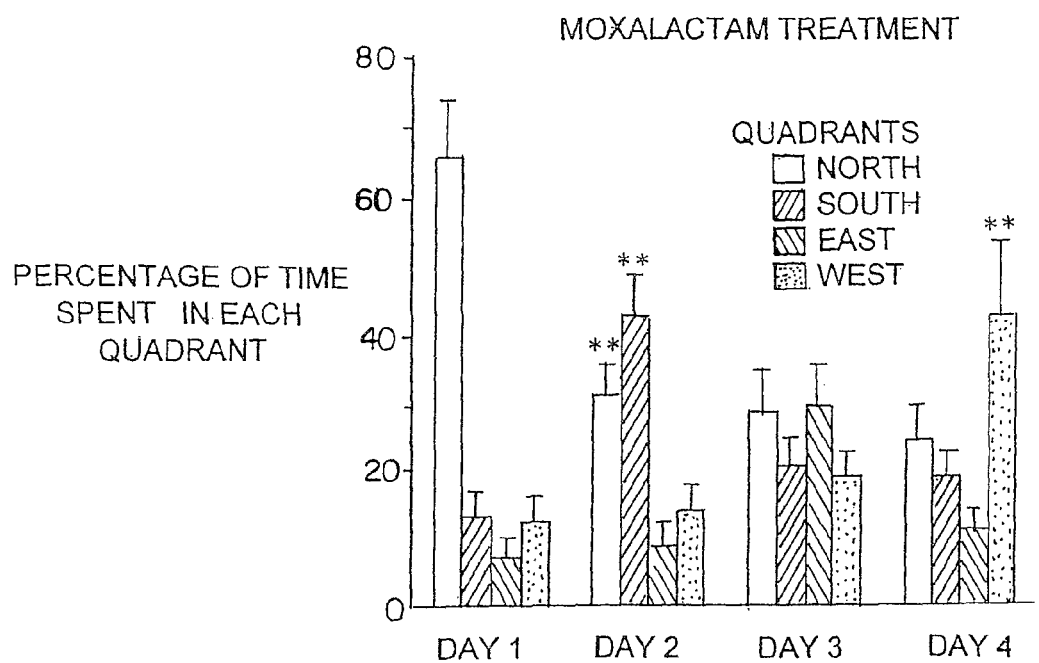
Figure 19C:
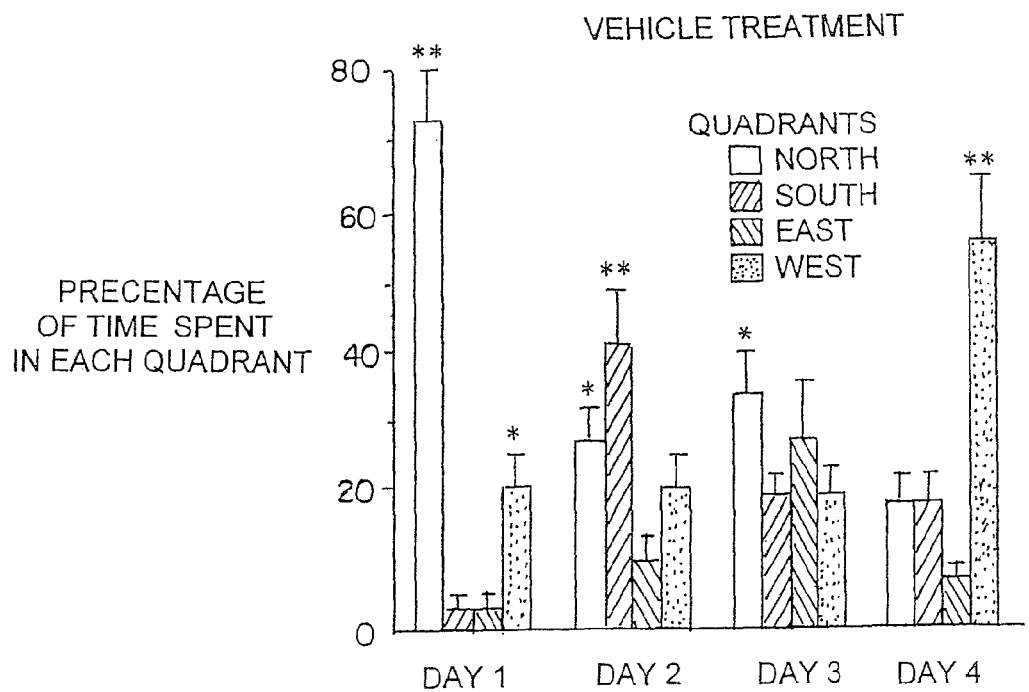

A two-way ANOVA showed a significant main effect for treatment ($F_{(1,20)}$=6.48, p<0.05) and days of testing ($F_{(3,63)}$=5.76, p<0.01) (FIG. 19). There was also a significant interaction between treatments and testing days ($F_{(3,63)}$=4.35, p<0.01). Newman-Keuls post hoc tests showed a significant difference between treatments on day two (p<0.05), day three (p<0.01) and day four (p<0.05) (FIG. 19). On each of these days Mox treated animals showed significantly shorter latencies to find the hidden platform than the vehicle treated group. Indeed, vehicle treated animals showed a significant increase in latency on days 2 (p<0.05) and 3 (p<0.01) as compared to day 1.

The strategy for finding the platform was strikingly similar for both treatments (FIG. 19, lower two graphs) as judged by the percentage of time the animals spent in each quadrant. For any quadrant on any day there was no significant difference between treatments. There was a significant difference between days for percentage of time spent in any particular quadrant (e.g., North, $F_{(3,63)}$=28.80, p<0.0001). Animals spent a significant portion of their time in certain quadrants on certain days. For example, on Day 1 both Mox and Vehicle animals spent most of their time in the North quadrant as compared to the other quadrants (p<0.01). This was to be expected since they had knowledge of the location of the platform in this quadrant from the familiarization procedure.

Interestingly, Vehicle animals also showed a significant ($p<0.05$) amount of time in the West quadrant on Day 1 as compared to South and East. This was probably because the platform was hidden in the northwest part of the North quadrant. On Day 2, Mox and Vehicle animals spent a significant amount of time in both the North and South quadrants as compared to East and West. On Day 3 Mox animals show no particular bias for any quadrant while Vehicle animals still show a significant interest in the North quadrant as compared to South and West. By Day 4 both Mox and Vehicle spent most of their time in the correct quadrant (West) with the least amount of time in the East quadrant where the platform was hidden the day before. This strategy on Day 4 shows good spatial, working and procedural memory for both treatments.

Figure 20A:
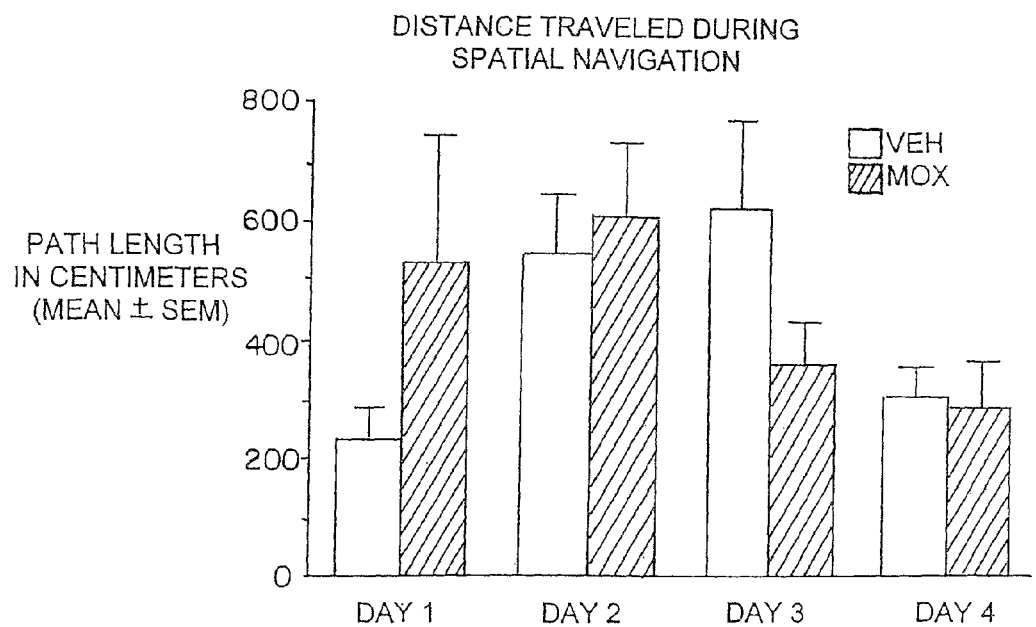
Figure 20B:
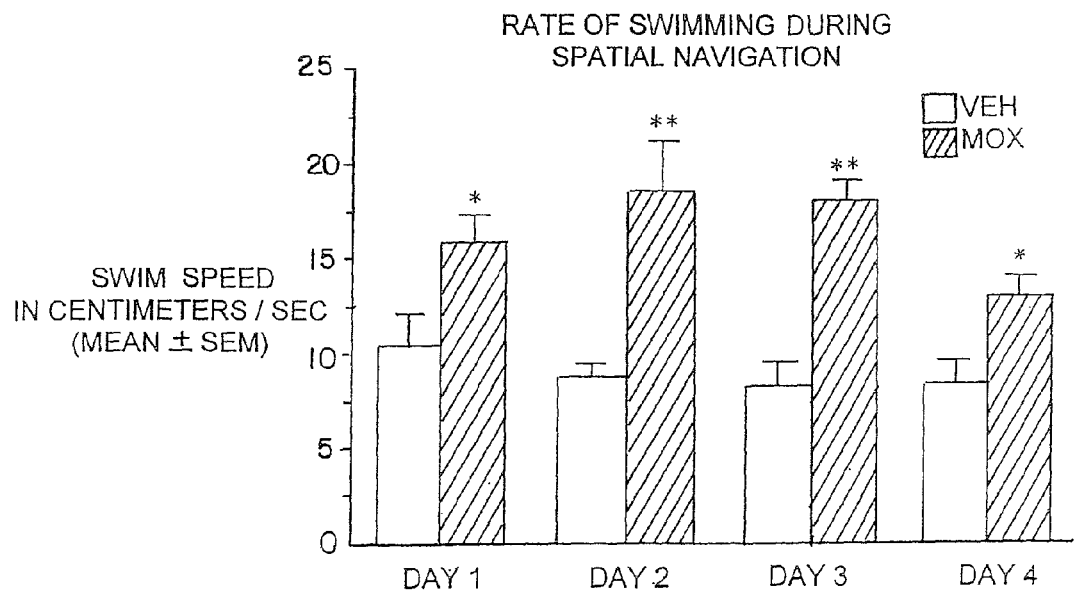

The distance covered to reach the platform across days was not significantly different between Mox and Vehicle animals (FIG. 20). However, Mox animals showed significantly greater swim speed than Vehicle animals ($F_{(1,20)}=22.94$, $p<0.0001$)(FIG. 20). For example, on Day 2 both groups traveled a similar distance to the platform except Mox animals covered the distance at almost twice the speed ($p<0.01$). While there was no main effect across days ($F_{(3,63)}=2.27$, $p<0.09$) there was an interaction between swim speed and days ($F_{(3,63)}=2.75$, $p<0.05$) for Mox treatment as this group decreased their swim speed over time.

Cue Navigation in Water Maze

Method

Figure 21A:
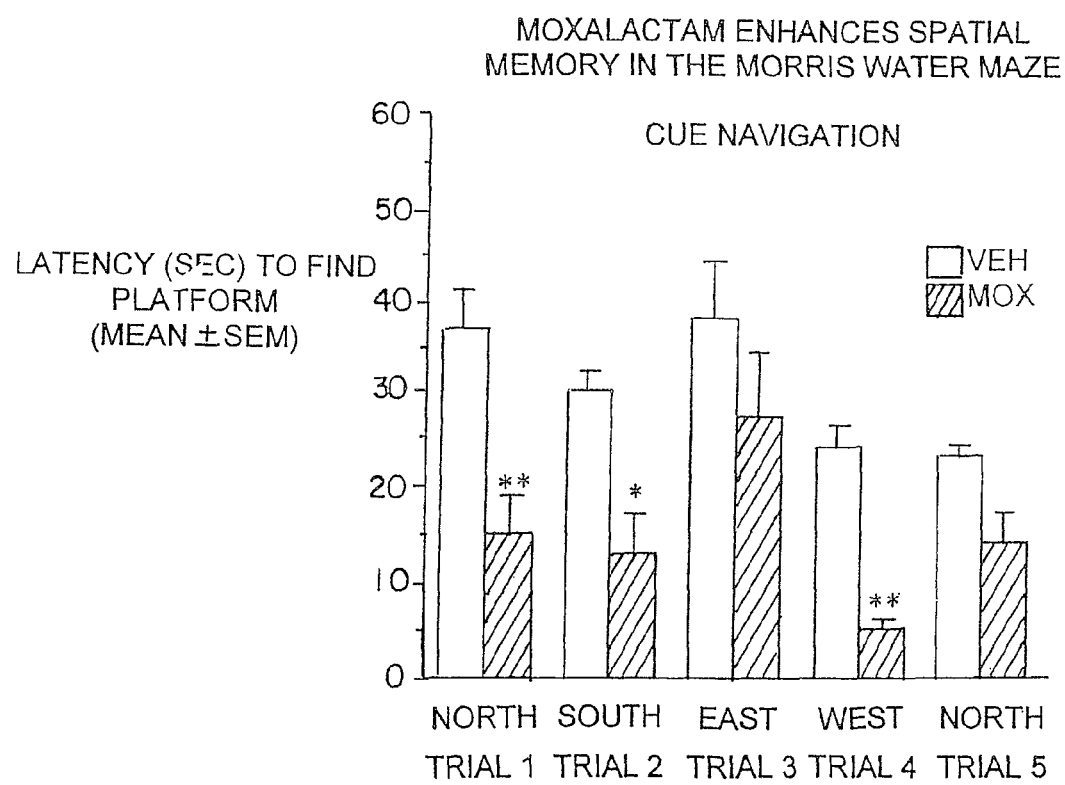
Figure 21B:
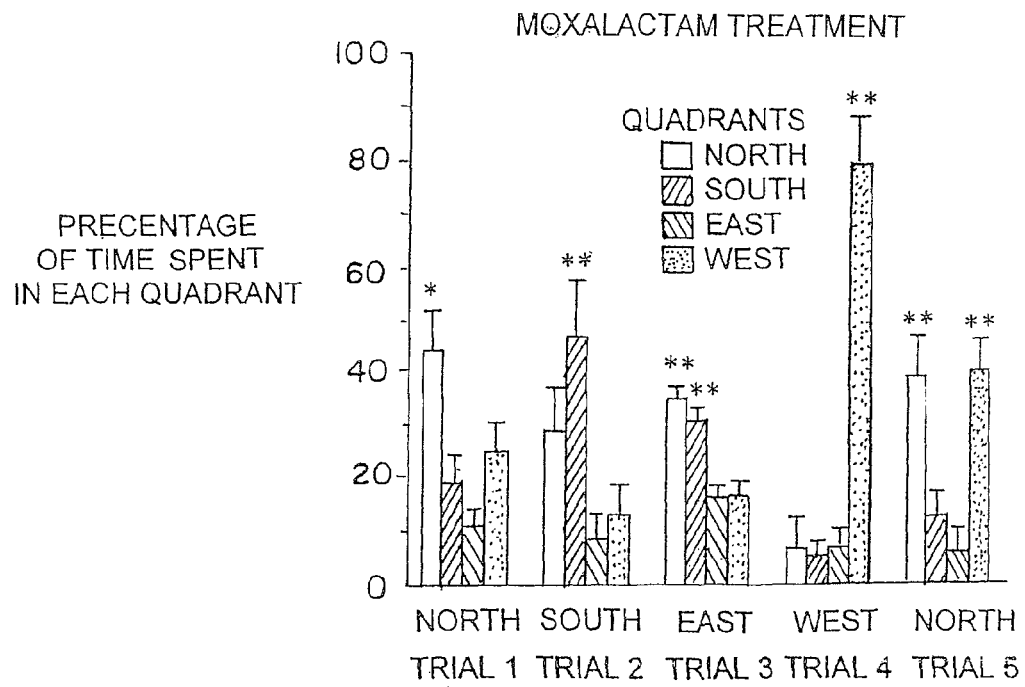
Figure 21C:
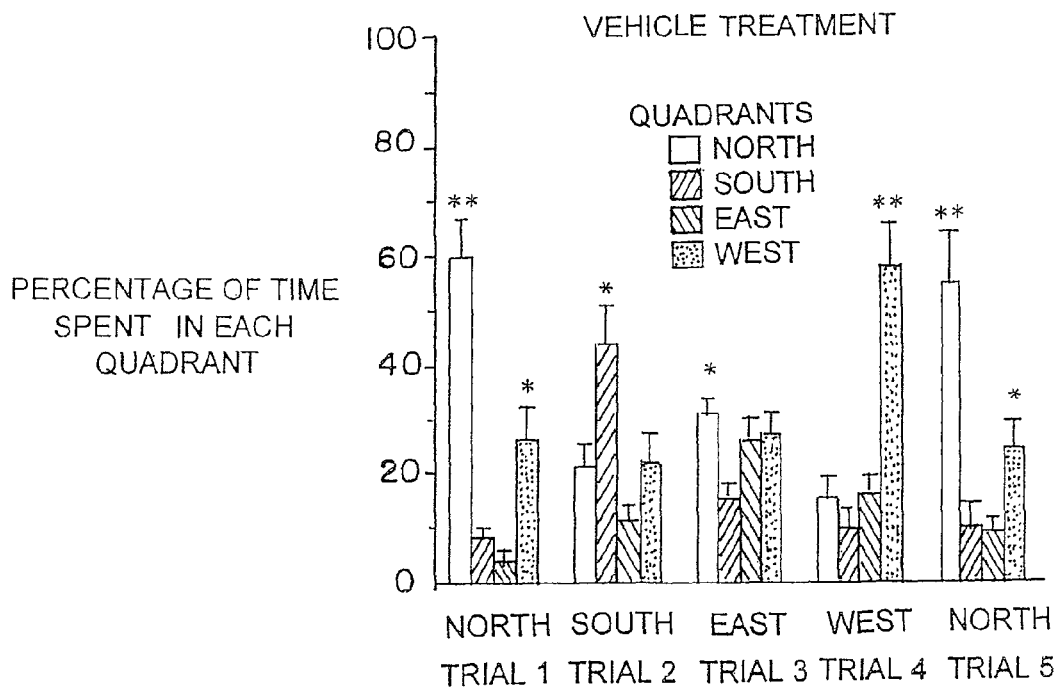

On the day following the last day (Day 4) of spatial navigation, animals were tested for cue navigation. In these tests, the platform was raised above water level. One hr before testing animals were treated with Mox or saline vehicle. The same animals that were treated with Mox during spatial navigation were treated with Mox for cue navigation. Animals were run through a series of two minute trials with 45 min between trials. At each trial, the platform was moved to a different quadrant. The cue navigation study was identical to the spatial navigation except the platform was visible and the testing was done over five consecutive trials done on a single day. Animals were scored for latency to find the platform, percent time spent in each quadrant, path distance and swim speed for all testing periods Results The latency to find the platform was different between Mox and Vehicle treated animals ($F_{(1,20)}=24.68$, $p<0.0001$) (FIG. 21). There was also a main effect for days ($F_{(4,84)}=6.53$, $p<0.0001$) but no interaction between treatment and days ($F_{(4,84)}=0.99$, $p<0.4$). On trials 1,3, and 4 Mox animals showed significantly shorter latencies than Vehicle animals.

As in spatial navigation, the strategy for finding the platform was very similar for both treatments (FIG. 21, lower two graphs) as judged by the percentage of time the animals spent in each quadrant. For any quadrant on any trial there was no significant difference between treatments (e.g., South, $F_{(1,20)}=1.61$, $p<0.21$). There was a significant difference between trials for percentage of time spent in any particular quadrant (e.g., South, $F_{(4,84)}=16.70$, $p<0.0001$). Animals spent a significant portion of their time in certain quadrants on certain trials. For example, on Trial 5 both Mox and Vehicle animals spent a significant amount of time in the North quadrant were the platform was hidden, and the West quadrant were the platform had been on the previous trial.

Figure 22A:
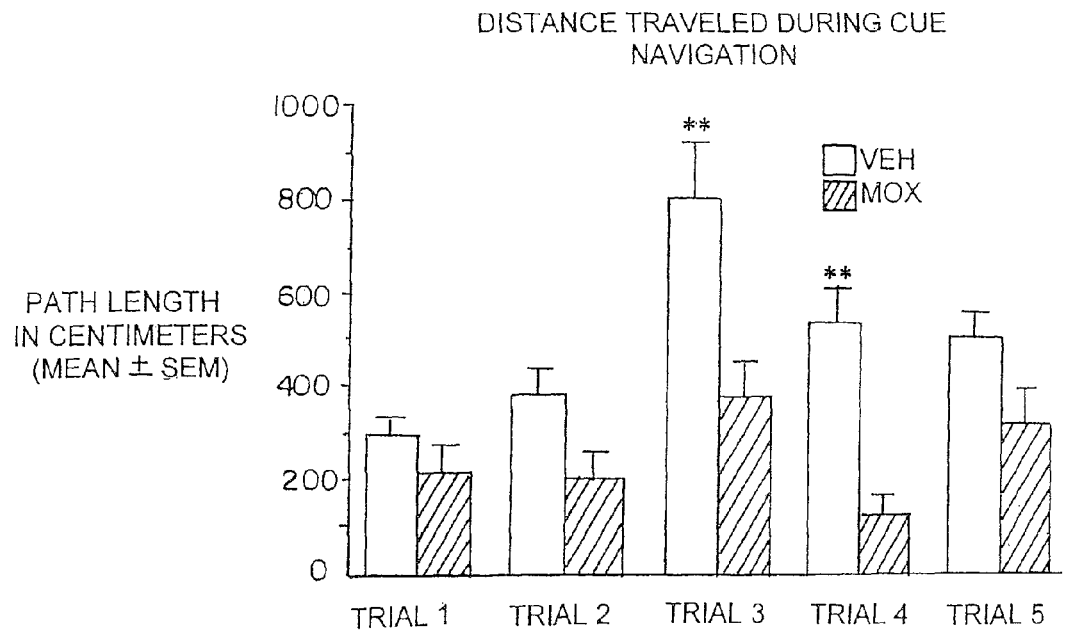
Figure 22B:
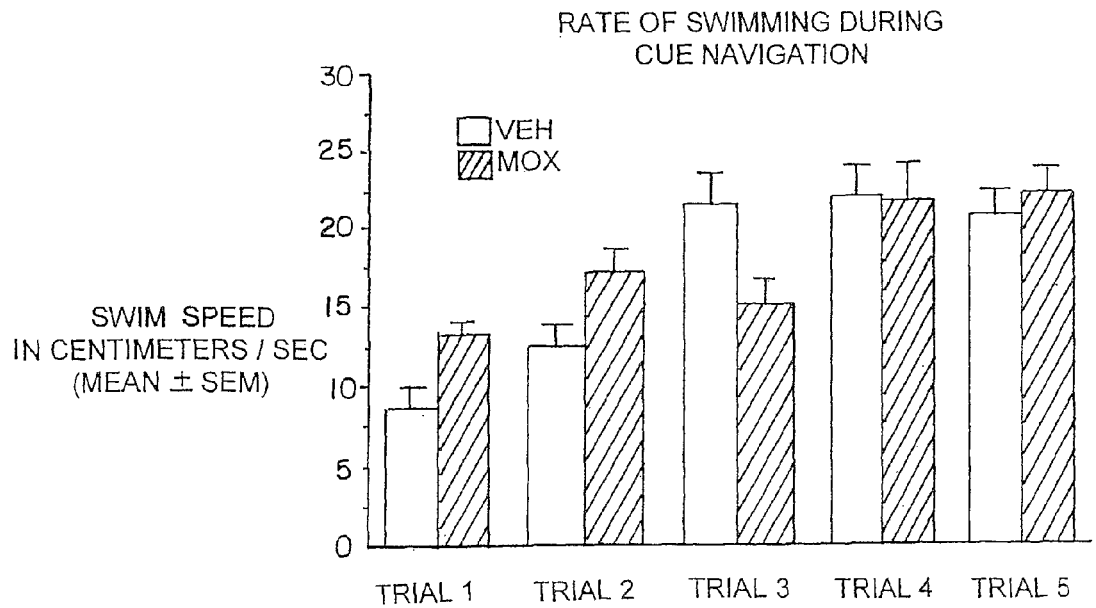

Unlike spatial navigation, the distance traveled during cue navigation was significantly different between Mox and Vehicle animals ($F_{(1,20)}=44.11$ $p<0.0001$) (FIG. 22). There was also a significant main effect for trials ($F_{(4,84)}=7.90$, $p<0.0001$) and interaction between treatment and trails ($F_{(4,84)}=2.67$, $p<0.05$). On Trial 1 there was no difference in path length between treatments. However, on Trials 3 and 4 Vehicle animals traveled significantly farther to find the platform than Mox animals. The path length did not significantly change across trials for Mox animals. Whereas, the mean path length on Trial 3 for Vehicle animals was significantly greater than any other trial for this treatment.

Unlike spatial navigation, there was no significant difference in swim speed between the two treatments ($F_{(1,20)}=0.67$, $p<0.42$) (FIG. 22). However, there is a main effect across trials ($F_{(4,84)}=17.18$, $p<0.0001$) and an interaction between treatment and trials ($F_{(4,84)}=4.10$, $p<0.01$). In both treatments there is a significant increase in swim speed over each subsequent trial. For example, from Trial 1 to Trial 4 Mox and Vehicle animals showed a significant increase in swim speed ($p<0.01$).

Summary

Figure 23:
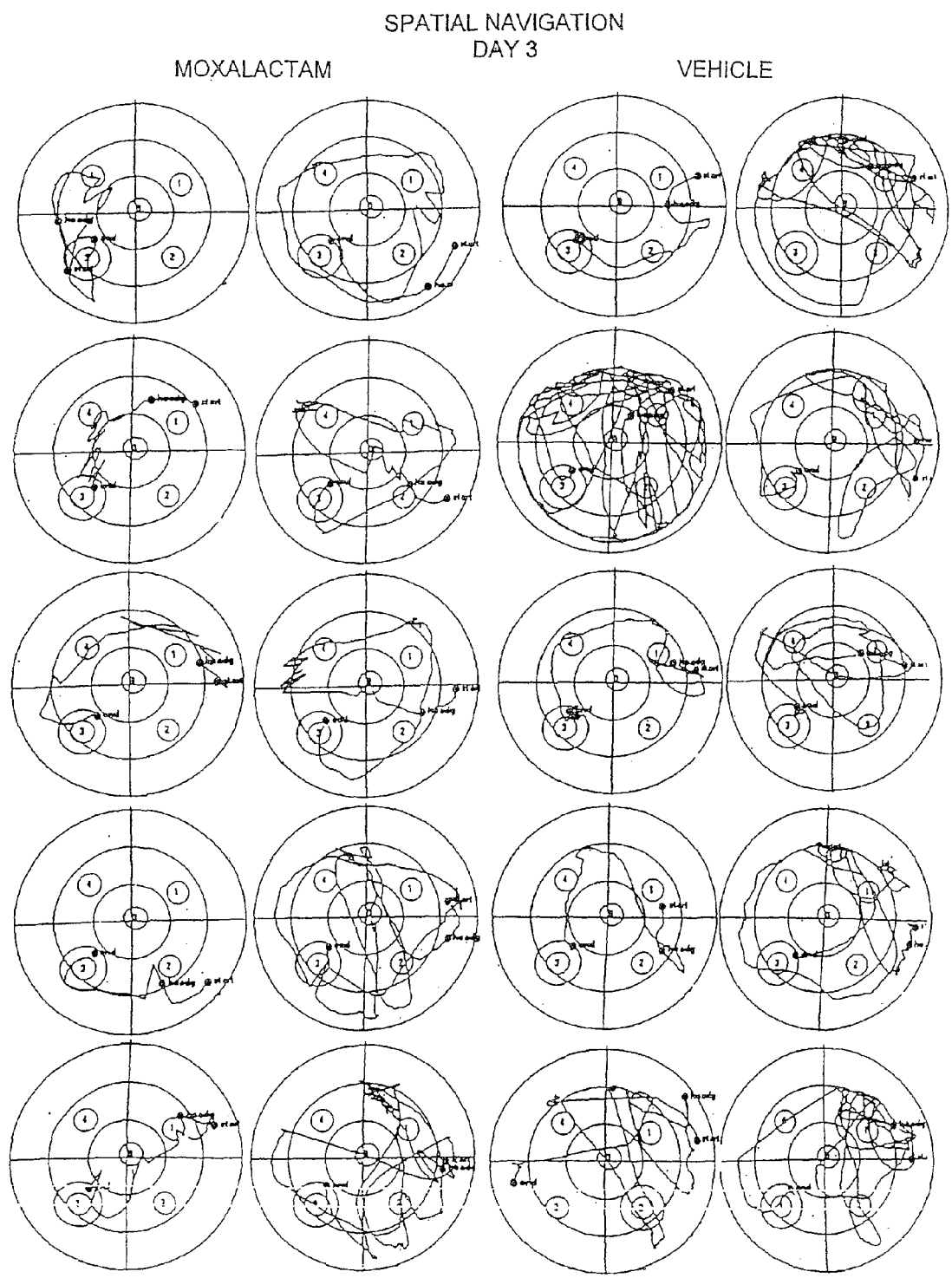
Figure 24:
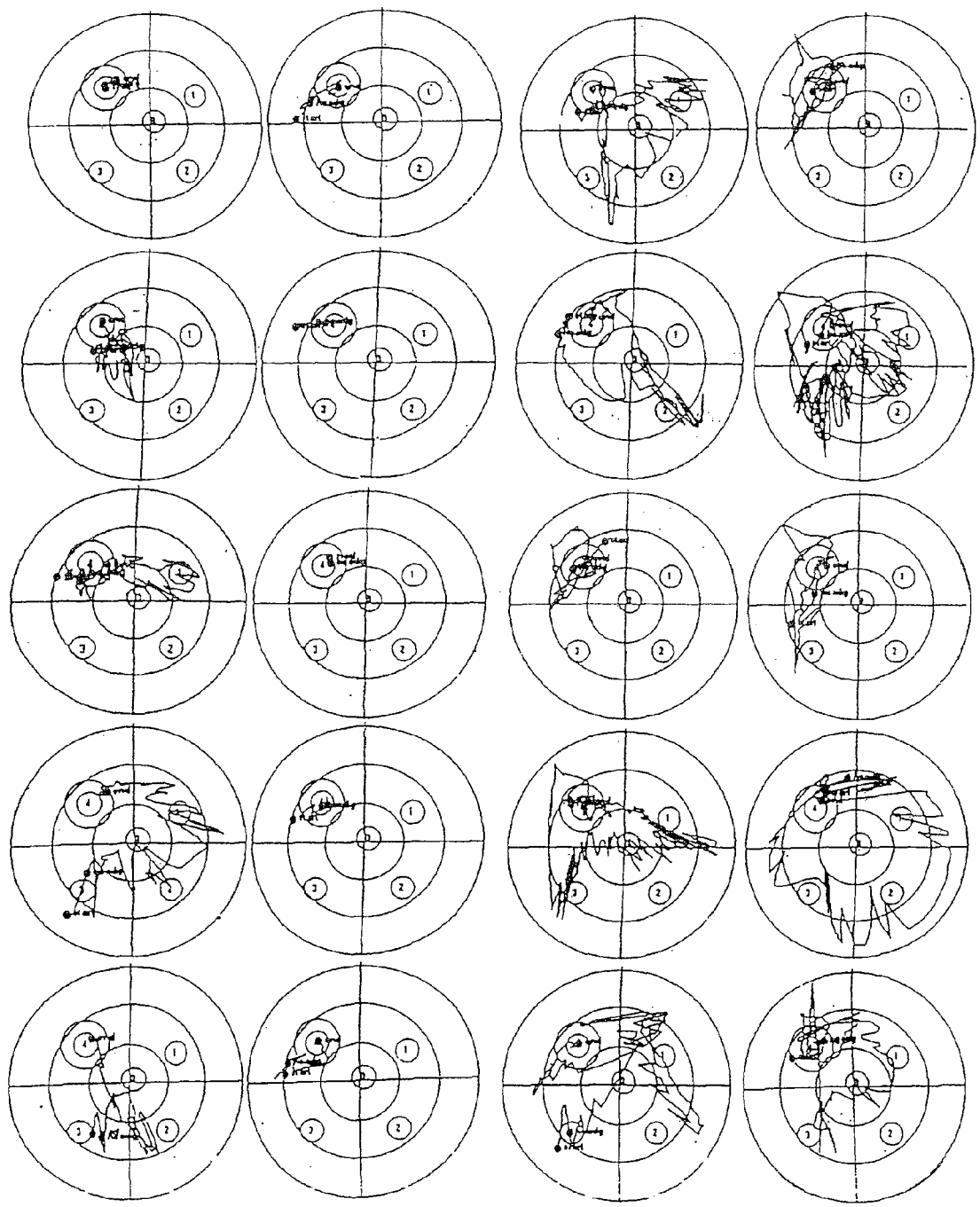

Moxalactam treated animals are more effective in finding the hidden and visible platform in the water maze than vehicle treated controls. However, the strategy for success in each navigation paradigm was strikingly different. During spatial navigation, animals must rely on extramaze cues and procedural memory to find the moving platform. Mox and vehicle animals appeared to show the same learning and memory as there was no difference in the percentage of time spent in each quadrant for each day of testing. There was no ostensible difference in the swim patterns (FIGS. 23 and 24). The distance traveled between treatments was not significantly different. Mox animals found the platform sooner, in part, because they swam faster. However, cue navigation presented a different profile. Again Mox treated animals out performed vehicle animals on latency to find the platform. Again the search strategy as defined by the percentage of time spent in each quadrant was strikingly similar. However, unlike spatial navigation, animals treated with Mox showed a much shorter path length. Moreover, both treatment groups swam at the same speed.

These data support the notion that the anxiolytic profile of moxalactam is not accompanied by any disruption in learning and memory as is the case with benzodiazepine anxiolytics. On the contrary, moxalactam enhances spatial memory and may act as a psychotropic agent to improve cognitive performance. This finding suggests that moxalactam may be an effective therapeutic agent for the treatment of ADHD and conduct disorder in children and senility in geriatric patients.

VII. Social Behavior in Non-Human Primates

Experimental Procedure

Eight, two year old adolescent male rhesus macaques were tested with Mox. Animals were raised with their mothers in a group setting at a field station. At one year of age, they were transferred to individual cages. Each day thereafter, they were paired housed for two-three hrs. The adolescent partners were always the same. This year long procedure resulted in adolescent partners or "play-mates" having a well-defined history of social interaction with recognizable dominant and subordinate status. The display of social behaviors in this arrangement are very robust because of the limited amount of time the monkeys spend together.

During the experiment the monkeys were paired in the "play-cage" where they were video taped for one hour. The study was designed so that behavioral data were obtained for each monkey under Mox and vehicle treatment. The treatment was an ABA type schedule of administration: Day 1—one member of each pair received 0.9% NaCl vehicle, Day 2—drug, Day 3—vehicle. Only one member of a pair was injected on a test day. The other member of a pair was injected a week later according to the same ABA schedule. Moxalactam was injected IM in a dose of 1 mg/kg. Animals were video taped sixty minutes after injection for a one hr observation period. Animals were scored for over forty different behaviors (Winslow et al., 1988). Only twenty-eight are listed on TABLE I. The unreported behaviors, e.g., self-bites, vocalizations, clinging, mounts, escapes, self grooming were so infrequent that they were omitted from the analysis. Paired t-test was run for each behavioral measure.

Results

The duration of play fighting was significantly reduced (p<0.05) by Mox treatment as compared to vehicle. This finding was not affected by the social status of the animal, i.e. both dominant and subordinate animals showed diminished play fighting following treatment with Mox. Interestingly, several different measures of agonistic behavior, e.g., composite aggression scores, clustered together at near significant levels. It should be noted that these are juvenile rhesus monkeys, and as such their expression of social aggression is primarily confined to play fighting. The aggression does not have the same emotional valence as adults. Nonetheless play fighting is thought to be the juvenile antecedent to adult aggression. Allogrooming for adolescent and adult monkeys is the primary measure of affiliative behavior. While Mox significantly reduced the duration of play fighting it had no effect on allogrooming.

Summary

Moxalactam given in a dose of 1 mg/kg to adolescent rhesus monkeys significantly reduces play fighting a measure of agonistic behavior. However, allogrooming the key measure of affiliative behavior is unaltered. Hence the finding that Mox can reduce agonistic behavior in rodents translates to non-human primates.

VIII. Testing D and L Isomers of Moxalactam

Rationale

The 3D structure of drugs can naturally occur as mirror images or isomers. These isomers are classified as D or L based on their rotation of light. Only one of the isomers usually has biological activity. Since the preparation of Mox used in these studies is a mixture of the two isomers it was necessary to isolated and test for the active isomer.

Methods

Moxalactam sodium salt (FW 564.4) was obtained as a mixed isomer from Sigma Chemical (St Louis Mo.). D, L-Mox were isolated with HPLC using the method outlined by Ziemniak et al., 1982. D,L-Mox was taken up in water and fractioned on a C18 column with a running buffer of 1% MeCN, pH 6.5. Column effluent was monitored at 275 nm with a UV detector. Both isomers came out as single peaks. D Mox had a retention time of 6.7 min while L-Mox came out at 8.2 min. The individual isomers of Mox provided to be relatively unstable and would rapidly re-isomerize during lyophilization making it difficult to have a reasonably pure (>98%) sample. Hence it was necessary to go directly from the HPLC to the animal. D isomer (ca. 200 µg/ml HPLC buffer) was diluted to 50 µg/ml saline and keep on ice until IP injection (50 µg/kg). L isomer (ca. 150 µg/ml HPLC buffer) was also diluted to 50 µg/ml saline and treated similarly.

Results

Figure 9A:
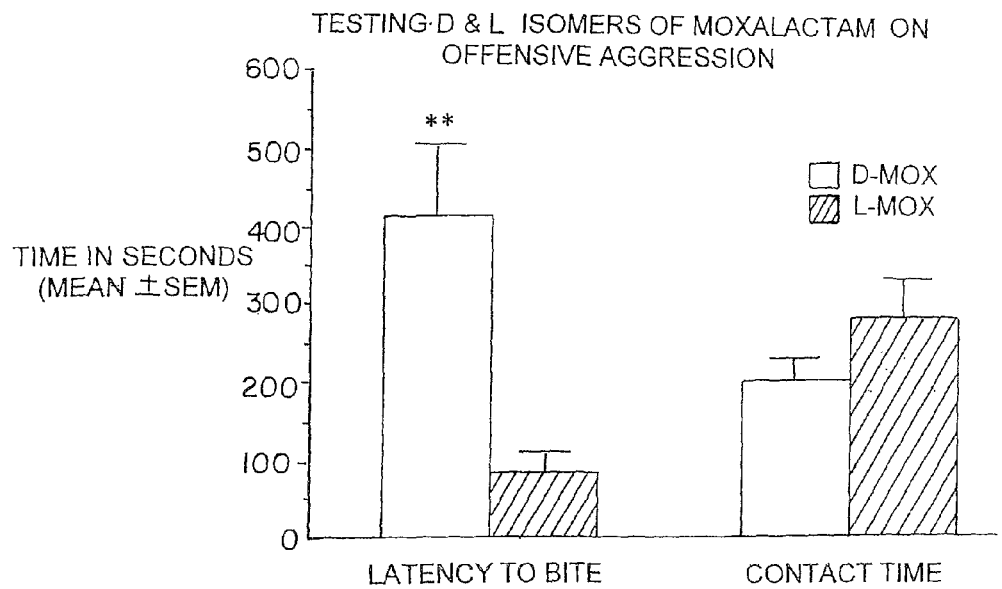
Figure 9B:
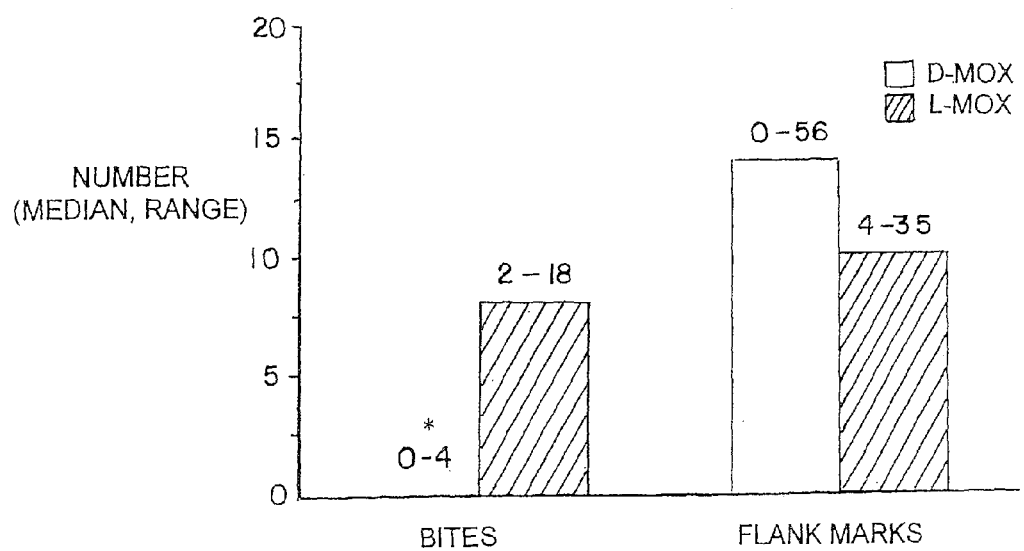

Two groups of eight animals each were tested for offensive aggression following treatment with 50 µg/kg D or L Mox (FIG. 9). Animals were tested 90 min after injection. D Mox significantly increased bite latency (p<0.01) and reduced the number of bites (p<0.05). There was no significant difference in contact time or flank marking between the two isomers.

Summary

These data identify D moxalactam as the active isomer affecting offensive aggressive behavior.

IX. Testing Beta-Lactam Related Antibiotics for Antiaggressive Effects Rationale Moxalactam is chemically and pharmacologically similar to cephalosporin and penicillin antibiotics. Indeed, moxalactam is classified as a cephalosporin. The basic structures of all cephalosporins and penicillin are show below. Each has a beta-lactam ring (A), in turn, cephalosporin has a six-sided dihydrothiazine ring (B) and penicillin a five-sided thiazolidine ring (B). These basic structures that form the chemical nucleus for these antibiotics occur naturally in fungus. Moxalactam is not found in nature and is characterized by an oxygen substitution for the sulfur (S) atom in cephalosporin.

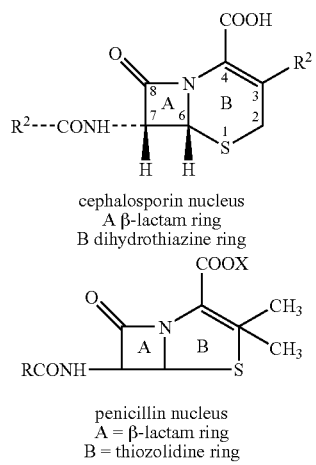

cephalosporin nucleus
A β-lactam ring
B dihydrothiazine ring penicillin nucleus
A = β-lactam ring
B = thiozolidine ring Cephalosporins and penicillin are bacteriocidal. Their antibacterial activity is due to an inhibition of peptidoglycan synthesis in the bacterial cell walls. Although the exact mechanism of action is not fully understood, these antibiotics bind to several proteolytic enzymes, e.g., carboxypeptidases and endopeptidases, that are involved in synthesizing the peptidoglycan latticework that strengthens the bacterial cell wall. The interaction between these antibiotics and the proteolytic enzymes is reversible. It is thought that these beta-lactam antibiotics act as substrate analogs for acyl-D-alanyl-D-alanine, the endogenous substrate for these enzymes. When these bacterial enzymes are bound up with antibiotic they cannot perform their function and the bacteria lyse as they replicate.

Similar carboxypeptidases and endopeptidases are associated with cell membranes of neurons and glia in the mammalian brain. One of their many functions is to rapidly degrade neuropeptides acting as neurotransmitters. Unlike the classical neurotransmitters, e.g. dopamine and serotonin, that rely on reuptake mechanisms to stop signal activation, neuropeptides are inactivated by their rapid degradation in the extracellular space. These beta-lactam related antibiotics are believed to have psychotropic activity by interfering with the metabolism (NAALADase activity) on the numerous neuropeptides altering the neuropeptide milieu of the brain.

Method

Figure 10A:
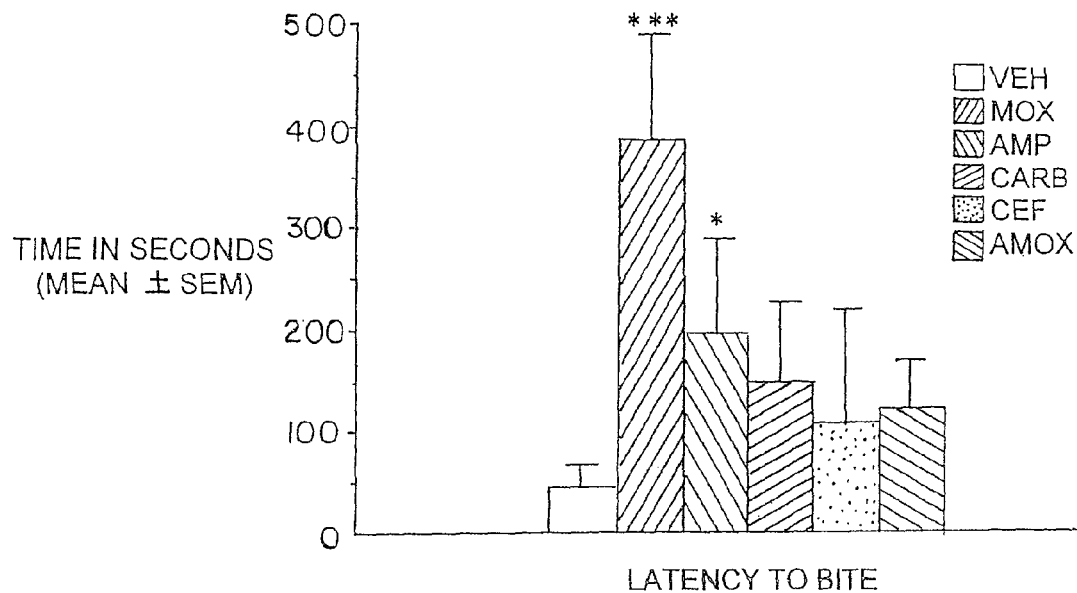
Figure 10B:
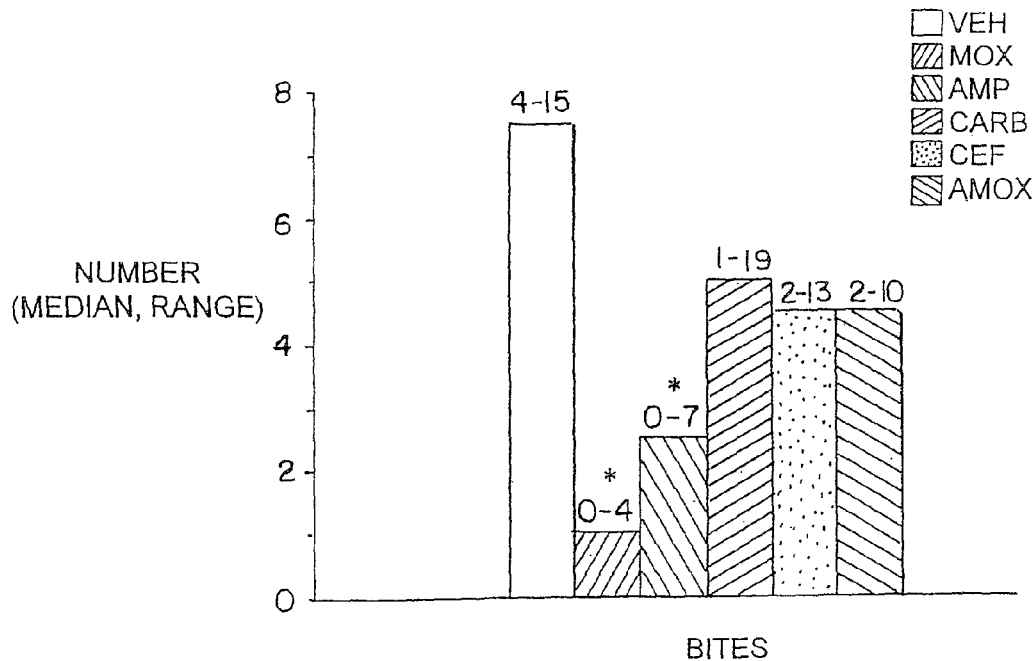
Figure 11A:
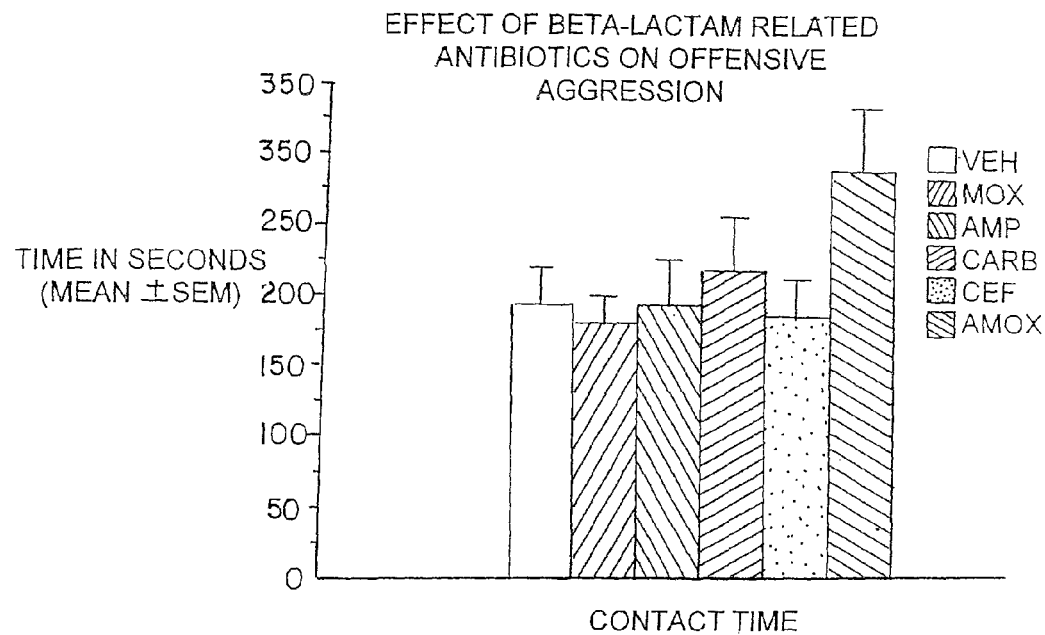
Figure 11B:
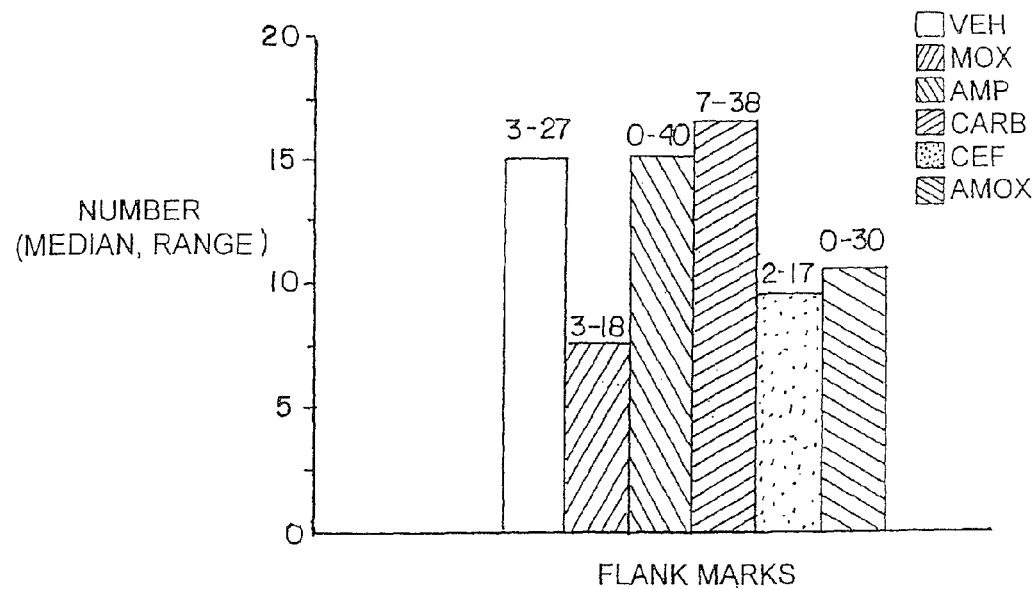

Six animals were tested with equimolar concentrations (90 µM) of Moxalactam (Mox), Ampicillin (Amp) Carbenicillin (Carb) Cefoxitin (Cef), Amoxicillin (Amox) or saline vehicle. The concentrations were adjusted to equal the 50 µg/kg dose used for MOX in previous studies. All solution were prepared in 0.9% NaCl and given IP. The order of injections was counter balanced. Animals were tested for offensive aggression 90 min after injection (FIG. 10). There was a significant difference between treatments on bite latency (F (5,30)=2.83; $p<0.05$). Both Mox and Amp significantly delayed the latency to bite ($p<0.001$ and $p<0.05$, respectively) as compared to vehicle control. There was also a significant difference between treatments on number of bites (H=10.6; $p<0.05$). Both Mox and Amp drugs significantly reduced the number of bites ($p<0.05$). There were no significant treatment effect on contact time or flank marking (FIG. 11).

Summary

These data indicate that the antiaggressive effect of the beta-lactam antibiotic Mox may be extended to include the beta-lactam ampicillin. Of all of the antibiotics tested, Mox has the greatest penetrability into the CNS. Patents given 2.0 g of Mox IV show cerebrospinal fluid levels of drug around 30 µg/ml. The ratio of CSF to serum levels of Mox is ca. 15-20%. It is estimated that the serum concentration of Mox in 140 g hamster given an IP injection of 14 µg of drug is 0.1 ng/ml. This would be reflected by a CSF concentration of 15 ng/ml or brain levels of Mox approximating 30 nM. These levels would certainly be in range to interact effectively with neuropeptide receptors most of which have binding affinities in the nanomolar range. Interaction with the classical neurotransmitters would be less likely because these receptors have Kd's in the micro and millimolar range.

Neonates with meningitis (conditions favoring CNS penetrability of beta-lactam antibiotics) show a ratio of CSF to serum level of Amp of ca. 10%. Cefoxitin, on the other hand has poor CNS penetrability even when the meninges are inflamed. Perhaps many of the beta-lactam antibiotics would be effective in suppressing aggressive behavior and they are simply limited by their pharmacokinetics and CNS penetrability. To test this notion it was necessary to repeat the beta-lactam antibiotic study using a higher dose of each drug.

X. High Dose Beta-Lactams

Figure 12A:
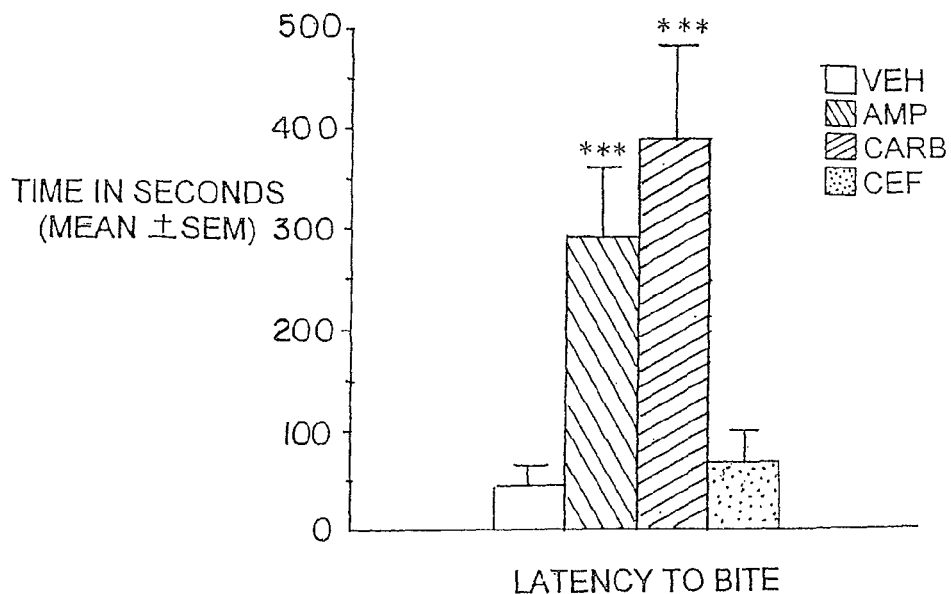
Figure 12B:
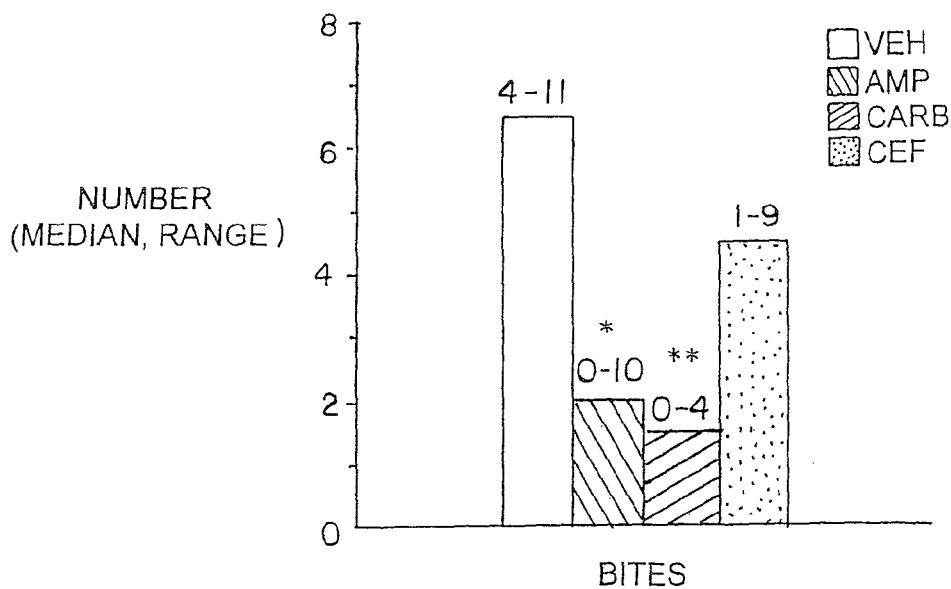
Figure 13A:
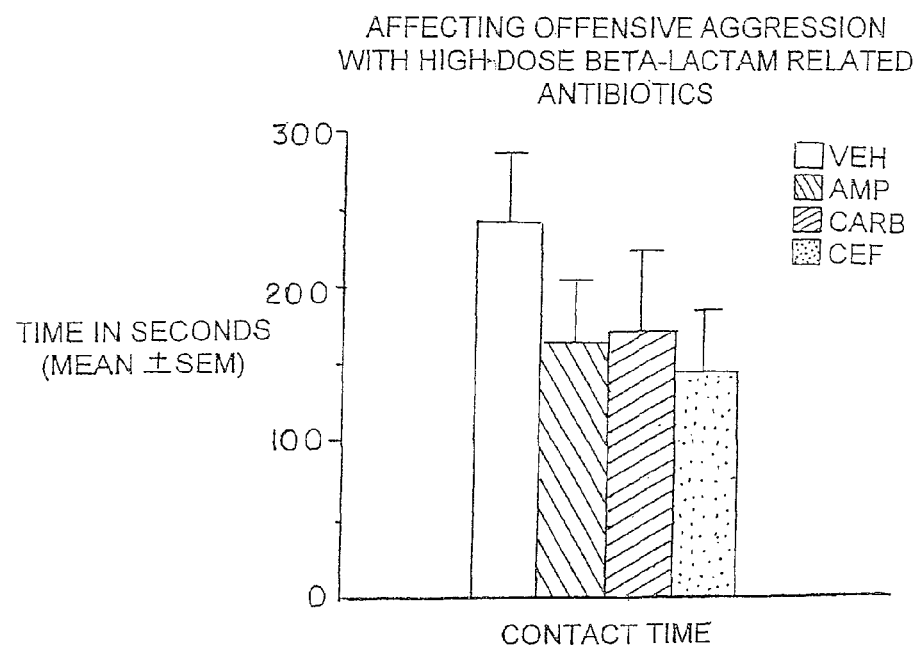
Figure 13B:
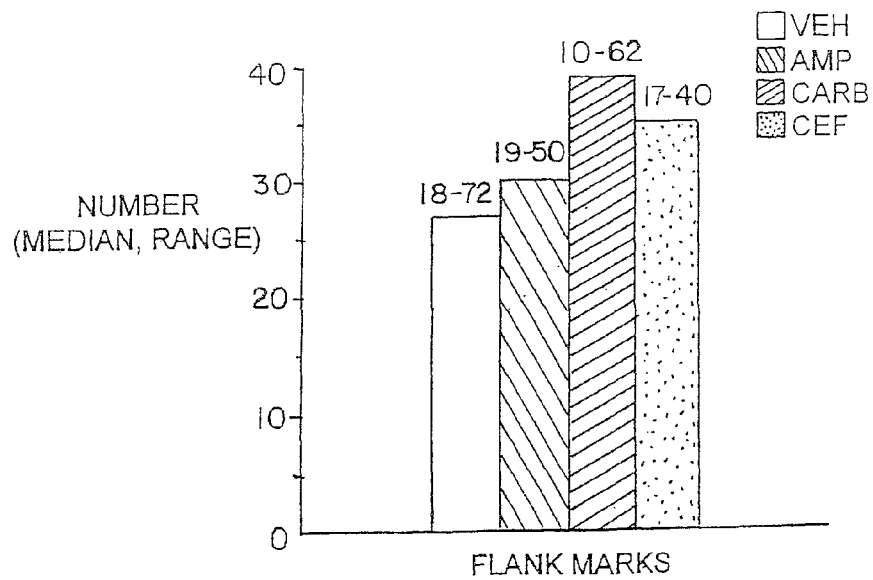

Six animals were tested with equimolar concentrations (ca. 5 mg/kg; 9 mM) of Ampicillin (Amp) Carbenicillin (Carb) and Cefoxitin (Cef) or saline vehicle. The concentrations were adjusted to equal the 5 mg/kg dose used in the dose response study for Mox. All solution were prepared in 0.9% NaCl and given IP. The order of injections was counter balanced. Animals were tested for offensive aggression 90 min after injection (FIG. 12). There was a significant difference between treatments on bite latency (F (4,25)=5.49; $p<0.01$). Both Amp and Carb significantly delayed the latency to bite ($p<0.001$) as compared to vehicle control. There was also a significant difference between treatments on number of bites (H=11.7; $p<0.05$). Both Amp and Carb significantly reduced the number of bites ($p<0.05$ and $p<0.01$, respectively). There were no significant treatment effect on contact time or flank marking (FIG. 13).

Figure 14A:
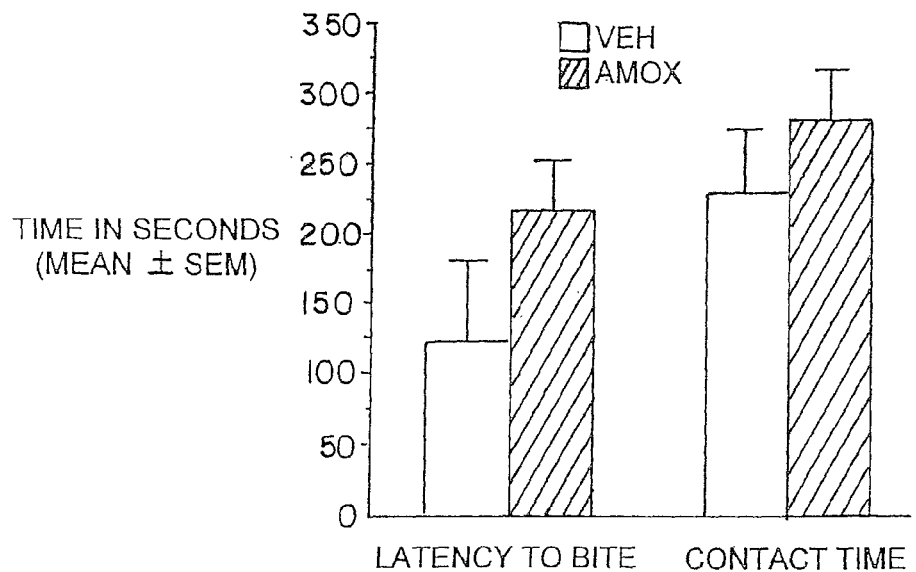
Figure 14B:
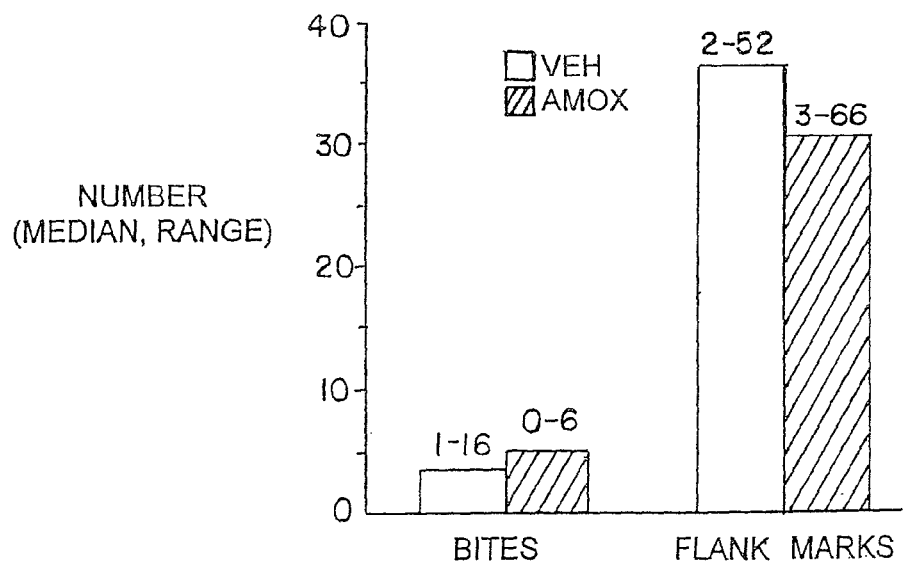

Amoxicillin was not included in this high dose beta-lactam antibiotic study; instead, it was run in a separate study using a dose of 1 mg/kg (ca. 2 mM). Eight animals were tested for offensive aggression 90 min after IP injection following treatment with Amox or saline vehicle (FIG. 14). Each animal was given each treatment with no less than 48 hrs between injections. The treatments were counterbalanced. Aggressive behavior was not significantly altered in animals treated with 1 mg/kg Amox.

Summary

These data indicate that ampicillin and carbenicillin given in high enough doses can suppress offensive aggression without altering contact time or flank marking. These data raise the possibility that the psychotropic effect of moxalactam is shared by other beta-lactams and that the biological mechanisms of action may be similar. Bioavailability and CNS penetrability, in part, may be the major component contributing to differences in biological efficacy. Indeed, more recent testing demonstrated that clavulanic acid, a β-lactam compound having no clinically significant antibiotic activity, but a clinically important β-lactamase inhibition activity, exhibits a wide variety of psychotropic effects, including antianxiety, antiaggression and cognition enhancement, at i.p. doses less than 1 µg/kg. Its high oral absorption and good blood brain barrier transport properties make it and related β-lactamase inhibitors preferred candidates for use in the methods and the pharmaceutical formulations in accordance with this invention.

The mechanism (s) of action for the psychotropic effects of these beta-lactams is now believed to be their interaction with neurogenic NAALADase. This is feasible since cephalosporins are reported to have bactericidal activity in concentrations as low as 10 nM. Note, the estimated concentration of Mox in the brain following the 50 µg/kg treatment is ca. 30 nM.

Another possible explanation for the psychotropic activity of beta-lactam antibiotics is the possible blockade of known neurotransmitter receptors or re-uptake proteins. To test this second possibility it was necessary to screen Mox for receptor interaction in a wide range of radio ligand binding assays.

XI. Screening Moxalactam in Receptor and Transport Binding Assays Testing Mox for Vasopressin $V_{1A}$ and Serotonin $5HT_{1A}$ Receptor Interaction Vasopressin and serotonin are both critical neurotransmitters in the control of offensive aggression in male hamsters (Ferris et al., 1998). These two neurotransmitters also are implicated in the control of human aggression (Coccaro et al., 1998). Vasopressin facilitates aggressive behavior while serotonin inhibits aggression, in part, by inhibiting the activity of the vasopressin system. Blockade of vasopressin $V_{1A}$ receptors and stimulation of serotonin $5HT_{1A}$ receptors in the anterior hypothalamus blocks offensive aggression (Ferris et al., 1999). Since Mox significantly suppresses offensive aggression it was hypothesized it did so by interacting with either one or both of these receptors. To test this notion Mox was tested in a membrane binding assay for competition for the $V_{1A}$ receptor (Ferris et al., 1994) and in a receptor autoradiography assay for competition for the $5HT_{1A}$ receptors (Ferris et al., 1999). Moxalactam in a concentration of 1 µM did not significantly displace $I^{125}$ HO-LVA (vasopressin ligand) binding in a hamster liver membrane preparation. Similarly, Mox was ineffective in reducing specific binding of $I^{125}$ DPAT (serotonin ligand) to tissue sections of the hamster brain.

Summary

These data show that moxalactam has no direct interaction with vasopressin $V_{1A}$ and serotonin $5HT_{1A}$ receptors in the hamster. This would suggest that moxalactam is affecting behavior by altering the activity of other neurochemical pathways.

Testing for Amino Acid, Adrenergic, Serotonergic, and Dopaminergic Receptors and Their Transporters Moxalactam was screened in thirty-six different binding assays by NOVASCREEN, a contract research organization based in Hanover, Md. Moxalactam was tested at 100 nM and run in duplicate samples for each of the assays listed on the following page. These assays were chosen because their respective receptor or transporter may play a role in the pathophysiology of mental illness. Moxalactam had no significant effect in any of these binding assays.

| Amino Acid Targets |
| --- |
| Benzodiazepine, peripheral |
| GABA |
|     Agonist Site |
|     Benzodiazepine, central |
| GABA |
| Glutamate |
|     AMPA Site |
|     Kainate Site |
|     NMDA, Agonist Site |
|     NMDA, Glycine [strychnine-insensitive] site |
| Glycine [strychnine-sensitive] site |

| Biogenic Amine-Adrenergic Targets |
| --- |
| Adrenergic |
|     $\alpha_{1A}$ |
|     $\alpha_{1B}$ |
|     $\alpha_{2A}$ (human HT-29 cells) |
|     $\alpha_{2B}$ |
|     $\alpha_{2C}$ (human recombinant) |
|     $\beta_1$ |
|     $\beta_2$ |

| Biogenic Amine-Serotonergic Targets |
| --- |
| Serotonin |
|     $5HT_{1A}$ (human recombinant) |
|     $5HT_{1B}$ |
|     $5HT_{1D}$ |
|     $5HT_{2A}$ (formerly $5HT_2$) |
|     $5HT_{2C}$ |
|     $5HT_3$ |
|     $5HT_4$ |
|     $5HT_6$ (rat recombinant) |
|     $5HT_7$ (rat recombinant) |

| Biogenic Amine-Dopaminergic Targets |
| --- |
| Dopamine |
|     $D_1$ |
|     $D_2$ (human recombinant) |
|     $D_3$ (rat recombinant) |
|     Clozapine |

| Uptake/Transporter Targets |
| --- |
| Adrenosine |
| Adrenergic, Norepinephrine |
| Dopamine |
| GABA |
| Glutamate |
| Muscarinic, Choline |
| Serotonin |

| Hormone Targets |
| --- |
| Corticotropin Releasing Factor |

Testing for Corticotropin Releasing Hormone Receptor

Corticotropin releasing hormone (CRH or CRF as shown on the following page) is a critical neurohormone in the regulation of stress. Since Mox suppresses impulsivity, aggression, and anxiety while enhancing learning and memory it may be acting to reduce stress. For this reason, Mox was tested by NOVASCREEN in a CRF binding assay. Moxalactam at a concentration of 100 nM had no effect in this assay.

Summary

These data show that moxalactam does not interact directly with many of the receptors and transporters implicated in the pathophysiology of aggression and mental illness. This leaves three possible mechanisms of action: 1) interaction with known receptors that were not screened, e.g., histamine, acetylcholine, and other neuropeptides, 2) interaction with unknown or "orphan receptor," or 3) interaction with peptidolytic enzymes (e.g., NAALADase) in the CNS that alter the chemical milieu of the brain.

XII. Examining Mechanism of Action

Testing Peptidoglycan-Precursor Peptide for Effects on Offensive Aggression Rationale The beta-lactam antibiotics have a stereochemistry that resembles acyl-D-alanyl-D-alanine, the natural substrate for the bacterial proteolytic enzymes. Presumably, this structural characteristics enables beta-lactam antibiotics to behave as competitive substrate blocking enzyme activity. To test this hypothesis an analog of acyl-D-alanyl-D-alanine, peptidoglycan-precursor peptide (Nieto and Perkins 1971; Zeiger and Maurer, 1973) was tested for antiaggressive effects in the hamster resident/intruder paradigm.

Method

Peptidoglycan-precursor peptide, Ala-D-γ-Glu-Lys-D-Ala-D-Ala, (PPP) was obtained from Sigma Chemical and reconstituted in DMSO and diluted in 0.9% NaCl to a final concentration of ca. 2 mM. Animals were anesthetized with sodium pentobarbital (50 mg/kg), implanted with microinjection guide cannulae aimed at the lateral ventricle and allowed to recover for two days before testing. On the day of testing, animals (n=6) were injected with vehicle (2% DMSO in 0.9% NaCl) or PPP in a dose of ca. 1 mg/kg in a volume of 1 µl. Sixty minutes after injection, animals were retested for offensive aggression toward a smaller intruder placed into their home cage. Two days later animals were tested again and the order of treatments reversed.

Results

Figure 15A:
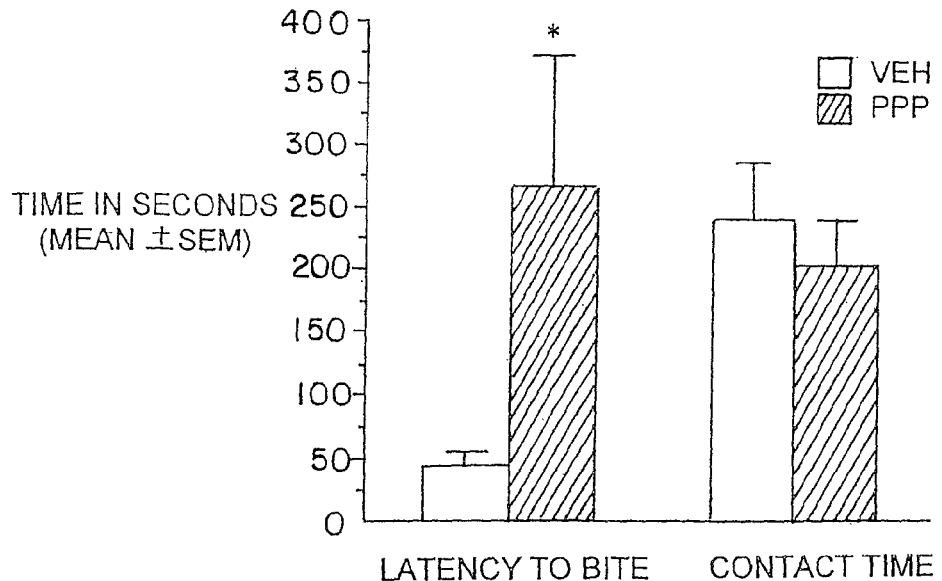
Figure 15B:
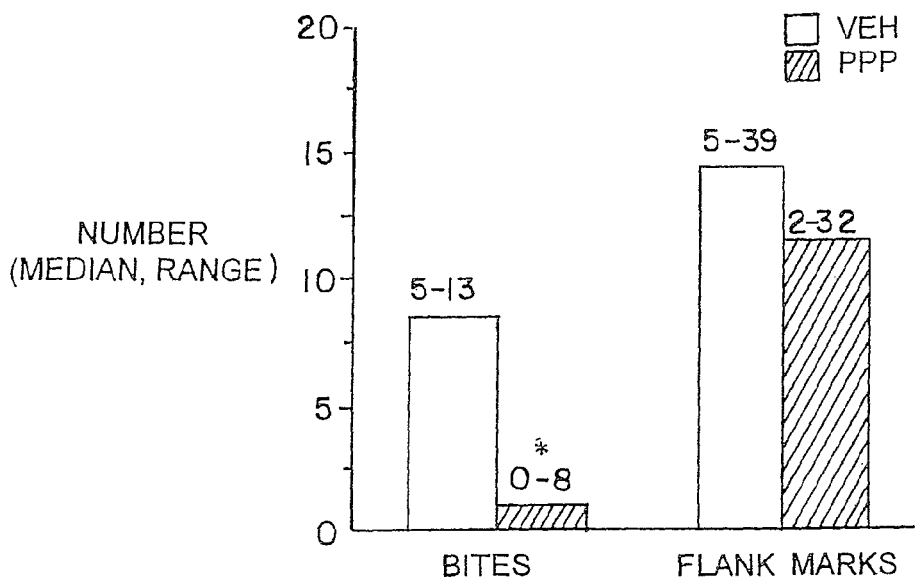

Peptidoglycan-precursor peptide significantly increased the latency to bite (p<0.05) and reduced the number of bits (p<0.05) during a 10 min. Observation period (FIG. 15). There was no significant difference in contact time or flank marking between treatments (FIG. 15).

Testing Peptidoglycan-Precursor peptide for Effects of Olfactory Discrimination

Figure 16:
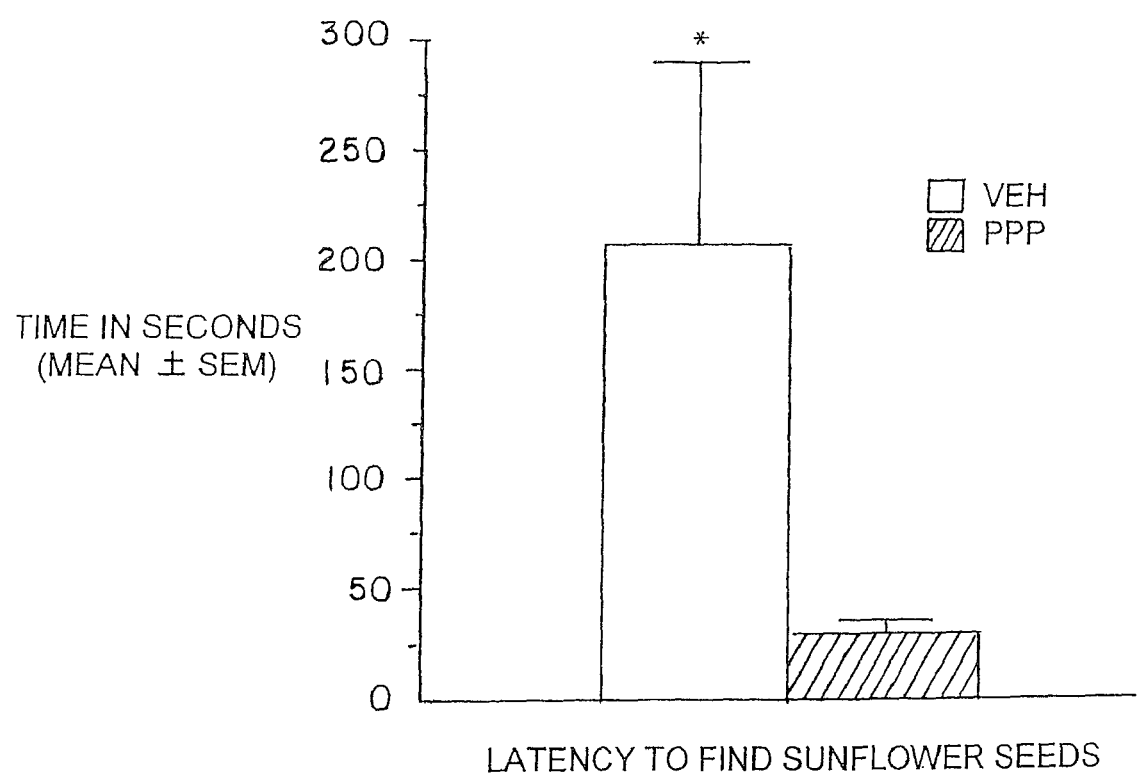

Six animals received an intracerebroventricular injection of vehicle or 1 mg/kg PPP and tested for olfactory discrimination by measuring their latency to find hidden sunflower seeds (FIG. 16). The injections were counterbalanced with each animal receiving each treatment. Prior to testing animals were fasted for 24 hrs. Sixty min. After injection animals were briefly taken from their home cage while six sunflower seeds were buried under the bedding in one corner. Animals were placed back into their home cage and scored for the latency to find the seeds in a five min. Observation period. The latency to find the seed was significantly (p<0.05) reduced in animals treated with PPP as compared to vehicle.

Summary

The direct injection of peptidoglycan-precursor peptide into the brain of hamsters has the same behavioral results as the peripheral injection of Mox. Both drugs and both routes of administration significantly reduce aggressive behavior without altering social interest of motor activity, i.e., contact time and flank marking. In addition, the enhancement of olfactory discrimination that appears to be the simplest and most robust behavioral assay for screening beta-lactam antibiotics is similarly affected by the precursor peptide. These findings are evidence that beta-lactam antibiotics affect behavior by: 1) acting directly on the brain, and 2) resembling the acyl-D-alanyl-D-alanine peptide moiety.

While clavulanic acid contains a beta-lactam ring and is structurally similar to penicillins and cephalosporins, it has weak antibacterial activity with no therapeutic value as an antibiotic. However, when given in combination with some beta-lactam antibiotics like ticarcillin (TIMENTIN) clavulanic acid can extend the spectrum and enhance the activity of the antibiotic (AHFS, 1991). This synergistic activity is possible because clavulanic acid acts as an irreversible competitive inhibitor of bacterial beta-lactamases that naturally degrade and inactive beta-lactam antibiotics (Brown et al., 1976; Reading and Cole 1977).

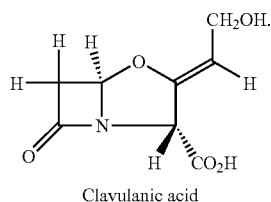

Clavulanic acid

Clavulanic acid is commercially available in the United States but only in fixed combination with other drugs. Commonly prescribed TIMETIN is normally given intravenously in doses ranging from 200-300 mg/kg/day (based on ticarcillin content) which corresponds to a dose of clavulanic acid of approximately 7-10 mg/kg/day (AHFS, 1991). There are no reported adverse reactions or contraindications for clavulanic acid given in this dose range (Koyu et al., 1986; Yamabe et al., 1987). The data presented below report clavulanic acid can alter CNS activity and behavior at doses ranging from 10 ng to 10 μg/kg, or 1000 to 1,00,000 times less than used in antibacterial indications.

Clavulanic acid by itself is orally active and stable. The bioavailability is approximately 64 to 75% (Davies et al., 1985; Bolton et al., 1986) with an elimination half-life of just under two hours. Peak plasma concentrations occur between 45 min to three hours after ingestion (Bolton et al., 1986) with a plasma half-life of over 2 hrs (Nakagawa et al., 1994). The volume of distribution is around 15 liters suggesting clavulanic acid is primarily confined to extracellular fluid (Davies et al., 1985). The CSF/plasma ratio is around 0.25, evidence that clavulanic acid readily passes the blood-brain barrier (Nakagawa et al., 1994).

Behavioral Studies with Clavulanic Acid

I. Clavulanic Acid Dose-Response in the Seed Finding Model of Anxiety

Rationale

Figure 37:
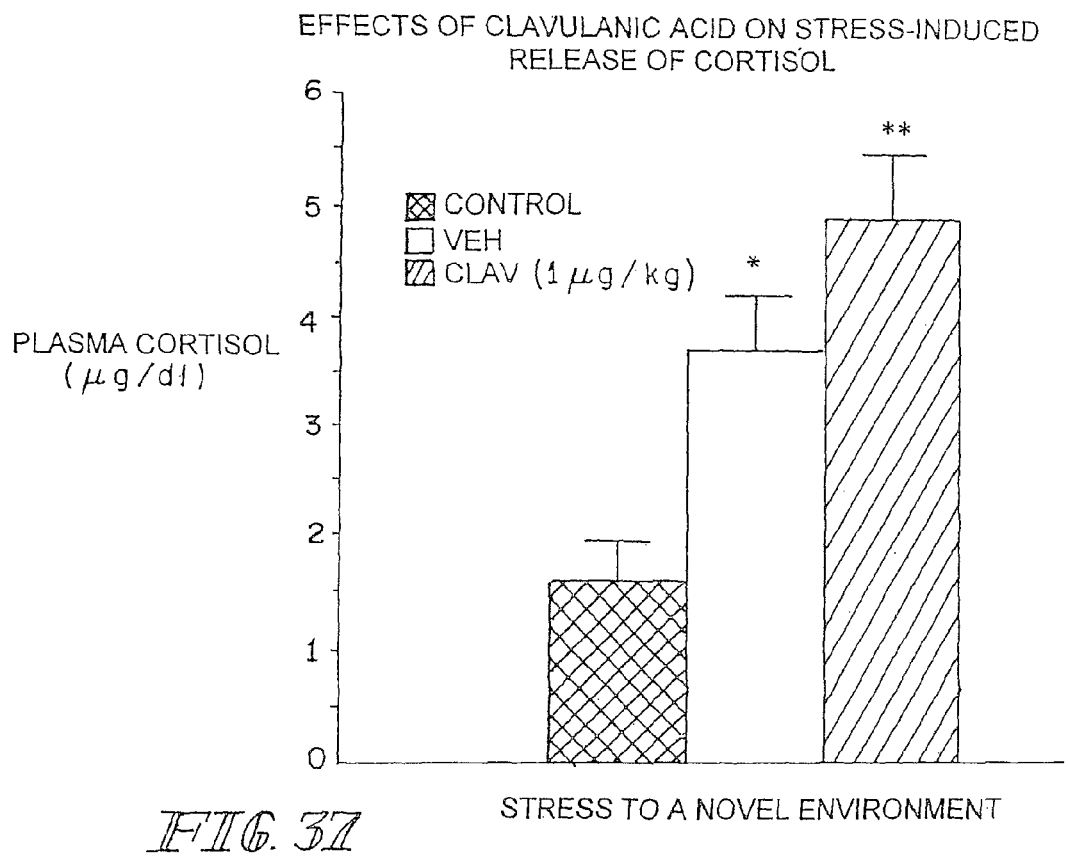

Clavulanic acid (CLAV) is structurally similar to the beta-lactam antibiotics. A most robust and simple bioassay for screening beta-lactams for CNS activity is the golden hamster seed finding model of anxiety. Briefly, hamsters are deprived of food overnight. The following day they are exposed to the additional stress of being taken from their home cage and placed in a novel environment for a few minutes. This manipulation stimulates the release of the stress hormone cortisol (FIG. 37). During their absence from the home cage, sunflower seeds are hidden under the bedding in one of the corners. When returned to the home cage, hamsters routinely scramble along the walls for 1-2 min before settling down, locating and eating the seeds. However, animals treated with the benzodiazepine anxiolytic chlordiazepoxide find seeds in less than 10 sec. This reduction in seed finding time from minutes to seconds also occurs following treatment with moxalactam and other beta-lactam antibiotics.

Experimental Protocol

Figure 25:
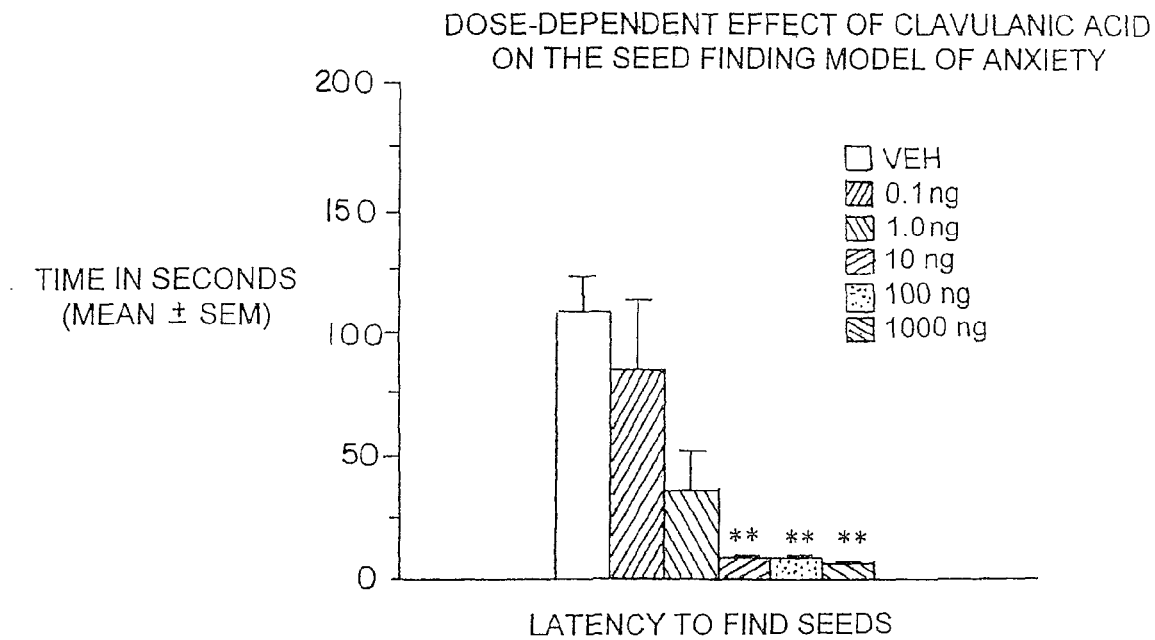

Male, Syrian golden hamsters (*Mesocricetus auratus*) (120-130 g) obtained from Harlan Sprague-Dawley Laboratories (Indianapolis, Ind.) were housed individually in Plexiglas cages (24 cm×24 cm×20 cm), maintained on a reverse light:dark cycle (14L:10D; lights on at 19:00 hr) and provided food and water ad libitum. A range of concentrations of CLAV (saline vehicle, 0.1, 1.0, 10, 100 1,000 ng/kg) were tested in six groups of hamsters (4-8/group)(FIG. 25). All tests were conducted during the dark phase of the circadian cycle under dim red illumination. Prior to testing all animals were fasted for 20-24 hrs. Ninety min after intraperitoneal (IP) injection of drug, animals were taken from their home cage and placed into a holding cage for 2 min. During their absence, six sunflower seeds were buried under the bedding in one corner of their home cage. Animals were placed back into their home cage randomly facing any one of the empty corners and timed for their latency to find the seeds in a five min observation period. Latency times were analyzed with a one-way ANOVA followed by Scheffe's post hoc tests. Assumption of equal variances was tested (Hartley's F-max=2.1 p>0.05)

Results

The latency to find the sunflower seeds was significantly different between doses ($F_{(5,30)}$=10.0; p<0.0001). CLAV in doses of 10 ng and above significantly (p<0.01) reduced latency times to less than 8.0 sec as compared to saline vehicle with a mean latency of 104 sec. The dose of 1 ng/kg was not significantly different from vehicle control.

Summary

The data show CLAV given in a dose of 10 ng/kg body weight has maximal efficacy the seed finding test. The adult male hamsters used in these studies weighed around 125 g. Hence, these animals were given about 1.25 ng of CLAV. CLAV has a volume of distribution approximating the extracellular fluid volume. The extracellular water content of lean body mass is approximately 22%. The concentration of 1.25 ng of CLAV in 27.5 ml of water is 0.045 ng/ml or about 200 µM (formula weight of the potassium salt of CLAV is ca. 240). Since the CSF/plasma ratio is 0.25 the estimated concentration in the brain would be around 50 µM.

The seed finding model of anxiety appears to have empirical validity (McKinney 1989) i.e., drugs like benzodiazepines that are used to treat clinical anxiety are effective in the animal model. However, a wider spectrum of anxiolytics and non-effective drugs must be screened to assess the incidence of false negatives and false positive before adopting seed finding as a model of anxiety. Hence, it was necessary to validate the potential anxiolytic activity of CLAV in the traditional elevated plus-maze.

II. Testing Clavulanic Acid in the Elevated Plus-Maze

The elevated plus-maze was developed for screening anxiolytic and anxiogenic drug effects in the rat (Pellow et al., 1985). The method has been validated behaviorally, physiologically, and pharmacologically. The plus-maze consists of two open arms and two enclosed arms. Rats will naturally make fewer entries into the open arms than into the closed arms and will spend significantly less time in open arms. Confinement to the open arms is associated with significantly more anxiety-related behavior and higher stress hormone levels than confinement to the closed arms. Clinically effective anxiolytics, e.g., chlordiazepoxide or diazepam, significantly increase the percentage of time spent in the open arms and the number of entries into the open arms. Conversely, anxiogenic compounds like yohimbin or amphetamines reduce open arm entries and time spent in the open arms.

Experimental Protocol

Male Wistar rats weighing 250-300 g were group housed in a normal 12:12 light-dark cycle with light on at 0800 hr and provided food and water ad libitum. The plus-maze consisted of two open arms, 50 cm long, 10 cm wide, with walls 40 cm high made of clear Plexiglas. The two closed arms had the same dimensions but included a roof. The Plexiglas for the closed arms was painted black. Each pair of arms was arranged opposite to each other to form the plus-maze. The maze was elevated to a height of 50 cm. Eighteen animals were tested in the plus-maze 90 min following the IP injection of 1.0 µg/kg CLAV, 50 or vehicle control in a volume of ca. 0.3 ml. The order of treatments was counter balanced with at least 48 hrs between injections. At the start of the experiment, the animal was placed at the end of one of the open arms. Over a five min observation period, animals were scored for the latency to enter the closed arm, time spent in the closed arm and the number of open arm entries following the first occupation of the closed arm. The study produced tables of repeated measures. The data between treatments were compared with a two-way, repeated measures ANOVA followed by Bonferroni post hoc tests.

Results

Figure 26A:
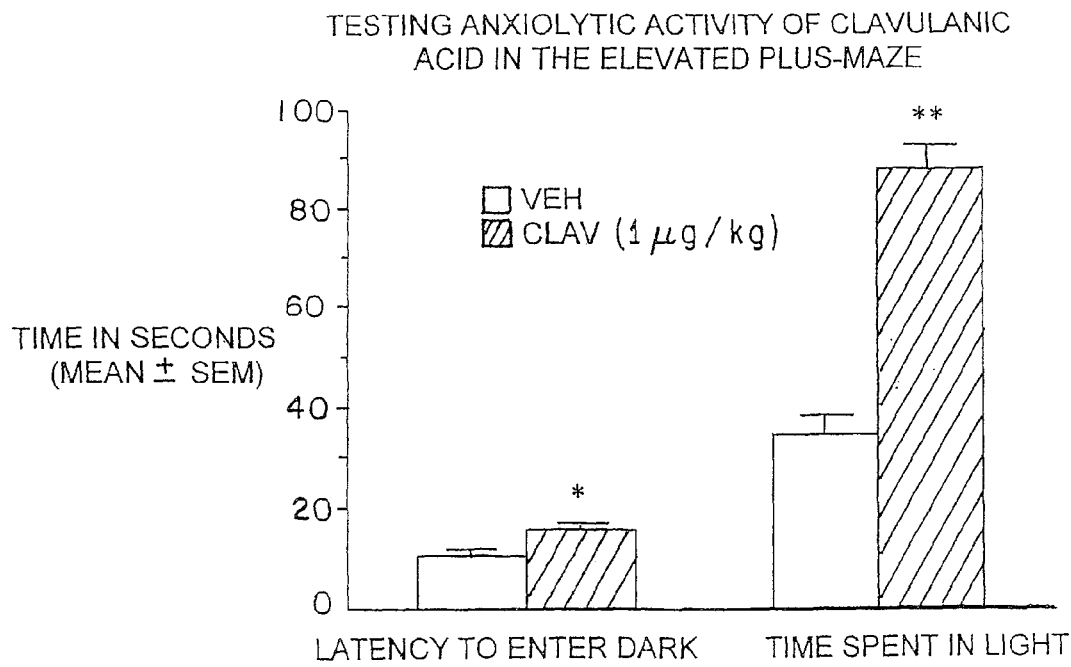
Figure 26B:
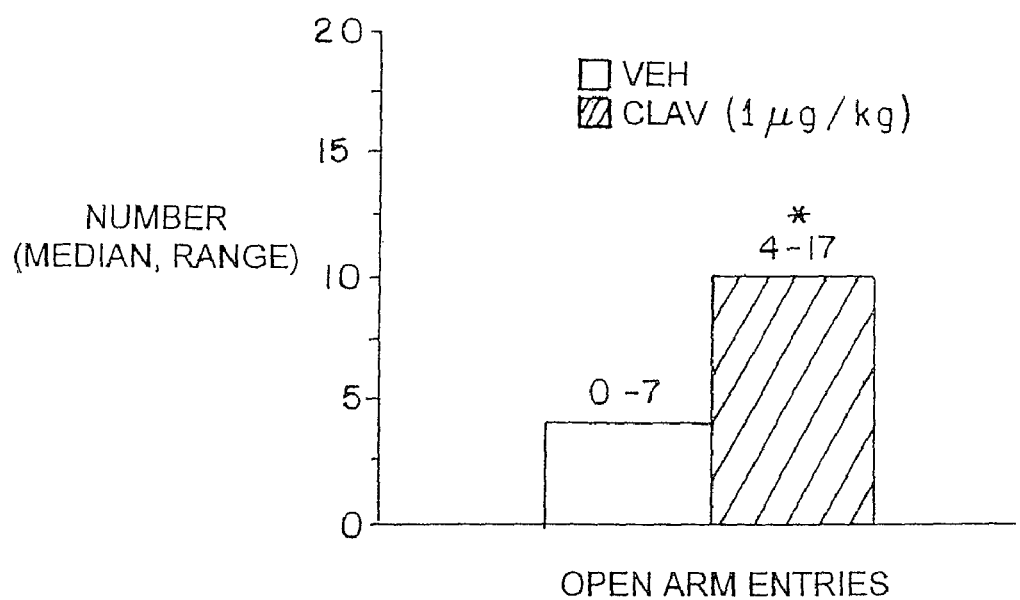

There was a significant difference between treatments for latency to enter the dark ($F_{(1,18)}=8.53$; $p<0.01$). When treated with CLAV ($p<0.05$) animals stayed in the starting open light position longer than when treated with vehicle (FIG. 26). The time spent in the open arm was highly significant between treatments ($F_{(1,18)}=144$; $p<0.0001$) (FIG. 26). The time spent in the open arm was significantly increased for CLAV ($p<0.01$) as compared to vehicle. Finally, the open arm entries were significantly different between treatments ($F(1,18)=44.0$ $p<0.0001$) with CLAV ($p<0.01$) treatment showing increased movement into the lighted open arms as compared to vehicle (FIG. 26).

Summary

These data show CLAV given at a dose of 1 µg/kg has anxiolytic activity in the plus-maze. These data are encouraging; however, many anxiolytics such as the benzodiazepines depress motor activity. Since animals treated with CLAV took a longer time to move from the lighted open arm to the dark, protected, closed arm it could be argued that this beta-lactam did not reduce anxiety, instead it sedated the animal and retarded movement. To control for this possibility it was necessary to screen CLAV for general motor activity in an open field paradigm.

III. Motor Activity in an Open Field

Experimental Protocol

Figure 27:
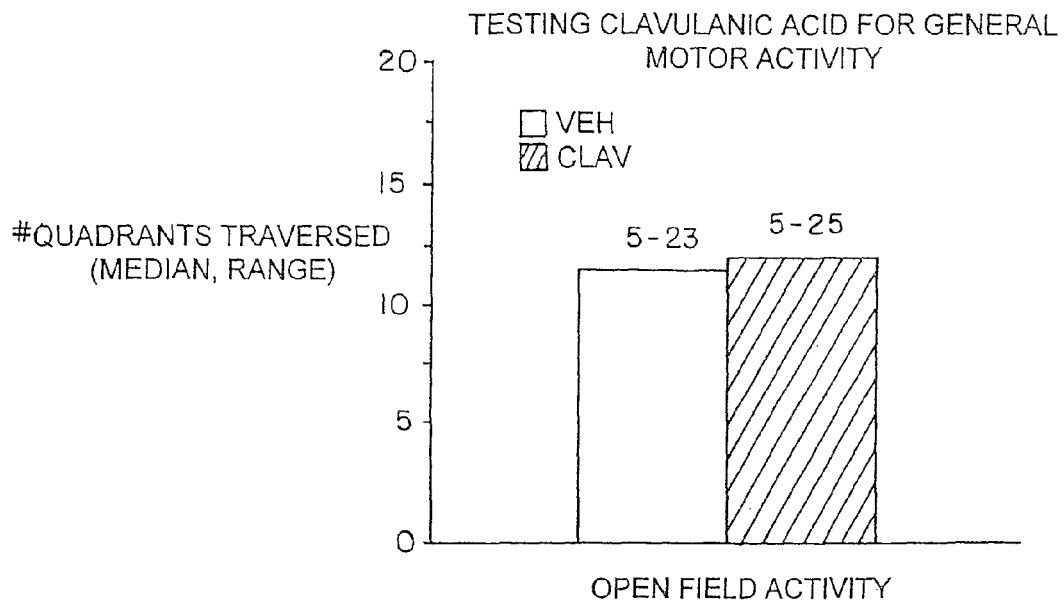

Immediately after each of the plus-maze tests reported above in Section II, animals were tested for general motor activity in an "open field." Animals were placed into a large clean Plexiglas cage (48×32×40 cm) devoid of bedding. This open field was delineated into equal quadrants by tape on the underside of the cage. Animals were scored for motor activity by counting the number of quadrants traversed in 1 min. There were no significant differences between CLAV and vehicle treatment on open field activity (FIG. 27).

Summary

Figure 39:
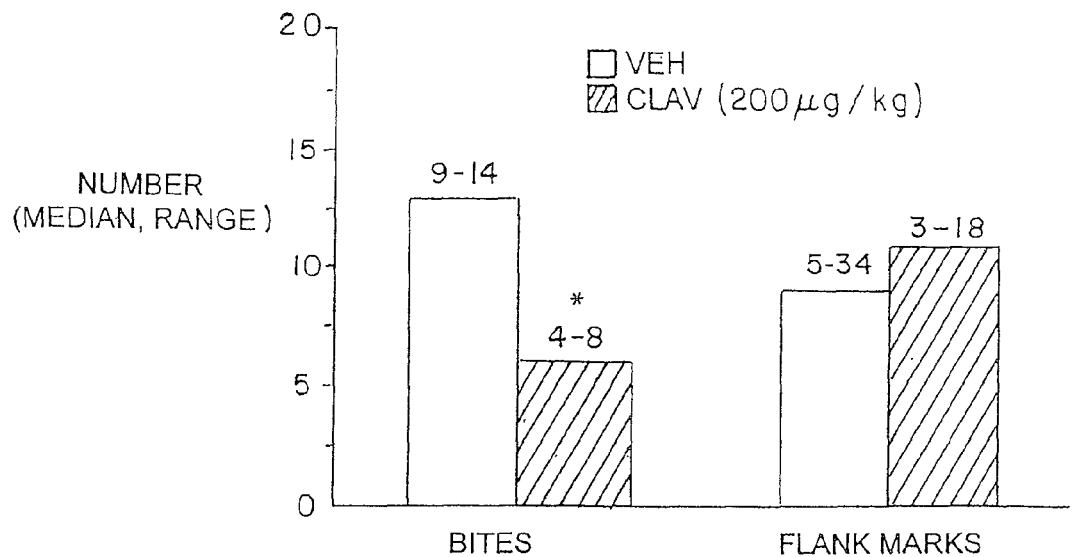

There is no evidence in the open field test that CLAV depress motor activity. This finding is corroborated in another behavioral study, flank marking reported in Section VII. Flank marking is a complex stereotyped motor behavior used by hamsters to disseminate pheromones for olfactory communication (FIG. 39). Flank marking is unaffected by treatments with CLAV. It would appear that this beta-lactam has an advantage over the more conventional benzodiazepine anxiolytics since it does not depress motor activity. However, is the anxiolytic activity of CLAV comparable to the clinically prescribed benzodiazepines?

IV. Clavulanic Acid vs Chlordiazepoxide in the Plus-Maze

Experimental Protocol

Chlordiazepoxide (LIBRIUM) is a commonly prescribed anxiolytic that has been thoroughly characterized in preclinical studies. The effective anxiolytic dose in the plus-maze is 10-25 mg/kg (Lister 1987; File and Aranko 1988; Shumsky and Lucki 1994). In this range of doses, chlordiazepoxide (CDP) is a sedative and depresses motor activity complicating the interpretation of any behavioral assay that requires locomotion (McElroy et al., 1985). However, it was discovered animals develop a tolerance to the motor depression with repeated daily administration of CDP for several days (Shumsky and Lucki 1994). Hence in these studies, rats (n=6) were given a single IP injection of CDP (10 mg/kg) each day for seven days prior to the start of the experiment. While CLAV has no effect on motor activity it was necessary to treat an equal number of rats with daily injections of CLAV (100 ng/kg) to insure a balanced experimental design. In addition there was a third group of rats (n=6) receiving daily injections of saline vehicle. The study reported in Section II tested CLAV at 1 µg/kg in the plus-maze. The data from the seed finding assay of anxiety shown in Section I suggests CLAV should be effective between doses of 10 ng to 1 µg/kg. For this reason CLAV was tested at 100 ng/kg in these studies.

Results

Figure 28A:
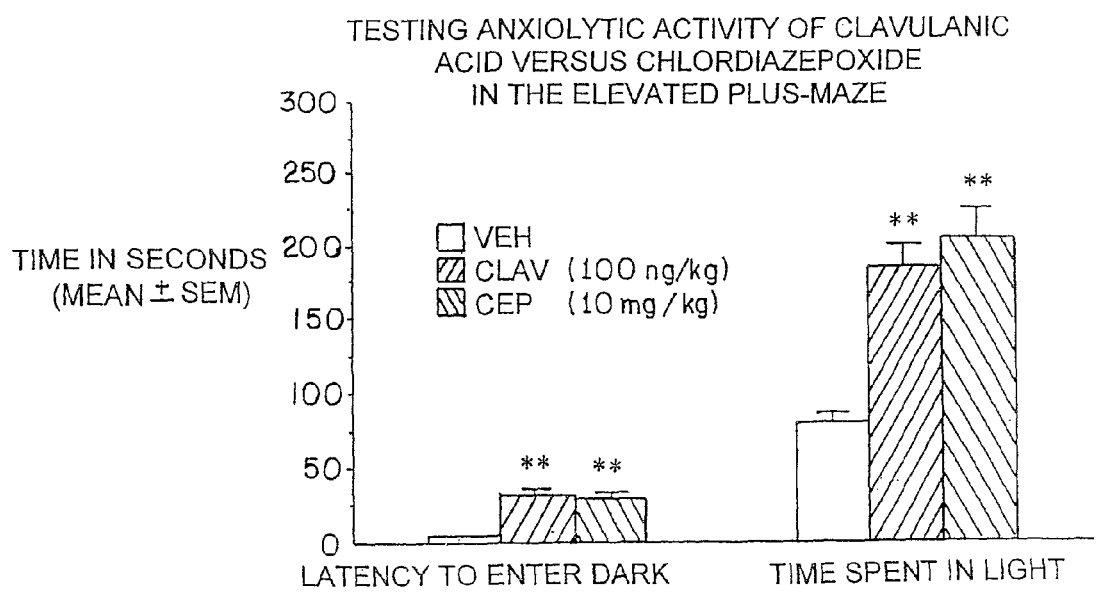
Figure 28B:
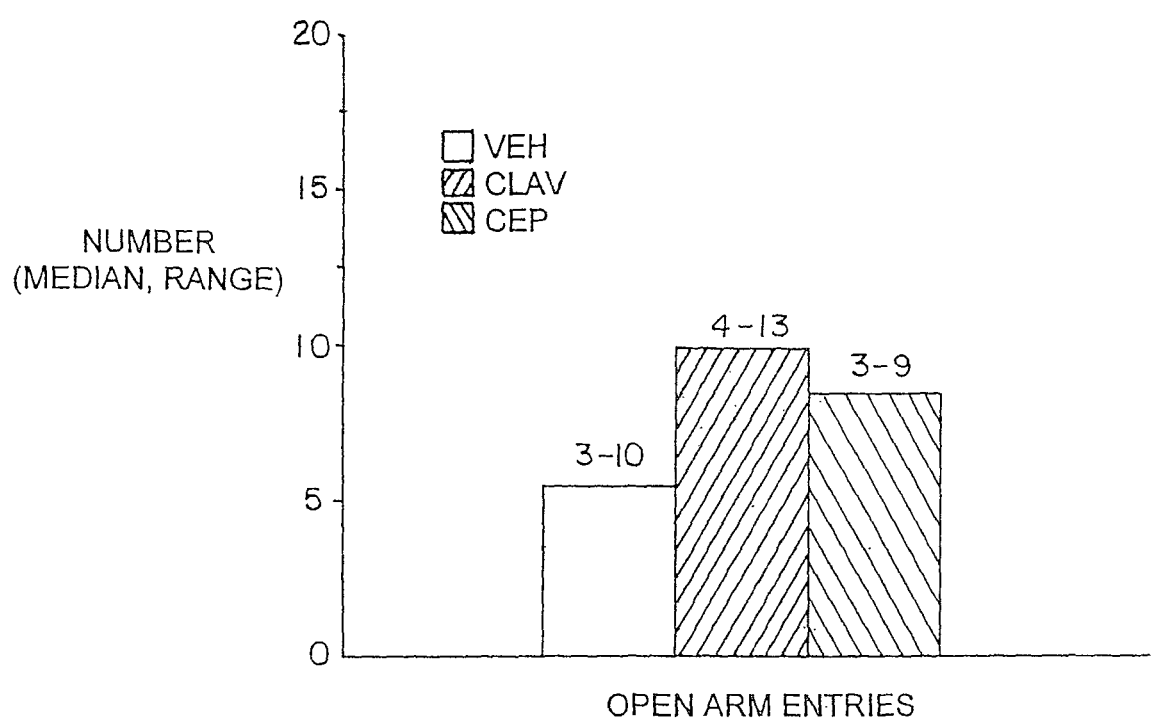

There was a significant difference between treatments ($F_{(2,15)}$=21.45, p<0.001) for the latency to enter the dark. The latency to enter the dark closed arms was significantly greater for animals treated with CLAV and CDP (p<0.01) as compared to vehicle control (FIG. 28A). There was also a significant difference between treatments ($F_{(2,15)}$=17.14, p<0.001) for the time spent in the light. The time spent exposed to light in the open arms was also significantly greater for the CLAV and CDP (p<0.01) treated animals as compared to vehicle (FIG. 28A). There was no significant difference between treatments for open arm entries (FIG. 28B).

Summary

These data show that CLAV and CDP have similar anxiolytic activity in the elevated plus-maze. Yet, CLAV has greater potency being effective at a dose 100,000 times less than CDP. Furthermore, CLAV does not have the sedative, motor depressant activity of the conventional benzodiazepine anxiolytics. The anxiolytic effects of CLAV are immediate and do not require the development of tolerance to realize behavioral efficacy. However, a point of caution, benzodiazepines have another undesirable side effect for which there is no development of tolerance—amnesia (Shumsky and Lucki 1994). For example, diazepam (VALIUM) selectively impairs short-term memory and attention while sparing long-term memory (Liebowitz et al., 1987; Kumar et al., 1987). Hence, it was necessary to test CLAV for any untoward effects on learning and memory.

V. Clavulanic Acid and Spatial Memory in the Water Maze

The Morris water maze was developed to test spatial memory (Morris, 1984). The pool is divided into quadrants usually designated North, South, East and West. The water in the pool is made opaque with milk powder. Hidden just beneath the surface in one of the quadrants is a platform that serves as a escape route for rodents placed into the pool. An animal is placed some where in the pool from a variety of different start points and is timed for latency to find the platform, percent time spent in each quadrant, distance traveled and swimming speed. The animals have no visual or spatial cues in the pool and must rely on extra-maze cues, i.e., objects set up outside the pool that can be seen by the swimming animal. Through a series of trials a rat develops "place learning" or knowledge about the position of the platform based upon the extra-maze cues. The platform can be moved to a different quadrant each day combining spatial memory with working memory. This paradigm involves extinction of the prior memory and resolution of a new spatial problem.

1. Spatial Navigation

Methods

The water maze consisted of a black plastic circular pool ca. 150 cm in diameter and 54 cm in height filled to a level of 35 cm with water made opaque with powdered milk. The pool was divided into four quadrants with a platform 10 cm in diameter submerged 2 cm below the surface in the northwest quadrant. The water was maintained at a temperature of 25° C. Around the pool were several visual cues. Above the pool was a video camera for tracking the movement of the experimental animal. The data collection was completely automated using the software developed by HVS Image (Hampton, UK). Before testing, rats were familiarized with the pool and platform placed in the northwest quadrant. Each day for 4 consecutive days, animals were placed into pool at random sites and given two min to find the platform. Animals were treated one hr before testing with 1.0 µg/kg CLAV (n=9) or vehicle (n=9). Following these familiarization trials, animals were tested for spatial navigation. The first day of testing began with the platform in the expected northwest quadrant. All behavior was videotaped for a two min observation period. After testing the animal were dried off and placed back into their home cage. On each subsequent day the platform was moved to a new quadrant and the rat started at different positions. The rat was always placed into the pool facing the sidewall. The start positions relative to the platform were different for each of the four trials; however, the platform was always in the same relative position in each quadrant. It was positioned 20 cm in from the side of the pool and in the left corner from the center facing out. The latency to find the hidden platform, path length, swim rate, and quadrant times between CLAV and vehicle treated animals were compared with a two-way, repeated measures ANOVA followed by Bonferroni post hoc tests.

Results

Figure 29:
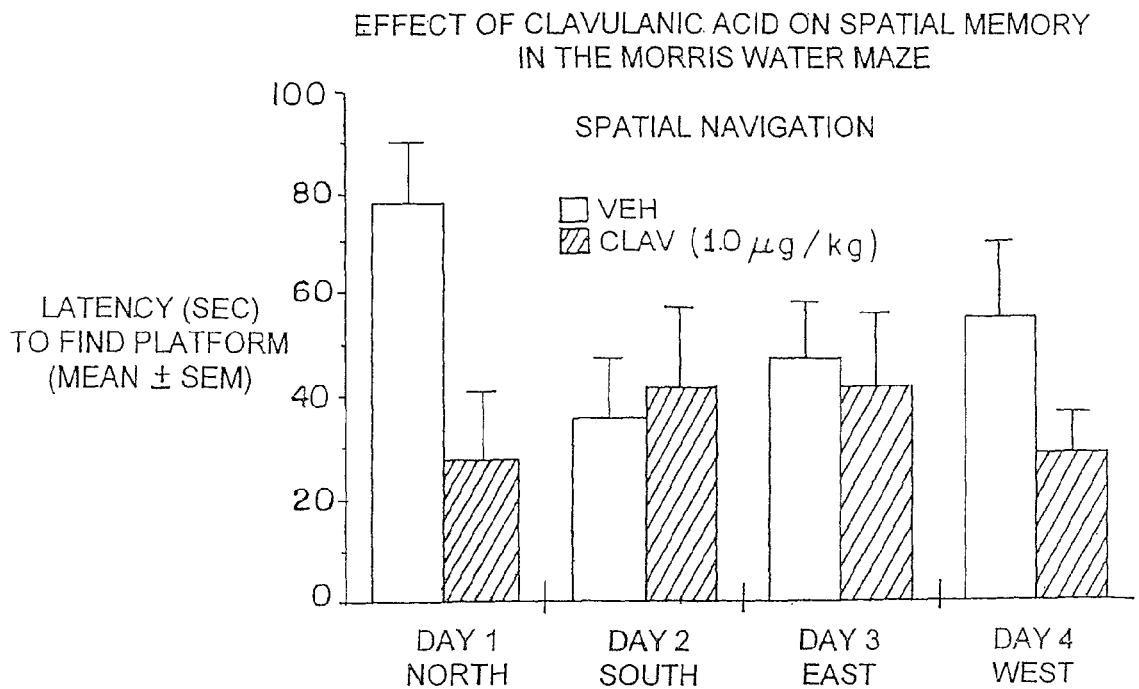

There was no main effect for drug treatment ($F_{(1,16)}$=4.17, p<0.057), days of testing ($F_{(3,48)}$=0.51, p>0.5) or interaction between factors ($F_{(3,48)}$=1.92 p>0.1) (FIG. 29) for latency to find the platform. However, animals treated with CLAV showed shorter latencies to find the platform on Days 1 and 4 with a trend towards significance.

Figure 30A:
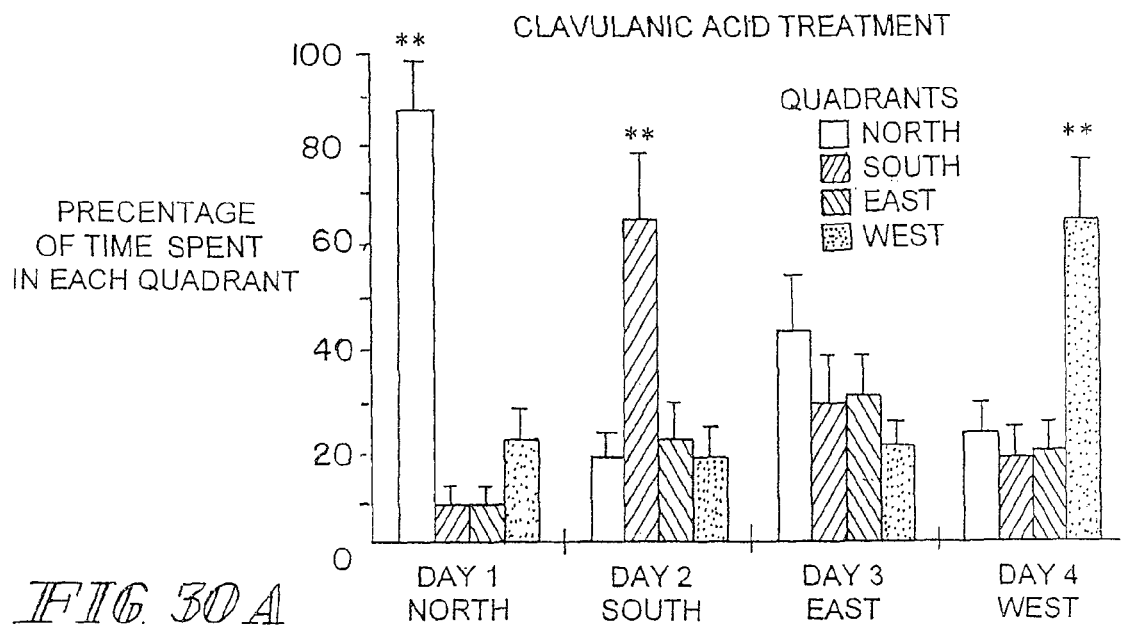
Figure 30B:
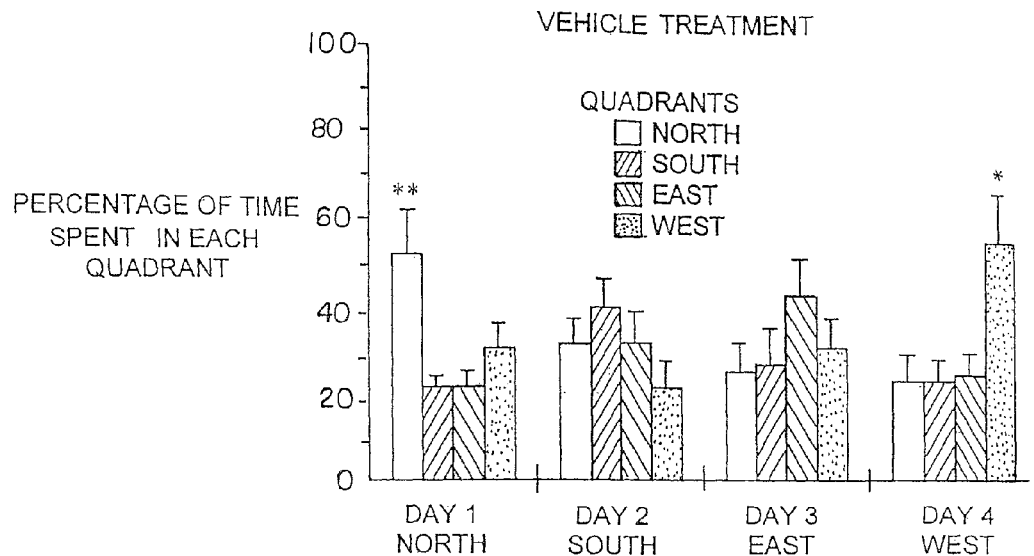

The strategy for finding the platform was similar for both treatments (FIGS. 30A & B) as judged by the percentage of time the animals spent in each quadrant. For any quadrant on any day there was no significant difference between treatments. There was a significant difference between days for percentage of time spent in any particular quadrant (e.g., CLAV, North Quadrant, $F_{(3,32)}$=38.81, p<0.0001). Animals spent a significant portion of their time in certain quadrants on certain days. For example, on Day 1 both CLAV and vehicle animals spent most of their time in the North quadrant as compared to the other quadrants (p<0.01). This was to be expected since they had knowledge of the location of the platform in this quadrant from the familiarization procedure.

While the strategy for finding the platform as measured by percentage of time spent in each quadrant was similar between CLAV and vehicle there was a small but obvious difference. Animals treated with CLAV spent more time in the correct quadrant than animals treated with vehicle. This difference is particularly true on Day 2 when the CLAV animals spent over 50% (p<0.01) of their time in the correct (South) quadrant. The vehicle animals spent less than 40% of their time in the correct quadrant, a time not significantly different from the other quadrants. By Day 4 both CLAV and vehicle spent most of their time in the correct quadrant (West). This strategy on Day 4 shows good spatial, working and procedural memory for both treatments.

Figure 31:
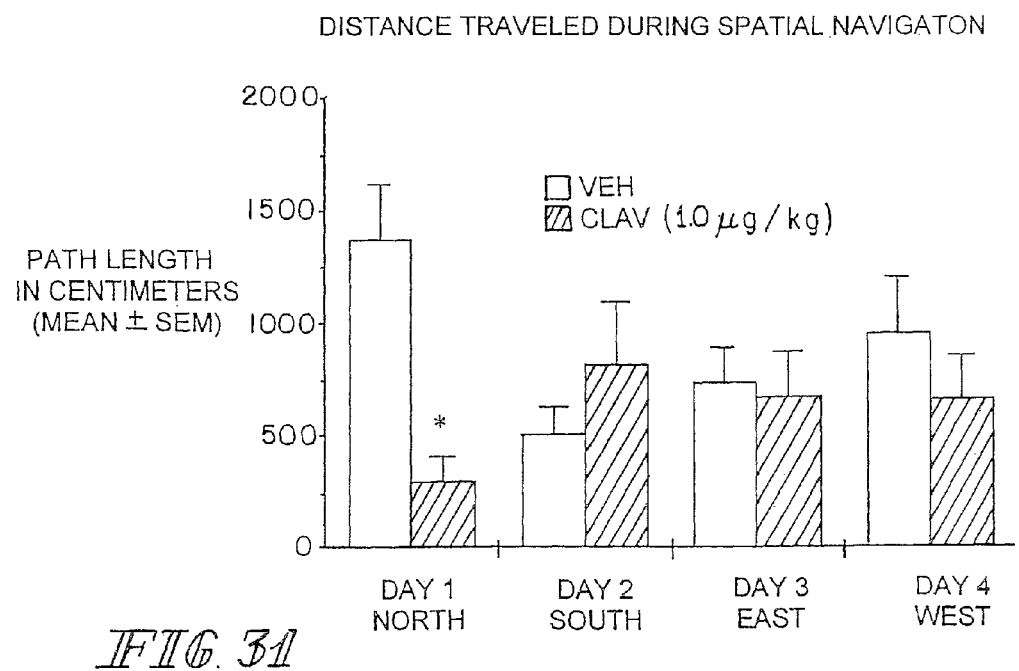
Figure 32:
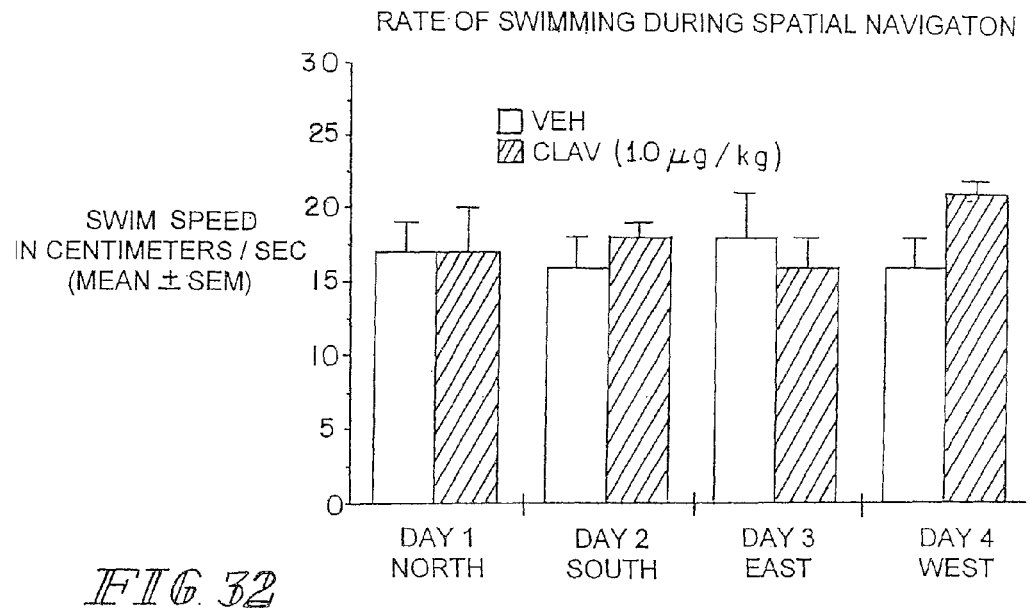

There was a significant main effect for treatment ($F_{(1,16)}$=8.40, p>0.01) on the path length to find the platform. On Day 1 CLAV treated animals (p<0.05) traveled a much shorter distance during the search for the platform than vehicle animals (FIG. 31). There was no significant difference between CLAV and vehicle on swim rate (FIG. 32).

2. Cue Navigation

Method

Figure 33:
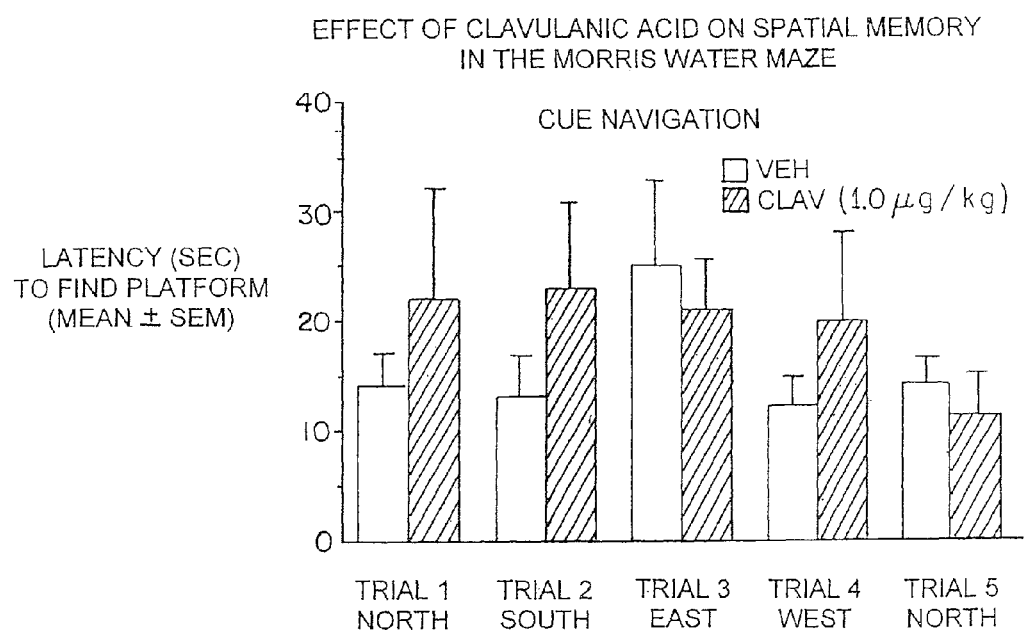

On the day following the last day (Day 4) of spatial navigation, animals were tested for cue navigation. In these tests, the platform was raised above water level. One hr before testing animals were treated with CLAV or saline vehicle. The same animals treated with CLAV during spatial navigation were treated with CLAV for cue navigation. Animals were run through a series of two min trials with 45 min between trials. At each trial, the platform was moved to a different quadrant. The cue navigation study was identical to the spatial navigation except the platform was visible and the testing was done over five consecutive trials done on a single day. Animals were scored for latency to find the platform, percent time spent in each quadrant, path distance and swim speed for all testing periods Results There was no main effect for treatments ($F_{(1,16)}=0.553$ p>0.1), trials ($F_{(4,64)}=0.9745$, p>0.1) or interaction between factors ($F_{(4,64)}=0.7433$, p>0.5) for latency to find the platform during cue navigation (FIG. 33).

As in spatial navigation, the strategy for finding the platform was very similar for both treatments (FIGS. 34A & B) as judged by the percentage of time the animals spent in each quadrant. For any quadrant on any trial there was no significant difference between treatments (e.g., Trial 1, North, $F_{(1,16)}=0.099$, p>0.5). There was a significant difference for percentage of time spent in any particular quadrant for either treatment for most of the trials, most notably for CLAV.

Figure 34A:
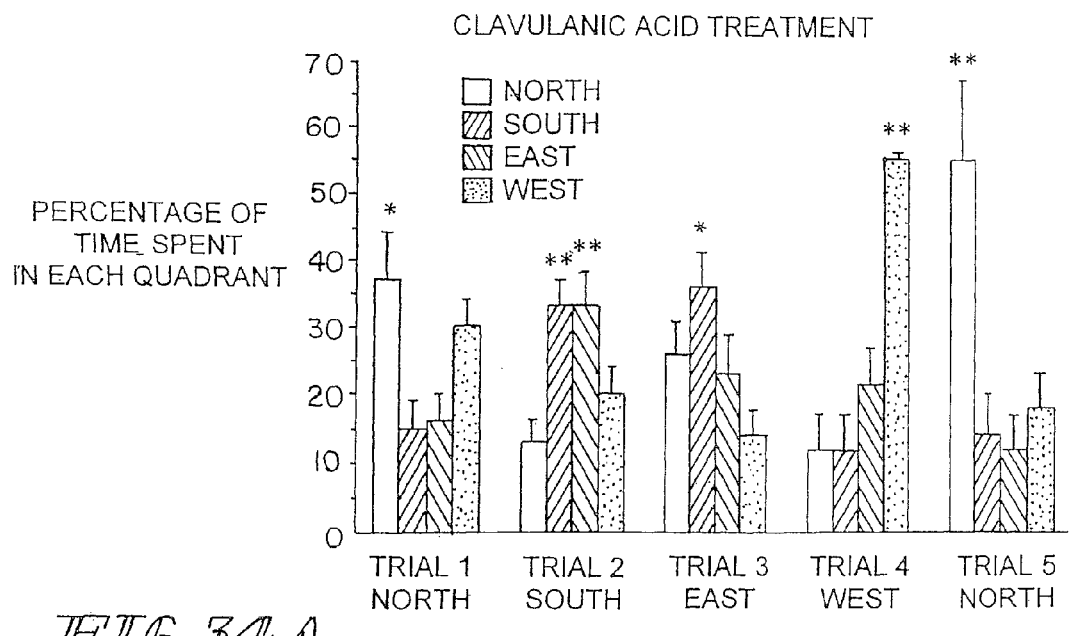
Figure 34B:
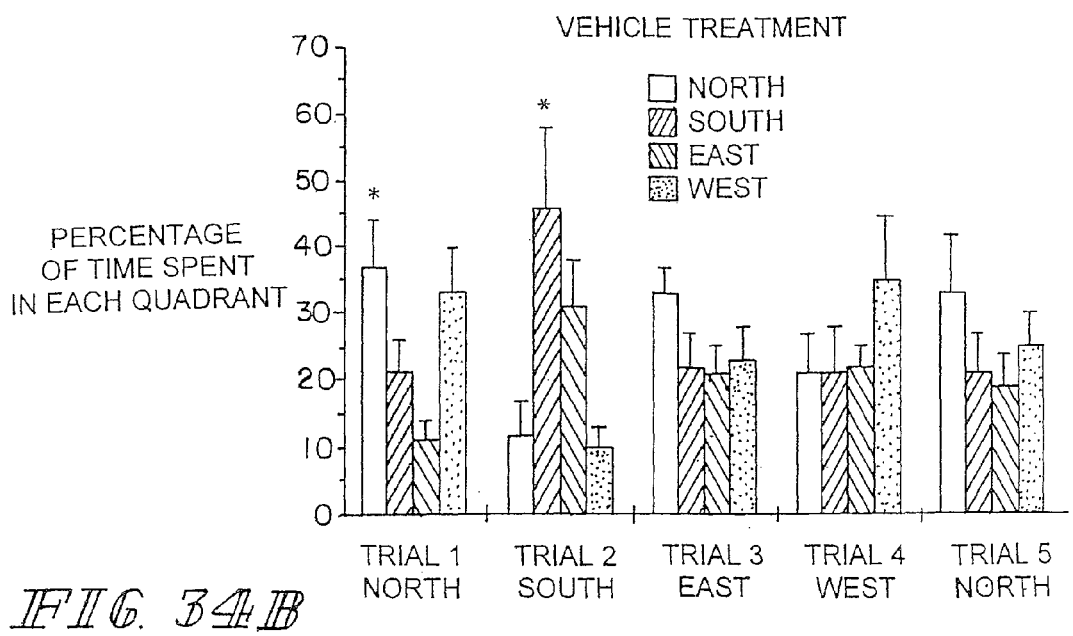
Figure 35:
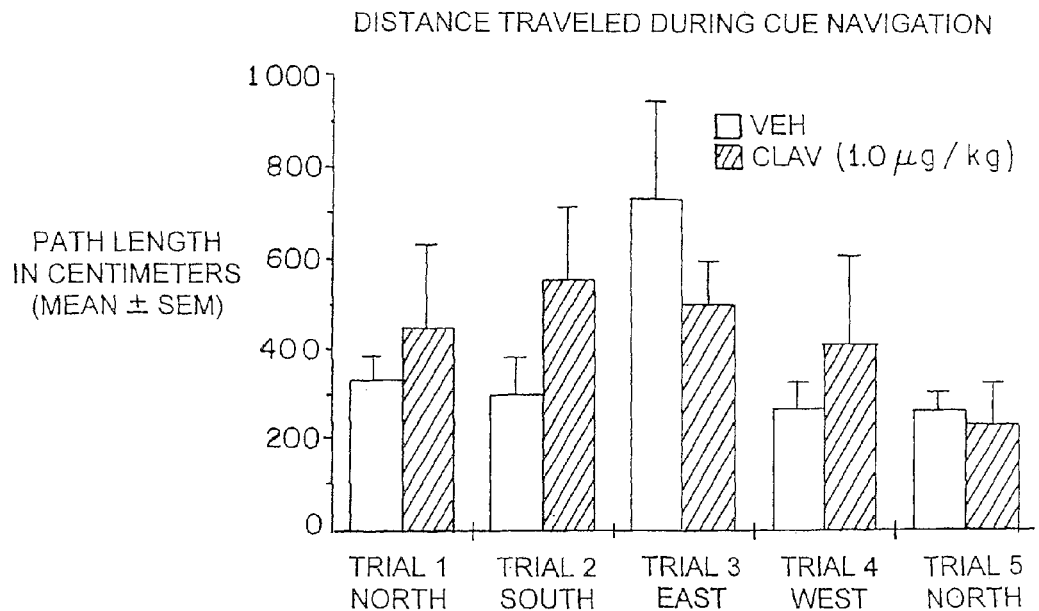
Figure 36:
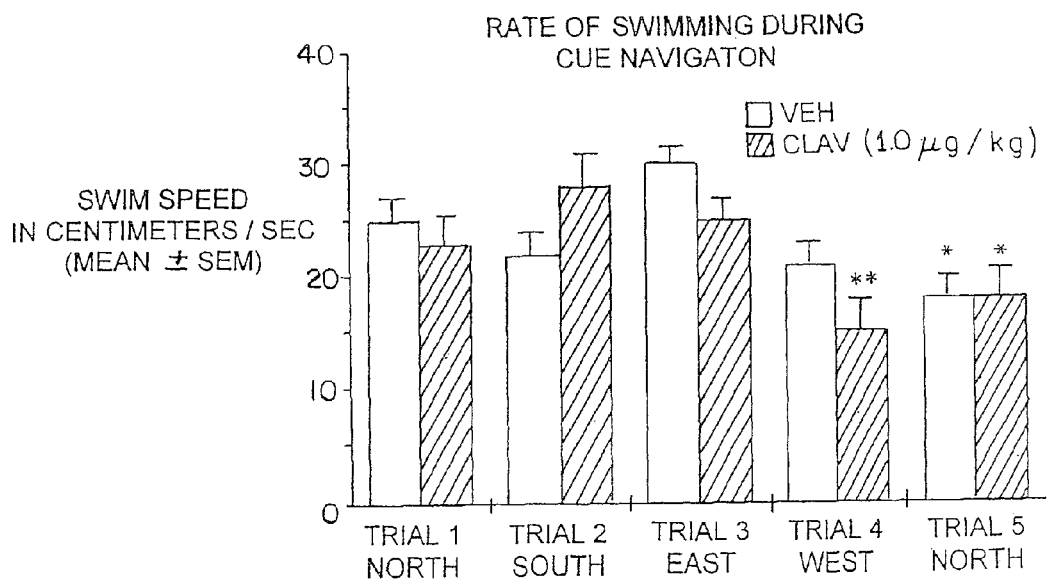

The distance traveled to find the platform was not significantly different between CLAV and vehicle animals ($F_{(1,16)}=0.23$ p>0.5) (FIG. 35). While there was no significant main effect for treatment on swim rate ($F_{(1,16)}=0.926$, p>0.1), there was a significant trails effect ($F_{(4,64)}=7.87$, p<0.001) and interaction between factors ($F_{(4,64)}=2.56$, p<0.05). Both treatments, but particularly CLAV showed reduced swim rates by Trial 4 (p<0.01) and Trial 5 (p<0.05). This probably reflects the fact that they knew where to look for the platform as shown in FIGS. 34A & B.

Summary

Clavulanic acid treated animals do not show any loss in learning and memory when tested for spatial and cue navigation in the Morris water maze. Indeed, on distance traveled to the hidden platform and percentage of time spent in the correct quadrant for both spatial and cue navigation, CLAV treated animals showed better performance than vehicle. These data show that the anxiolytic profile of CLAV is not accompanied by any disruption in learning and memory as is the case with benzodiazepine anxiolytics.

Studies on Mechanisms of Action

VI. Clavulanic Acid and the Stress Response

Rationale

The ability of CLAV to reduce anxiety in stressful situations, i.e. the food deprivation and novel environment in the seed finding assay, and exposure to light and a novel environment in the elevated plus-maze, without altering motor activity or cognitive function is a significant finding. The potential of CLAV as an anxiolytic and therapeutic in the treatment of numerous affective disorders could be broadened if we had a clearer understanding of its mechanism of action. For example, could CLAV be altering anxiety by suppressing the natural stress response? The commonly prescribed benzodiazepine anxiolytics block both the normal circadian release and stress-mediated release of the hormone cortisol (Gram and Christensen, 1986; Petraglia et al., 1986; Hommer et al., 1986).

Experimental Protocol

The simple procedure of placing an adult male hamster into a novel environment for 5 min causes a significant, predictable increase in blood levels of cortisol (Weinberg and Wong 1986). This novelty test was used to assess the effects of CLAV on stress-induced release of cortisol. Two groups of male hamsters were treated IP with either CLAV (10 µg/kg, n=6), or saline vehicle (n=4). A third group (n=4) received no treatment or isolation stress and served as a control for basal levels of cortisol. Sixty min after treatment animals were taken from their home cage and placed into a novel cage for 5 min. Afterwards animals were sacrificed by decapitation and trunk blood collected for radioimmunoassay of cortisol. All animals were tested under reverse light:dark conditions four hrs into the dark cycle. Data were compared with a one-way ANOVA followed by Fisher PLSD post hoc tests.

Results

There was a significant difference in the stress release of cortisol between treatments ($F_{(2,11)}=10.03$ p<0.01). Vehicle (p<0.05) and CLAV (p<0.01) showed more than twice the blood level of cortisol as compared to the untreated, non-stressed control (FIG. 37).

Summary

The data show that the beta-lactam anxiolytic CLAV has no ostensible effect on the release of cortisol in response to the mild stress of exposure to a novel environment. This detail, combined with the absence of motor depression and cognitive impairment makes CLAV unique amongst the anxiolytics and suggests a highly specific, novel mechanism of action. At first glance one might think it would be advantageous to suppress the stress response. Indeed, hypercortisolism has been implicated in the pathophysiology of depression (Sacher et al., 1973). Chronic psychosocial stress leading to dysfunctional, hyperactive adrenal glands can be life threatening. However, a responsive hypothalamic-pituitary-adrenal axis is critical for normal physiology and behavior. Stressors that would normally help animals adapt to the environment can be fatal without the appropriate release of cortisol.

VII. Territorial or Offensive Aggression

Rationale

Continuing to study the CNS activity of CLAV in more complex behavioral models may help to clarify its mechanism(s) of action. For example, antagonistic, social interactions between animals require risk assessment, communicative and agonistic behaviors to settle disputes over territory, mates, food, etc. The neurotransmitters serotonin and vasopressin are fundamental in the CNS organization and expression of these behaviors in animals and humans (Ferris et al., 1997; Coccaro et al., 1998; Ferris 2000). To this end, CLAV was tested for effects on territorial or offensive aggression, i.e. defense of the home burrow against intruders.

Agonistic behavior can be classified as either offensive or defensive aggression (Blanchard and Blanchard, 1977; Adams, 19798; Albert and Walsh, 1984). Offensive aggression is characterized by an aggressor initiating an attack on an opponent; while, defensive aggression lacks active approach. Both types of aggression have their own unique neurobehavioral systems. The stimuli that elicit offensive and defense attack are different, as are the sequences of behaviors that accompany each agonistic response. While much of the empirical data supporting the notion of unique offensive and defensive neural networks have been collected from animal models, there are interesting and compelling similarities in human aggression that suggest a similar neural organization (Blanchard, 1984). Offensive aggression is easily studied using male golden hamsters tested in a resident/intruder paradigm, an established model of offensive aggression (Ferris and Potegal 1988) in the context of defending the home burrow. Placing an unfamiliar male hamster into the home cage of another male hamster elicits a well-defined sequence of agonistic behaviors from the resident that includes offensive aggression.

Experimental Protocol

Hamsters are nocturnal and as such all behavioral tests were performed during the first four hrs of the dark phase under dim red illumination. The resident was scored for offensive aggression, e.g., latency to bite the intruder, the total number of bites, total contact time with the intruder and flank marking over a 10 min test period (Ferris and Potegal, 1988). Flank marking is a form of olfactory communication in which a hamsters arches its back and rubs pheromone producing flank glands against objects in the environment (Johnston, 1986). Flank marking frequency is greatly enhanced during aggressive encounters and is particularly robust in dominant animals initiating and winning fights (Ferris et al., 1987).

Five male golden hamsters (130-140 g) were given IP injections of CLAV (200 μg/kg) and saline vehicle in a volume of ca. 0.2 ml. In pilot studies, it was discovered CLAV given IP at 1.0 μg/kg had no effect on aggressive behavior. Hence, it was necessary to test CLAV at a higher concentration but in a dose range that was still acceptable for pharmaceutical studies on aggressive behavior. Vehicle and CLAV treatments were counter balanced and randomized so all five animals received each treatment separated by at least 48 hrs. Animals were tested 90 min after treatment over a 10 min observation period. Latencies and contact time were analyzed with a two-way ANOVA. Non-parametric data, i.e., number of bites and flank marks were analyzed by Wilcoxon matched-pairs signed-ranks test.

Results

Figure 38:
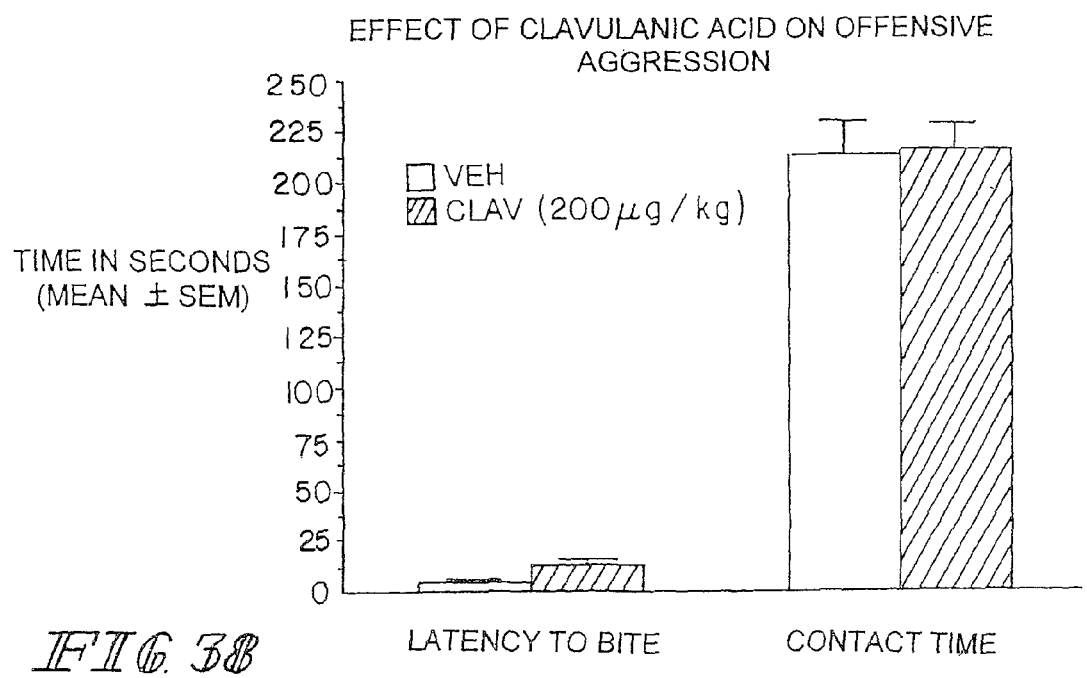

While there was no significant main effect for drug treatment ($F_{(1,3)}$=7.40, P<0.07) for latency to bite the intruder there was a trend toward significance (FIG. 38). There was no significant main effect for drug treatment ($F_{(1,3)}$=2.85, p>0.1) on contact time with the intruder (FIG. 38). There was a significant difference between drug treatments (T=3.0, p<0.05, N=8) and the number of bites on the intruder. CLAV treatment reduced the median number of bites to six as compared to thirteen for vehicle treated animals (FIG. 39). There was no significant effect of drug treatment (T=4.0, p>0.1, N=5) on the resident's flank marking behavior (FIG. 39).

Summary

Clavulanic acid has modest antiaggressive or serenic-like properties. Serenics are drugs used to treat impulsivity and violence (Olivier and Mos, 1991). Serenics should suppress offensive aggression without interfering with social, appetitive and cognitive behaviors. Social interest in an intruder, i.e. contact time was not altered by CLAV. Development of eltoprazine, one of the first serenics, was abandoned, in part, because it was found to increase fear and anxiety in animals (Olivier et al., 1994). The potent anxiolytic activity of CLAV excludes this possibility.

VIII. Interactions with Glutamyl Carboxypeptidase

CLAV has a very high binding affinity for the beta-lactamases. It is hypothesized that the presence of mammalian homologies to these bacterial enzymes and that these homologous proteins are involved in the regulation of neurotransmitter levels in the CNS. E Coli TEM beta lactamase has been cloned sequenced and crystilized to determine the active site motifs. The four putative binding sites on beta lactamase that could accommodate CLAV are designated active site I, II, III, and IV. These active sites, sequence location, and amino acid (AA) sequences are as follows:

```
Active site I:
                                          (SEQ ID NO: 1)
35 AA's downstream from N-terminus: STTK Active site II:
                                          (SEQ ID NO: 1)
57 AA's downstream from STTK motif: SGC, SGN, or SAN Active site III:
111 AA's downstream from SGC motif: KTG Active site IV:
                                          (SEQ ID NO: 2)
41 AA's downstream from SGC motif: ENKD
```

Screening for amino acid sequence homologies between these beta-lactamase binding sites and mammalian enzymes, Revaax scientists identified an enzyme system in the brain that CLAV would potentially bind in a similar manner to beta-lactamase. The enzyme glutamyl carboxypeptidase (N-acetyl, alpha linked, acidic dipeptidase) or NAALADase (Pangalos et al, 1999) is responsible for regulating the glutamatergic neurotransmission pathways whose effects would be expressed in such behavioral outcomes as aggression, memory/cognition, and anxiety. As a result of the almost perfect overlap of the putative active sites of beta-lactamase and the conserved sequences in human and rat NAALADase, it was hypothesized that CLAV affects behavior by inhibiting NAALADase activity. The overlap sequence similarity between beta-lactamase and NAALADase as shown below:

```
Active site I:
                                          (SEQ ID NO: 1)
Beta-lactamase: 35 AA's downstream from N-
terminus: SITK (SEQ ID NO: 3)
NAALADase: 38 AA's downstream from N-terminus:
STQK Active site II:
                                          (SEQ ID NO: 1)
Beta-lactamase: 57 AA's downstream from SITK motif: SGC, SGN, or SAN (SEQ ID NO: 3)
NAALADase: 59 AA's downstream from STQK motif: SEG Active site III:
Beta-lactamase: 111 AA's downstream from SGC motif: KTG NAALADase: 110 AA's downstream from SFG motif: KLG Active site IV:
                                          (SEQ ID NO: 2)
Beta-lactamase: 41 AA's downstream from SGC motif:
ENKD (SEQ ID NO: 4)
NAALADase: 41 AA's downstream from SFG motif: ERGV
```

Clavulanic acid inhibits gram negative beta-lactamase enzymes in the range of 15-34 nM CLAV is effective at a dose of 10 ng/kg in the seed finding model of anxiety (pg 3). If NAALADase were the human homologue to beta-lactamase then CLAV would be predicted to be a high affinity substrate.

IX. Seed Finding Following Blockade of NAALADase Activity

Rationale and Experimental Procedure

It was hypothesized that CLAV functioned as an anxiolytic in the seed finding assay by blocking NAALADase activity in the brain. If this notion were true then it would be predicted that drugs known to block NAALADase should also enhance seed finding. To this end, animals were treated with N-acetyl-beta-aspartyl-glutamic acid (beta-NAAG), a competitive inhibitor of NAALADase (Serval et al., 1992) and tested in the seed finding model of anxiety. The study was similar to that outlined in Section I with one notable exception. Since beta-NAAG does not readily cross the blood-brain barrier it had to be injected directly into the lateral ventricle where it could be carried by cerebrospinal fluid throughout the brain via the ventricular system. Beta-NAAG (FW 304) was given in a dose of 3 ng in a volume of 1 µl saline ICV. The average adult hamster brain weights ca. 1.2 g of which 22% is extracellular fluid. The estimated beta-NAAG concentration was 11 ng/ml or 36 nM.

Two groups of six animals each were fasted overnight as previously described and tested the following day. One group was treated with beta-NAAG and the other saline vehicle and one hr later timed for latency to find the hidden sunflower seeds. A Student t-test for unpaired data was used for statistical comparisons.

Results

Figure 40:
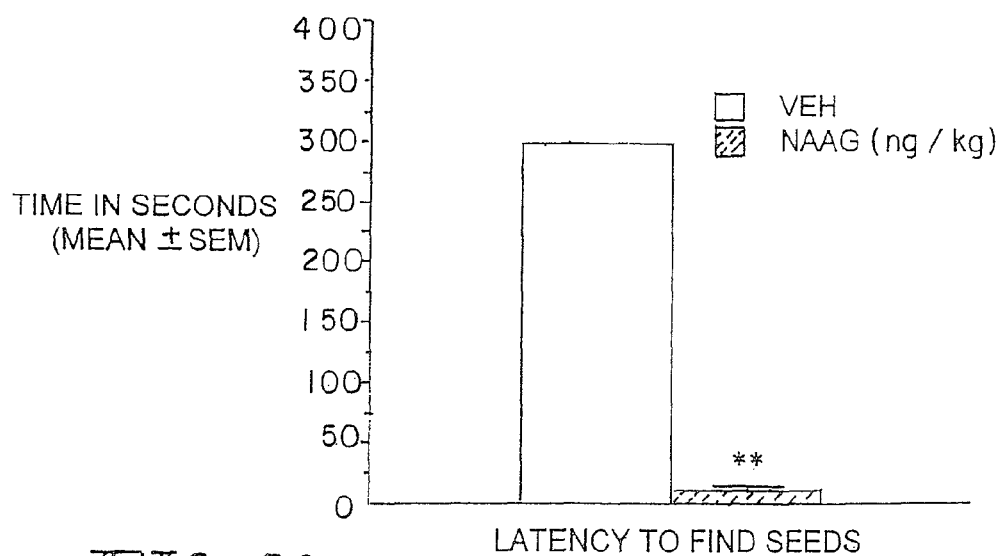

The difference in latency to find the seeds was significantly ($p<0.001$) different between treatments (FIG. 40). Indeed, the none of the six animals microinjected with saline vehicle found the seeds in the five min observation period. However, three days later when these same animals were microinjected with beta-NAAG (3 ng/µl) and tested for seed finding they showed a mean latency of 21.8±9.7 sec.

Summary

The data show that beta-NAAG a specific NAALADase inhibitor can dramatically reduced the latency to find hidden sunflower seeds, a biological activity shared by CLAV. Since beta-NAAG was active in the seed finding model of anxiety then the hypothesis that beta-NAAG and CLAV share a common mechanism of action is not rejected. From these data the hypothesis can be expanded to predict that beta-NAAG and CLAV show similar effects on a range of biological and behavioral measures. To this end, animals were tested for offensive aggression in the resident intruder paradigm as described in Section VII. As reported earlier, when given in high concentrations, CLAV has only a modest effect on offensive. While CLAV can enhance seed finding at a dose of 10 ng/kg it has only a modest effect on offensive aggression even with doses as high as 200 µg/kg. If beta-NAAG and CLAV share a common mechanism then beta-NAAG should have little or no effect on aggression.

X. Effect of NAALADase Blockade on Offensive Aggression

Experimental Procedure

The animals tested in this study were those used in Section IX. After the seed finding assay, beta-NAAG (n=6) and saline vehicle (n=6) treated animals remained in their home cage and were presented with a smaller, male intruder. The resident was scored for latency to bite, bites, contact time and flank marking over a 10 min observation period. Latency to bite and contact time between treatments were compared with Student t-tests. Non-parametric measures of bites and flank marks for beta-NAAG vs vehicle were compared with Mann-Whitney.

Results

Figure 41:
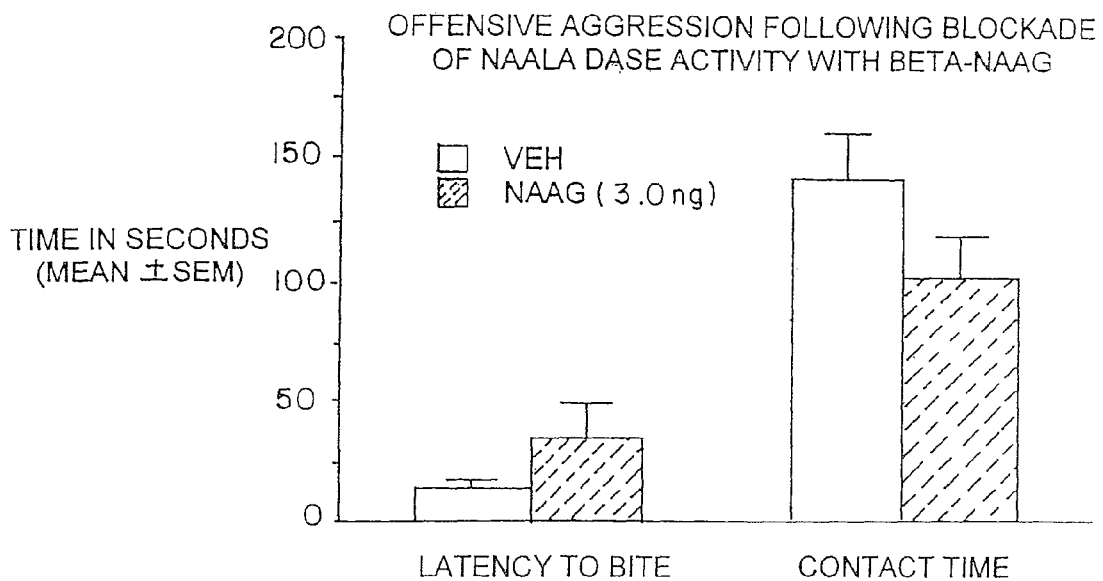
Figure 42:
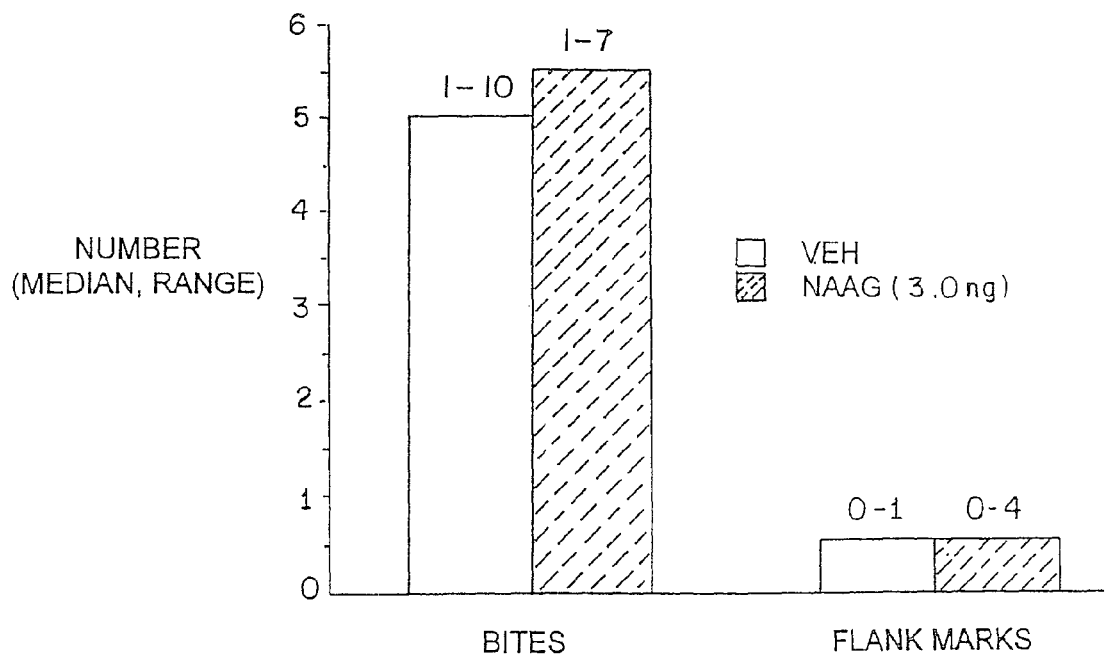

There were no significant differences between beta-NAAG and vehicle-treated animals for any measures of offensive aggression (FIGS. 41 & 42).

Summary

Blocking NAALADase activity with beta-NAAG does not alter offensive aggression as tested in the resident intruder paradigm. This finding is not inconsistent with the notion that CLAV and beta-NAAG share a common mechanism—blockade of NAALADase activity.

---

What is claimed is:

1. A method of enhancing cognitive function in a warm-blooded vertebrate in need of said treatment, said method comprising the step of administering to said warm-blooded vertebrate an effective amount of a compound capable of inhibiting the peptidase activity of one or more neurogenic peptidases in the brain of said patient.

2. The method of claim 1 wherein the warm-blooded vertebrate is a human patient suffering from dementia or amnesia.

3. The method of claim 1 wherein the warm-blooded vertebrate is a human patient suffering from Alzheimer's Disease.

4. The method of claim 1 wherein the compound is a β-lactam compound.

5. The method of claim 4 wherein the β-lactam compound is a β-lactamase inhibitor.

6. The method of claim 4 wherein the β-lactam compound is selected from the group consisting of penicillins, cephalosporins, penems, 1-oxa-1-dethia cephems, clavams, clavems, azetidinones, carbapenams, carbapenems, and carbacephems.

7. The method of claim 6 wherein the β-lactam compound is a 1-oxa-1-dethia-analogue of a cephalosporin.

8. The method of claim 1 further comprising the step of administering an effective amount of a P-glycoprotein efflux pump inhibitor.

9. The method of claim 6 wherein the β-lactam compound is administered in combination with an effective amount of a P-glycoprotein efflux pump inhibitor.

10. The method of claim 1 wherein the compound is a β-lactam antibiotic and the amount administered to the warm-blooded vertebrate is at least 50 μg/kg but less than an amount effective to provide clinically effective antibacterial blood levels of the compound.

11. The method of claim 1 wherein the compound is a compound of the formula:

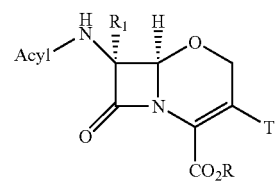

wherein R is hydrogen, a salt forming group or an active ester forming group; $R^1$ is hydrogen or $C_1$-$C_4$ alkoxy; T is $C_1$-$C_4$ alkyl, halo, hydroxy, O(C$_1$-C$_4$)alkyl, or —CH$_2$B, wherein B is the residue of a nucleophile B:H, and Acyl is the residue of an organic acid Acyl-OH.

12. The method of claim 11 wherein the compound is moxalactam or flomoxef.

13. The method of claim 12 further comprising the step of administering an effective amount of a P-glycoprotein efflux pump inhibitor.

14. The method of claim 1 wherein the compound is a 2-optionally substituted oxa-2-deamino analogue of glutamic acid, a 2-optionally substituted carba-2-deamino analogue of glutamic acid, or an N-substituted derivative of glutamic acid.

15. The method of claim 14 further comprising the step of administering an effective amount of a P-glycoprotein efflux pump inhibitor.

16. A method of treating cognitive disorders in a warm-blooded vertebrate in need of said treatment, said method comprising the step of inhibiting neurogenic peptidase activity in the brain of said vertebrate, said neurogenic peptidase characterized by its inhibition with effective amounts of the peptide Ala-D-γ-Glu-Lys-D-Ala-D-Ala.

17. The method of claim 16 wherein the step of inhibiting the neurogenic peptidase includes administering an effective amount of a β-lactam antibiotic effective to enhance the warm-blooded vertebrate's cognitive performance.

18. The method of claim 17 wherein the β-lactam antibiotic is administered in an amount less than that necessary to obtain antibiotically effective blood levels of said antibiotic.

19. The method of claim 16 wherein the inhibitor is a 2 optionally substituted oxa-2-deamino analogue of glutamic acid, a 2-optionally substituted carba-2-deamino analogue of glutamic acid, or an N-substituted derivative of glutamic acid.

20. The method of claim 19 further comprising the step of administering an effective amount of a P-glycoprotein efflux pump inhibitor.

21. The method of claim 16 wherein the warm-blooded vertebrate is a human patient suffering from dementia or amnesia.

22. The method of claim 16 wherein the warm-blooded vertebrate is a human patient suffering from Alzheimer's Disease.

23. The method of claim 16 wherein the step of inhibiting the neurogenic peptidase includes administering an effective amount of a β-lactam compound.

24. The method of claim 23 wherein the β-lactam compound is a β-lactamase inhibitor.

25. The method of claim 23 wherein the β-lactam compound is selected from the group consisting of penicillins, cephalosporins, penems, 1-oxa-1-dethia cephems, clavams, clavems, azetidinones, carbapenams, carbapenems, and carbacephems.

26. The method of claim 25 wherein the β-lactam compound is a 1-oxa-1-dethia-analogue of a cephalosporin.

27. The method of claim 25 wherein the β-lactam compound is administered in combination with an effective amount of a P-glycoprotein efflux pump inhibitor.

28. The method of claim 17 wherein the β-lactam antibiotic is administered to the warm-blooded vertebrate in an amount of at least 50 μg/kg but less than an amount effective to provide clinically effective antibacterial blood levels of the compound.

29. The method of claim 23 wherein the compound is of the formula:

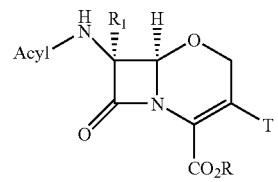

wherein R is hydrogen, a salt forming group or an active ester forming group; R$^1$ is hydrogen or C$_1$-C$_4$ alkoxy; T is C$_1$-C$_4$ alkyl, halo, hydroxy, O(C$_1$-C$_4$)alkyl, or —CH$_2$B, wherein B is the residue of a nucleophile B—H.

30. The method of claim 29 wherein the compound is moxalactam or flomoxef.

* * * * *